United States Patent
Shankar et al.

(10) Patent No.: US 10,689,656 B2
(45) Date of Patent: *Jun. 23, 2020

(54) EXPRESSION CONSTRUCTS AND METHODS OF GENETICALLY ENGINEERING METHYLOTROPHIC YEAST

(71) Applicant: Impossible Foods Inc., Redwood City, CA (US)

(72) Inventors: Smita Shankar, Millbrae, CA (US); Martin Andrew Hoyt, San Francisco, CA (US)

(73) Assignee: Impossible Foods Inc., Redwood City, CA (US)

(*) Notice: Subject to any disclaimer, the term of this patent is extended or adjusted under 35 U.S.C. 154(b) by 41 days.

This patent is subject to a terminal disclaimer.

(21) Appl. No.: 15/573,300

(22) PCT Filed: May 11, 2016

(86) PCT No.: PCT/US2016/031797
§ 371 (c)(1),
(2) Date: Nov. 10, 2017

(87) PCT Pub. No.: WO2016/183163
PCT Pub. Date: Nov. 17, 2016

(65) Prior Publication Data
US 2018/0127764 A1    May 10, 2018

Related U.S. Application Data

(60) Provisional application No. 62/313,491, filed on Mar. 25, 2016, provisional application No. 62/236,506, filed on Oct. 2, 2015, provisional application No. 62/222,388, filed on Sep. 23, 2015, provisional application No. 62/220,366, filed on Sep. 18, 2015, provisional application No. 62/203,052, filed on Aug. 10, 2015, provisional application No. 62/185,921, filed on Jun. 29, 2015, provisional application No. 62/183,074, filed on Jun. 22, 2015, provisional application No. 62/159,899, filed on May 11, 2015.

(51) Int. Cl.
| | | |
|---|---|---|
| C12N 15/81 | (2006.01) | |
| C07K 14/39 | (2006.01) | |
| C07K 14/415 | (2006.01) | |
| C07K 14/805 | (2006.01) | |
| C12N 1/16 | (2006.01) | |
| C12N 15/63 | (2006.01) | |

(52) U.S. Cl.
CPC .......... C12N 15/815 (2013.01); C07K 14/39 (2013.01); C07K 14/415 (2013.01); C07K 14/805 (2013.01); C12N 1/16 (2013.01); C12N 15/635 (2013.01); C12N 15/81 (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,886,753 A | 12/1989 | Marcker |
| 4,965,188 A | 10/1990 | Mullis et al. |
| 5,204,253 A | 4/1993 | Sanford et al. |
| 5,538,800 A | 7/1996 | Jin et al. |
| 6,013,863 A | 1/2000 | Lundquist et al. |
| 6,261,827 B1 | 7/2001 | Elrod |
| 6,329,571 B1 | 12/2001 | Hiei |
| 8,236,528 B2 | 8/2012 | Takagi et al. |
| 9,938,327 B2 | 4/2018 | Shankar et al. |
| 10,273,492 B2 * | 4/2019 | Shankar .............. C07K 14/39 |
| 2002/0194643 A1 | 12/2002 | Merot et al. |
| 2007/0031832 A1 | 2/2007 | Watt |
| 2008/0166757 A1 | 6/2008 | Bron et al. |
| 2011/0287467 A1 | 11/2011 | Crane |
| 2015/0299716 A1 * | 10/2015 | Zhou .................... C07K 14/39 |
| | | 435/69.1 |
| 2017/0188612 A1 | 7/2017 | Varadan |
| 2017/0349637 A1 | 12/2017 | Shankar et al. |
| 2017/0349906 A1 | 12/2017 | Shankar et al. |
| 2018/0371469 A1 | 12/2018 | Shankar et al. |
| 2019/0292217 A1 | 9/2019 | Davis |
| 2019/0292555 A1 | 9/2019 | Davis |

FOREIGN PATENT DOCUMENTS

| | | |
|---|---|---|
| EP | 2058398 | 5/2009 |
| EP | 2669375 | 12/2013 |
| JP | 2008017774 | 1/2008 |
| WO | WO 1998/012913 | 4/1998 |
| WO | WO 2004/057946 | 7/2004 |
| WO | WO 2004/099405 | 11/2004 |
| WO | WO 2008/090211 | 7/2008 |
| WO | WO 2009/009142 | 1/2009 |

(Continued)

OTHER PUBLICATIONS

Krainer et al., "Optimizing cofactor availability for the production of recombinant heme peroxidase in Pichia pastoris", Microbial Cell Factories, vol. 14, No. 1, Jan. 13, 2015.

Liu et al., "Balanced globin protein expression and heme biosynthesis improve production of human hemoglobin in *Saccharomyces cerevisiae*", Metabolic Engineering, vol. 21, pp. 9-16, 2014.

Fraser et al., "Safety Evaluation of Soy Leghemoglobin Protein Preparation Derived From Pichia pastoris , Intended for Use as a Flavor Catalyst in Plant-Based Meat", International Journal of Toxicology, vol. 37, No. 3, Apr. 11, 2018, pp. 241-262.

Proulx et al., "Iron Bioavailability of Hemoglobin from Soy Root Nodules Using a Caco-2 Cell Culture Model", J Agric Food Chem, vol. 54, pp. 1518-1522, 2006.

Mitrophanov et al., "Positive feedback cellular control systems." Bioessays, vol. 30, No. 6, pp. 542-555, 2008.

(Continued)

*Primary Examiner* — Nancy J Leith
(74) *Attorney, Agent, or Firm* — Fish & Richardson P.C.

(57) ABSTRACT

Methods and materials for genetically engineering methylotrophic yeast are provided.

28 Claims, 11 Drawing Sheets
Specification includes a Sequence Listing.

(56) References Cited

FOREIGN PATENT DOCUMENTS

| WO | WO 2012/083424 | 6/2012 |
|---|---|---|
| WO | WO 2013/010042 | 1/2013 |
| WO | WO 2014/008729 | 1/2014 |
| WO | WO 2014/110532 | 7/2014 |
| WO | WO 2014/110539 | 7/2014 |
| WO | WO 2015/153666 | 10/2015 |

OTHER PUBLICATIONS

Mitrophanov et al., "Positive autoregulation shapes response timing and intensity in two component signal transduction systems." J Mol Biol, vol. 401, No. 4, pp. 671-680, 2010.
Sasano et al., "Trm2p-dependent depression is essential for methanol-specific gene activation in the methylotrophic yeast *Candida boidinii*", FEMS Yeast Res., vol. 10, 535-544, 2010.
GenBank Accession No. AAA33980, "leghemoglobin [*Glycine max*]," Apr. 1993, 1 page.
[No Author Listed] Impossible Foods Inc. "GRAS Notification for Soybean Leghemoglobin Protein Derived from Pichia Pastoris." GRAS notice 000737, Retrieved from internet <URL:https://www.fda.gov/downloads/Food/IngredientsPackagingLabeling/GRAS/NoticeInventory/default.htm, 1063 pages, 2017.
Chenna et al., "Multiple sequence alignment with the Clustal series of programs" Nucleic Acids Res., 31(13):3497-500 (2003).
Chiruvolu et al., "Recombinant protein production in an alcohol oxidase-defective strain of Pichia pastoris in fedbatch fermentations" Enzyme Microb. Technol., 21: 277-83 (1997).
Cregg et al, "Recombinant protein expression in Pichia pastoris," Molecular Biotechnology, 16:23-52 (2000).
Dayhoff et al., "A Model of Evolutionary Change in Proteins," Atlas of Protein Sequence and Structure, 5: 345-352 (1978).
GenBank Accession No. AB365355, "Candida boidinii TRM1 gene for Zn(II)2Cys6-type transcription factor Trm1, complete cds," dated Jan. 24, 2008, 3 pages.
GenBank Accession No. AB548760, "Candida boidinii TRM2 gene for C2H2-type transcription factor Trm2, complete cds," dated May 14, 2010, 3 pages.
GenBank Accession No. ABD57365, "methanol expression regulator I [Komagataella pastoris]," dated Mar. 4, 2006, 2 pages.
GenBank Accession No. AEOI02000005, bases 858873 to 862352, "Ogataea parapolymorpha DL-1 chr3, whole genome shotgun sequence," dated Dec. 3, 2013, 186 pages.
GenBank Accession No. BAF99700, "Zn(II)2Cys6-type transcription factor Trm1 [Candida boidinii]," dated Jan. 23, 2008, 2 pages.
GenBank Accession No. BAJ07608, "C2H2-type transcription factor Trm2 [Candida boidinii]," dated May 13, 2010, 2 pages.
GenBank Accession No. DQ395124, "Pichia pastoris methanol expression regulator I gene, complete cds," dated Mar. 4, 2006, 2 pages.
GenBank Accession No. ESX01253, "Regulatory protein ADR1 [Ogataea parapolymorpha DL-1]," dated Dec. 2, 2013, 2 pages.
GenBank Accession No. FJ752551, "Pichia pastoris dihydroxyacetone synthase 1 (DAS1) gene, complete cds" dated Mar. 21, 2009, 2 pages.
GenBank Accession No. X02425, "Hansenula polymorpha MOX gene for methanol oxidase" dated Apr. 20, 1993, 3 pages.
GenBank Accession No. YSAAOD1A, "Candida boidinii methanol oxidase (AOD1) gene, complete cds," dated Apr. 27, 1993, 2 pages.
Hargrove et al., "Characterization of recombinant soybean leghemoglobin a and apolar distal histidine mutants" J Mol. Biol. 266, 1032-1042 (1997).
Inan & Meagher, "Non-repressing carbon sources for alcohol oxidase (AOX1) promoter of Pichia pastoris" J. Biosci. Bioeng., 92:585-9 (2001).
International Preliminary Report on Patentability in International Application No. PCT/US2016/031797, dated Nov. 14, 2017, 7 pages.

International Search Report and Written Opinion in International Application No. PCT/US2014/055227, dated Mar. 20, 2015, 20 pages.
Jokipii-Lukkari et al., "Intrinsic non-symbiotic and truncated haemoglobins and heterologous Vitreoscilla haemoglobin expression in plants," Journal of Experimental Botany, 60(2):409-422 (Jan. 2009).
Kranthi et al., "Identification of Mxr1p-binding sites in the promoters of genes encoding dihydroxyacetone synthase and peroxin 8 of the methylotrophic yeast *Pichia pastoris*" Yeast, 27:705-11 (2010).
Liachko & Dunham, "An autonomously replicating sequence for use in a wide range of budding yeasts" FEMS Yeast Res., 14:364-7 (2014).
Lin-Cereghino et al., "Mxr1p, a key regulator of the methanol utilization pathway and peroxisomal genes in Pichia pastoris," Molecular and Cellular Biology, 26:883-897 (Feb. 2006).
Lloyd et al., "Targeted mutagenesis using zinc-finger nucleases in *Arabidopsis*" Proc. Natl. Acad. Sci. USA, 102:2232-2237 (2005).
Londer et al. "Production and preliminary characterization of a recombinant triheme cytochrom c(7) from Geobatcher sulfurreducens in *Escherichia coli*." Biochem Biophy Act 1 1554(3): 202-211 (2002).
Lutz et al., "A guide to choosing vectors for transformation of the plastid genome of higher plants" Plant Physiol. 145: 1201-1210 (2007).
Miele et al., "A GATA-type transcription factor regulates expression of the high-affinity iron uptake system in the methylotrophic yeast *Pichia pastoris*" Arch. Biochem. Biophys., 465: 172-9 (2007).
Nakagawa et al., "Alcohol oxidase hybrid oligomers formed in vivo and in vitro" Yeast, 15: 1223-30 (1999).
Qu et al., "Ectopic expression of the cottong non-symbiotic hemoglobin gene GhHb1 triggers defense responses and increases disease tolerance in *Arabidopsis*," Plant Cell Physiol., 47:1058-1068 (2006).
Raymond et al., "Development of the methylotrophic yeast *Pichia methanolica* for the expression of the 65 kilodalton isoform of human glutamate decarboxylase" Yeast, 14: 11-23 (1998).
Richards et al., "Construction of a GFP-BAR plasmid and its use for switchgrass transformation" Plant Cell. Rep. 20:48-20 54 (2001).
Sievers et al., "The Primary Structure of Soybean (*Glycine max*) Leghemoglobin c*," Acta Chemica Scandinavico B, 32:380-386 (1978).
Sinagawa-Garcia et al., "Next generation synthetic vectors for transformation of the plastid genome of higher plants" Plant Afol Biol 70: 487-498 (2009).
Somleva et al., "Agrobacterium-Mediated Genetic Transformation of Switchgrass" Crop Sci. 42:2080-2087 (2002).
Supplementary European Search Report in International Application No. EP 14844701.4, dated Jan. 27, 2017, 7 pages.
Tanaka and Tanaka, "Tetrapyrrole biosynthesis in higher plants" Annu. Rev. Plant Biol. 58: 321-46 (2007).
Tovkach et al., "A toolbox and procedural notes for characterizing novel zinc finger nucleases for genome editing in plant cells" Plant J, 57: 747-757 25 (2009).
Townsend et al., "High-frequency modification of plant genes using engineered zinc-finger nucleases" Nature 459: 442-445 (2009).
UniprotKB Accession No. P02236, "Leghemoglobin C2," dated Nov. 1, 1988, 9 pages.
Wu et al., "Efficient production of a functional single-chain antidigoxin antibody via an engineered Bacillus subtilis expression-secretion system" Bio/Technology (NY) 11(1): 71-76 (1993) (abstract only).
Xie and Yang, "RNA-guided genome editing in plants using a CRISPR-Cas system" Mal. Plant 6: 1975-1983 (2013).
Zhang et al., "Transcription activator-like effector nucleases enable efficient plant genome engineering" Plant Physiology 161: 20-27 (2013).
GenBank Accession No. AF066054.1, "Pichia pastoris formaldehyde dehydrogenase (FLD1) gene, complete cds," dated Sep. 17, 1998, 2 pages.
GenBank Accession No. AY288296.1, "Pichia pastoris 3-phosphoglycerate kinase (PGK1) gene, complete cds," dated Jul. 22, 2005, 2 pages.

(56) References Cited

OTHER PUBLICATIONS

GenBank Accession No. CAY70887.1, "Hypothetical protein PAS_chr3_0836 [Komagataella phaffii GS115]," dated Feb. 27, 2015, 2 pages.
GenBank Accession No. U62648.1, "Pichia pastoris glyceraldehyde-3-phosphate dehydrogenase (GAP) gene, complete cds," dated Mar. 7, 1997, 2 pages.
GenBank Accession No. XM_002490678.1, "Komagataella phaffii GS115 Hypothetical protein (PAS_chr1-4_0586), partial Mrna," dated Jul. 22, 2009, 2 pages.
Hoffman, et al., "Identification of rate-limiting steps in yeast heme biosynthesis,"Biochem. Biophys. Res. Commun., 2003, 310(4):1247-1253.
PCT International Search Report and Written Opinion in International Appln. No. PCT/US2016/031797, dated Sep. 20, 2016, 9 pages.
Supplementary European Search Report and Opinion in EP Appln. No. EP 16793420.7, dated Aug. 29, 2018,8 pages.

\* cited by examiner (i)

(ii)

A

B

C

| Strain | Relative yield of heme loaded LegH |
|---|---|
| 183- BMGY | N/A |
| 183- BMY | 1 |
| 206- BMGY | 3 |
| 206- BMY | 5 |

| MXY Strain | Yield on glycerol co-feed | Yield on dextrose co-feed |
|---|---|---|
| 183 | 1X | 1X |
| 207 | 4.4X | 4.4X |
| 291 | 5.8X | 5.8X |
| 306 | 5.8X | 5.8X |
| 330 | 6.9X | 6.9X |
| 333 | 5.8X | 5.8X |
| 338 | 6.9X | 6.9X |

Figure 11

EXPRESSION CONSTRUCTS AND METHODS OF GENETICALLY ENGINEERING METHYLOTROPHIC YEAST

CROSS-REFERENCE TO RELATED APPLICATIONS

This application is a National Stage Application under 35 U.S.C. § 371 and claims the benefit of International Application No. PCT/US2016/031797 filed May 11, 2016, which claims priority to U.S. Provisional Application No. 62/313,491 filed Mar. 25, 2016, U.S. Provisional Application No. 62/236,506 filed Oct. 2, 2015, U.S. Provisional Application No. 62/222,388 filed Sep. 23, 2015, U.S. Provisional Application No. 62/220,366 filed Sep. 18, 2015, U.S. Provisional Application No. 62/203,052 filed Aug. 10, 2015, U.S. Provisional Application No. 62/185,921 filed Jun. 29, 2015, U.S. Provisional Application No. 62/183,074 filed Jun. 22, 2015, and U.S. Provisional Application No. 62/159,899 filed May 11, 2015. The disclosures of the foregoing applications are hereby incorporated by reference in their entirety.

TECHNICAL FIELD

This disclosure generally relates to DNA constructs and methods of using such DNA constructs to genetically engineer methylotrophic yeast.

BACKGROUND

Methylotrophic yeast such as *Pichia pastoris* are commonly used for expression of recombinant proteins. Constructs that can be used to efficiently express one or more polypeptides in a methylotrophic yeast are provided herein.

SUMMARY

This disclosure describes the use of *P. pastoris* strains that overexpress the transcriptional activator, Mxr1, from the AOX1 promoter to increase expression of transgenes that also are expressed from the AOX1 promoter, which significantly improves the recombinant production of one or more proteins. In addition, expression of Mxr1 from the AOX1 promoter creates a positive feedback loop that allows for expression of other transgenes from the AOX1 promoter in the absence of methanol, the normally obligate inducer, when repressing carbon sources are depleted. Expression of Mxr1 results in a significant increase in the amount of protein produced.

In one aspect, a methylotrophic yeast cell is provided that includes a recombinant nucleic acid molecule. The recombinant nucleic acid molecule typically includes an exogenous nucleic acid encoding a transcriptional activator operably linked to at least one methanol-inducible promoter element. Representative methylotrophic yeast can be of the genus *Candida, Hansenula, Pichia* or *Toruplosis*. A representative methylotrophic yeast is *Pichia pastoris*.

In some embodiments, the recombinant nucleic acid molecule is stably integrated into the genome of the methylotrophic yeast cell. In some embodiments, the recombinant nucleic acid molecule is extrachromosomally expressed from a replication-competent plasmid.

In some embodiments, the exogenous nucleic acid encoding a transcriptional activator comprises a Mxr1 sequence from *Pichia pastoris*, a Adr1 sequence from *Hansenula polymorpha*, a Trm1 sequence from *Candida boidinii*, and a Trm2 sequence from *Candida boidinii*. A representative nucleic acid encoding a transcriptional activator is shown in DQ395124. A representative transcriptional activator has an amino acid sequence shown in ABD57365.

In some embodiments, the at least one methanol-inducible promoter element is an alcohol oxidase 1 (AOX1) promoter element from *Pichia pastoris*, an AOD1 promoter element from *Candida boidinii*, a MOX promoter element from *Hansenula polymorpha*, a MOD1 promoter element from *Pichia methanolica*, a DHAS promoter element from *Pichia pastoris*, a FLD1 promoter element from *Pichia pastoris*, or a PEX8 promoter element from *Pichia pastoris*.

In some embodiments, the methylotrophic yeast cell further includes a nucleic acid molecule that includes at least one heterologous nucleic acid encoding a polypeptide operably linked to at least one methanol-inducible promoter element. In some embodiments, the at least one heterologous nucleic acid encodes one or more polypeptides involved in the biosynthesis of an iron co-factor such as heme (e.g., ALA synthase, ALA dehydratase, porphogilinogen deaminase, UPG III synthase, UPG III decarboxylase, CPG oxidase, PPG oxidase, and/or ferrochelatase). In some embodiments, one or more of the polypeptides involved in the biosynthesis of the iron co-factor are linked to at least one methanol-inducible promoter element.

In another aspect, a method for expressing a heterologous polypeptide in a cell is provided. Such a method typically includes providing a methylotrophic yeast cell as described herein; introducing a recombinant nucleic acid molecule into methylotrophic yeast cell, the recombinant nucleic acid molecule comprising at least one heterologous nucleic acid encoding a polypeptide operably linked to at least one *Pichia pastoris* alcohol oxidase 1 (AOX1) promoter element; and culturing the cell under conditions suitable for expression of the recombinant nucleic acid molecule, thereby expressing the heterologous polypeptide.

In some embodiments, the conditions under which the cells are cultured includes the addition of iron or a pharmaceutically or metabolically acceptable salt thereof. In some embodiments, the introducing step includes a technique such as transduction, electroporation, biolistic particle delivery, or chemical transformation. In some embodiments, the culturing step includes culturing the cell in the present of methanol.

In another aspect, a recombinant organism is provided that includes a transcriptional activator operably linked to the promoter it activates. In some embodiments, a recombinant organism is provided that expresses a polypeptide operably linked to the promoter. In yet another aspect, a method of expressing a polypeptide from an inducible promoter without addition of an inducer is provided as described herein.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 11 is a summary table showing relative yields of strains described herein when grown in the presence of methanol with glycerol or methanol with glucose in 2 L fermenter tanks.

DETAILED DESCRIPTION

Figure 1:
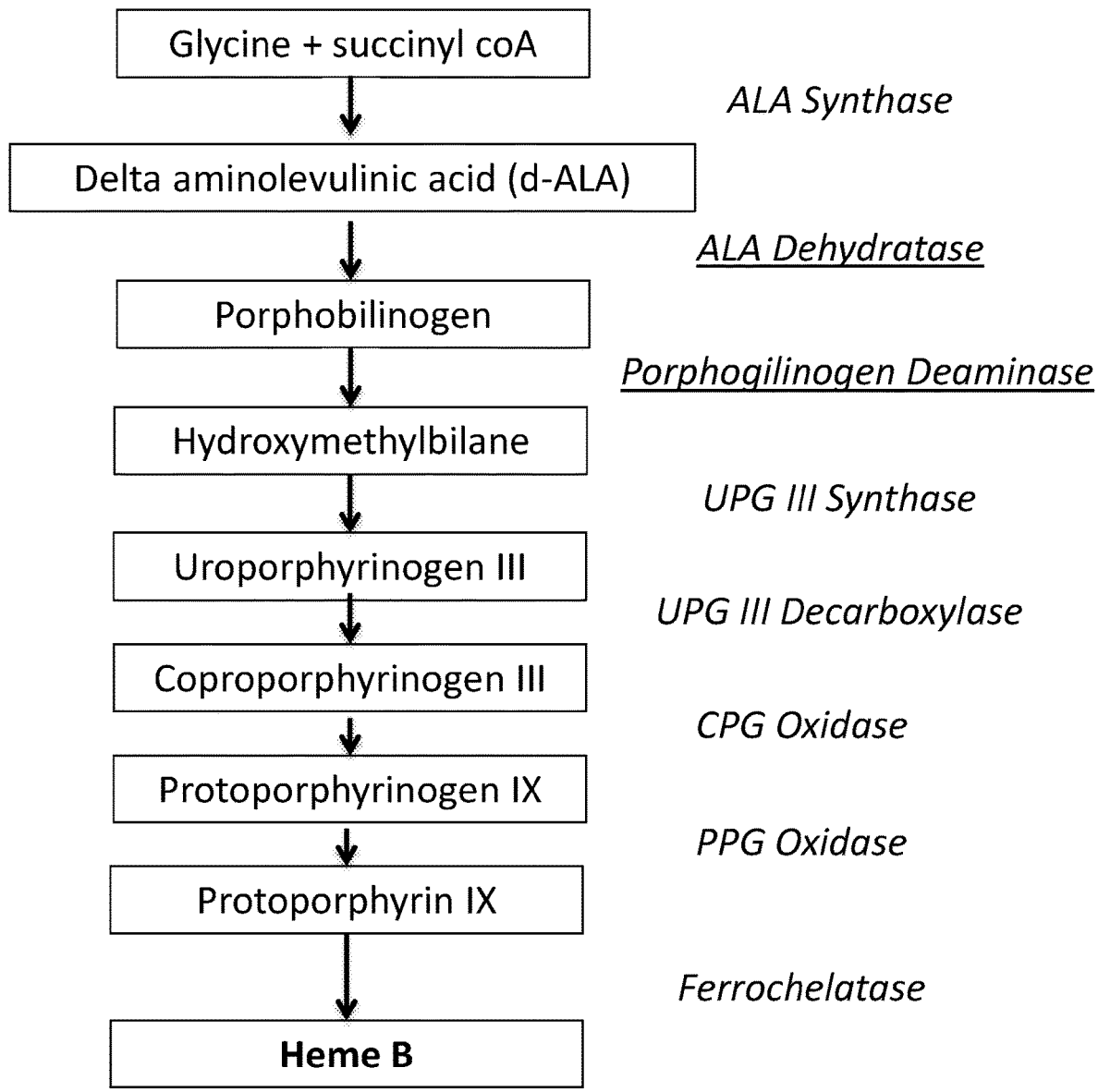
FIG. 1 is a schematic depicting the steps involved in the heme biosynthesis pathway.

Nucleic acid constructs are provided herein that allow for genetically engineering a cell to increase the recombinant expression of a polypeptide. In some embodiments, nucleic acid constructs are provided herein that allow for genetically engineering a cell to increase the recombinant expression of a polypeptide from an inducible promoter in the absence of the inducing molecule. Without being bound by any particular mechanism, the methods described herein create a positive feedback loop where the low level native expression of a transcriptional activator induces a promoter that is operably linked to a transcriptional activator. This leads to an increased expression of the transcriptional activator as well as one or more target polypeptides that are operably linked to the same inducible promoter.

Nucleic acid constructs are provided herein that allow for genetically engineering a methylotrophic yeast cell. While the methods are exemplified herein using a *Pichia* species (i.e., *P. pastoris*), other species of the *Pichia* genus can be used or species from any of the *Candida*, *Hansenula*, *Pichia* and *Torulopsis* genera.

Genetically engineering a methylotrophic yeast cell typically includes introducing a recombinant nucleic acid molecule into the cell. As described herein, a recombinant nucleic acid molecule typically includes an exogenous nucleic acid that encodes a transcriptional activator operably linked to at least one inducible promoter element.

Recombinant nucleic acid molecules used in the methods described herein are typically DNA, but RNA molecules can be used under the appropriate circumstances. As used herein, "exogenous" refers to any nucleic acid sequence that is introduced into the genome of a cell from an external source, where the external source can be the same or a different organism or a nucleic acid generated synthetically. For example, an exogenous nucleic acid can be a nucleic acid from one microorganism (e.g., one genus or species of methylotrophic yeast) that is introduced into a different genus or species of methylotrophic yeast, however, an exogenous nucleic acid also can be a nucleic acid from a methylotrophic yeast that is introduced recombinantly into a methylotrophic yeast as an additional copy despite the presence of a corresponding native nucleic acid sequence. For example, *P. pastoris* contains an endogenous nucleic acid encoding a Mxr1 transcriptional activator; an additional *P. pastoris* Mxr1 nucleic acid (e.g., introduced recombinantly into *P. pastoris*) or modifying the endogenous *P. pastoris* Mxr1 nucleic acid is considered exogenous.

Transcriptional activators, and nucleic acids encoding transcriptional activators (e.g., exogenous nucleic acids encoding transcriptional activators), are known in the art. For example, a transcriptional activator from *Pichia pastoris* is the Mxr1 sequence, but suitable transcriptional activators also can be found in *Hansenula polymorpha* (the Adr1 sequence; see, for example, GenBank Accession No. AE0102000005, bases 858873 to 862352, for the nucleic acid sequence and GenBank Accession No. ESX01253 for the amino acid sequence) and *Candida boidinii* (the Trm1 sequence; see, for example, GenBank Accession No. AB365355 for the nucleic acid sequence and GenBank Accession No. BAF99700 for the amino acid sequence; the Trm2 sequence; see, for example, GenBank Accession No. AB548760 for the nucleic acid sequence and GenBank Accession No. BAJ07608 for the amino acid sequence). A representative *P. pastoris* Mxr1 nucleic acid sequence can be found, for example, in GenBank Accession No. DQ395124, while a representative *P. pastoris* Mxr1 polypeptide sequence can be found, for example, in GenBank Accession No. ABD57365.

Transcriptional activators such as Mxr1 may be normally expressed at low levels. Therefore, it is desirable to place the exogenous nucleic acid (i.e., the transcriptional activator) under control of a promoter that is inducible. As used herein, "operably linked" means that a promoter or other expression element(s) are positioned relative to a nucleic acid coding sequence in such a way as to direct or regulate expression of the nucleic acid (e.g., in-frame).

There are a number of inducible promoters that can be used when genetically engineering methylotrophic yeast. For example, a methanol-inducible promoter, or a promoter element therefrom, can be used. Methanol inducible promoters are known in the art. For example, a commonly used methanol-inducible promoter from *P. pastoris* is the promoter, or a portion thereof, from the alcohol oxidase 1 (AOX1) gene, which is strongly transcribed in response to methanol. Other methanol-inducible promoters, or promoter elements therefrom, however, can be used, including, without limitation, the alcohol oxidase (AOD1) promoter from *Candida boidinii* (see, for example, GenBank Accession No. YSAAOD1A), the alcohol oxidase (MOX) promoter from *Hansenula polymorpha* (see, for example, GenBank Accession No. X02425), the MOD1 or MOD2 promoter from *Pichia methanolica* (see, for example, Raymond et al., 1998, Yeast, 14:11-23; and Nakagawa et al., 1999, Yeast, 15:1223-30), the DHAS promoter from *P. pastoris* (see, for example, GenBank Accession No. FJ752551) or a promoter element therefrom, the formaldehyde dehydrogenase (FLD1) promoter from *Pichia pastoris* (see, for example, GenBank Accession No. AF066054), or the PEX8 promoter from *P. pastoris* (see, for example, Kranthi et al., 2010, Yeast, 27:705-11). In some embodiments, the transcriptional activator is a Mit1 sequence from *Pichia pastoris* (see, for example, GenBank Accession No. CAY70887). All of these promoters are known to be induced by methanol.

A skilled artisan would understand that the recombinant nucleic acid molecule described herein can be stably integrated into the genome of the methylotrophic yeast cell, or can be extrachromosomally expressed from a replication-competent plasmid. Methods of achieving both are well known and routinely used in the art.

As demonstrated herein, the methanol-regulated transcriptional activators in *Pichia* can bind to the AOX1 promoter and act cooperatively with Mxr1 to activate transcription from the AOX1 promoter. In some embodiments, two methanol-regulated transcriptional activators (e.g., Mxr1 and Mit1) can be operably linked to a methanol inducible promoter element.

A strain that includes a recombinant nucleic acid molecule as described herein can be used to regulate (e.g., overexpress) a second recombinant nucleic acid molecule in the methylotrophic yeast cell. A second recombinant nucleic acid molecule can include, for example, one or more heterologous nucleic acids encoding one or more polypeptides of interest. Similar to the exogenous nucleic acid encoding the transcriptional activator, a heterologous nucleic acid refers to any nucleic acid sequence that is not native to the genome or in the genome of an organism (e.g., a heterologous nucleic acid can be a nucleic acid from one microorganism (e.g., one genus or species of methylotrophic yeast) that is introduced into a different genus or species of methylotrophic yeast).

Simply by way of example, heterologous nucleic acids encoding the one or more polypeptides of interest can be the nucleic acids involved in the biosynthesis of a heme-co-factor. Exemplified herein are nucleic acids encoding the 8 different enzymes involved in heme biosynthesis as determined and annotated from the sequence of the *Pichia pastoris* genome. For example, heterologous nucleic acids encoding ALA synthase, ALA dehydratase, porphobilinogen deaminase, UPG III synthase, UPG III decarboxylase, CPG oxidase, PPG oxidase, and ferrochelatase can be expressed in the methylotrophic yeast strains described herein. For genetically engineering methylotrophic yeast to contain more than one heterologous nucleic acids (e.g., transgenes), a combination of methanol-inducible and constitutive promoters, or elements therefrom, can be combined to further increase the expression of such nucleic acids.

Previous studies in *Saccharomyces cerevisiae* identified ALA dehydratase and porphobilinogen deaminase as rate limiting enzymes in heme biosynthesis (see, for example, Hoffman et al., 2003, Biochem. Biophys. Res. Commun., 310(4):1247-53). However, heterologous expression of individual heme enzymes in *P. pastoris* from the glyceraldehyde-3-phosphate dehydrogenase (GAP) promoter failed to overcome limitations associated with the expression of a recombinant protein containing a heme co-factor (see Krainer et al., 2015, Microb. Cell Fact., 13; 14:4). As described herein, highly efficient expression of a recombinant heme containing protein in *P. pastoris* was achieved by co-expressing the entire heme biosynthetic pathway from methanol-inducible promoters, although it would be appreciated that one or more of the genes involved in the heme biosynthetic pathway could be expressed from one or more constitutive promoters.

In addition to the enzymes involved in iron-co-factor biosynthesis, it would be understood that a nucleic acid encoding a member of the globin family of proteins (PF00042 in the Pfam database) including plant hemoglobins can be present. In the Examples herein, a nucleic acid encoding soybean leghemoglobin (LegH) is present. LegH is a protein that binds to the iron co-factor, heme, which results in a characteristic absorption at 415 nm and a distinct red color. The LegH protein (also known as LGB2) is naturally found in root nodules of soybean (see, for example, UniprotKB Accession No. P02236), and the nucleic acid sequence used herein was codon optimized for expression in *P. pastoris*. See, for example, WO 2014/110539 and WO 2014/110532.

Alternatively, a heterologous nucleic acid encoding a polypeptide of interest can be, for example and without limitation, a dehydrin, a phytase, a protease, a catalase, a lipase, a peroxidase, an amylase, a transglutaminase, an oxidoreductase, a transferase, a hydrolase, a lyase, an isomerase, a ligase, or an antibody against any such polypeptides. In other embodiments, a heterologous nucleic acid can encode one or more enzymes involved in the pathway for production of small molecules, such as ethanol, lactic acid, butanol, adipic acid, or succinic acid.

Similar to the exogenous nucleic acid encoding the transcriptional activator, the heterologous nucleic acid encoding a polypeptide of interest can be operably linked to an inducible promoter element (e.g., a methanol-inducible promoter element), or the heterologous nucleic acid encoding a polypeptide of interest can be operably linked to a constitutive promoter or constitutive promoter element. Inducible promoters and elements therefrom are discussed above. Constitutive promoters and constitutive promoter elements are known in the art. For example, a commonly used constitutive promoter from *P. pastoris* is the promoter, or a portion thereof, from the transcriptional elongation factor EF-1α gene (TEF1), which is strongly transcribed in a constitutive manner. Other constitutive promoters, or promoter elements therefrom, however, can be used, including, without limitation, the glyceraldehyde-3-phosphate dehydrogenase (GAPDH) promoter from *P. pastoris* (see, for example, GenBank Accession No. U62648.1), the promoter from the potential glycosyl phosphatidyl inositol (GPI)-anchored protein, GCW14p (PAS_chr1-4_0586), from *P. pastoris* (see, for example, GenBank Accession No. XM_002490678), or the promoter from the 3-phosphoglycerate kinase gene (PGK1) from *P. pastoris* (see, for example, GenBank Accession No. AY288296).

Similar to the recombinant nucleic acid molecule described herein, the second recombinant nucleic acid molecule can be stably integrated into the genome of the methylotrophic yeast cell, or can be extrachromosomally expressed from a replication-competent plasmid.

It would be understood by the skilled artisan that a combination of inducible (e.g., methanol-inducible) and constitutive promoters (or promoter elements therefrom) can be combined to further increase the expression of any of the nucleic acids operably linked thereto.

It would be appreciated by a skilled artisan that a heterologous nucleic acid encoding a polypeptide of interest operably linked to a promoter element can be separate from the recombinant nucleic acid molecule described herein, or can be contiguous with the exogenous nucleic acid encoding a transcriptional activator operably linked to a promoter element contained within the recombinant nucleic acid molecule described herein. It also would be appreciated by a skilled artisan that, if the second nucleic acid molecule is contiguous with the recombinant nucleic acid molecule described herein, that a single promoter, or promoter element therefrom, can be used to drive transcription of both or all of the genes (e.g., the exogenous nucleic acid encoding the transcriptional activator as well as the one or more heterologous nucleic acids encoding the polypeptide(s) of interest).

Methods of introducing nucleic acids into methylotrophic yeast cells are known in the art, and include, without limitation, transduction, electroporation, biolistic particle delivery, and chemical transformation.

In addition, methods of culturing methylotrophic yeast cells are known in the art. See, for example, *Pichia* Protocols, *Methods In Molecular Biology*, 389, Cregg, Ed., 2007, $2^{nd}$ Ed., Humana Press, Inc. Under some circumstances, it may be desirable to introduce or add methanol to the culture media, although, as demonstrated herein, methanol is not required to obtain efficient expression at high levels of one or more polypeptides of interest. Under some circumstances (e.g., when one or more nucleic acids encoding enzyme(s) involved in an iron-co-factor biosynthesis are expressed), it may be desirable to supplement the culture media with iron or a pharmaceutically or metabolically acceptable (or GRAS) salt thereof.

*Pichia* strains are able to grow on methanol as the sole carbon source. Methanol utilization is initiated by the conversion of methanol to formaldehyde by the action of alcohol oxidase. The methylotrophic yeast, *Pichia pastoris*, contains two genes for alcohol oxidases, AOX1 and AOX2. Strains with reduced alcohol oxidase activity ("methanol utilization slow" or MutS strains) often produce more of a recombinant protein expressed from the AOX1 promoter than strains that do not have reduced alcohol oxidase activity. Strains mutated in both AOX genes and completely lacking alcohol oxidase activity cannot metabolize methanol, but can still be induced for expression from the AOX1 promoter by methanol. These strains retain the ability to use other carbon sources for growth, but still express heterologous proteins from the AOX1 promoter upon the addition of methanol. Because these strains do not metabolize methanol ("methanol utilization minus" or Mut-strains), much less methanol is required for induction of protein expression, and strains carrying these mutations avoid issues related to methanol feeding in large-scale fermentations. See, for example, Chiruvolu et al., 1997, Enzyme Microb. Technol., 21:277-83. It was determined herein that expression of LegH from the AOX1 promoter in Mut-strains greatly improved the LegH yield. Thus, a methylotrophic yeast having a mutation in both the AOX1 gene and the AOX2 gene can be used in the methods described herein.

The protein of interest, or a complex that includes one or more proteins of interest (e.g., heme-bound LegH, a dehydrin, a phytase, a protease a catalase, a lipase, a peroxidase, an amylase, a transglutaminase, an oxidoreductase, a transferase, a hydrolase, a lyase, an isomerase, a ligase, or an antibody) can be purified from the yeast cells. Methods of purifying polypeptides are known in the art. As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

As used herein, nucleic acids can include DNA and RNA, and includes nucleic acids that contain one or more nucleotide analogs or backbone modifications. A nucleic acid can be single stranded or double stranded, which usually depends upon its intended use. Also provided are nucleic acids and polypeptides that differ from a given sequence. Nucleic acids and polypeptides can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a given nucleic acid or polypeptide sequence.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule, thereby leading to changes in the amino acid sequence of the encoded polypeptide. For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5 (Suppl. 3):345-352), which provides frequency tables for amino acid substitutions), and a non-conservative substitution is one in which an amino acid residue is replaced with an amino acid residue that does not have a similar side chain. Nucleic acid and/or polypeptide sequences may be modified as described herein to improve one or more properties including, without limitation, increased expression (e.g., transcription and/or translation), tighter regulation, deregulation, loss of catabolite repression, modified specificity, secretion, thermostability, solvent stability, oxidative stability, protease resistance, catalytic activity, and/or color.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A construct or vector containing a nucleic acid (e.g., a nucleic acid that encodes a polypeptide) also is provided. Constructs or vectors, including expression constructs or vectors, are commercially available or can be produced by recombinant DNA techniques routine in the art. A construct or vector containing a nucleic acid can have expression elements operably linked to such a nucleic acid, and further can include sequences such as those encoding a selectable marker (e.g., an antibiotic resistance gene). A construct or vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6xHis tag, glutathione S-transferase (GST)) Expression elements include nucleic acid sequences that direct and regulate expression of nucleic acid coding sequences. One example of an expression element is a promoter sequence.

Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Methods are described herein that can be used to generate a strain that lacks sequences for selection (i.e., that lacks a selectable marker). These methods include using a circular plasmid DNA vector and a linear DNA sequence; the circular plasmid DNA vector contains a selection marker and an origin of DNA replication (also known as an autonomously replicating sequence (ARS)), and the linear DNA sequence contains sequences for integration into the Pichia genome by homologous recombination. The linear DNA molecule additionally can include nucleic acid sequences encoding one or more proteins of interest such as, without limitation, heme-bound LegH, a dehydrin, a phytase, a protease a catalase, a lipase, a peroxidase, an amylase, a transglutaminase, an oxidoreductase, a transferase, a hydrolase, a lyase, an isomerase, a ligase, one or more enzymes involved in the pathway for production of small molecules, such as ethanol, lactic acid, butanol, adipic acid or succinic acid, or an antibody against any such proteins.

Pichia cells can be transformed with both DNA molecules and the transformants selected by the presence of the selectable marker on the circular plasmid. Transformants then can be screened for integration of the linear DNA molecule into the genome using, for example, PCR. Once transformants with the correct integration of the marker-free linear DNA molecule are identified, the cells can be grown in the absence of selection for the circular plasmid. Because the marker-bearing plasmid is not stably maintained in the absence of selection, the plasmid is lost, often very quickly, after selection is relaxed. The resulting strain carries the integrated linear DNA in the absence of heterologous sequences for selection. Therefore, this approach can be used to construct Pichia strains that lack a selectable marker (e.g., a heterologous selection marker) with little to no impact on recombinant protein yield.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A. Materials and Methods

Example 1—Polymerase Chain Reaction

Genes of interest were amplified from genomic DNA or plasmid DNA templates using PHUSION® Hi-fidelity DNA polymerase (New England Biolabs). Briefly, 0.6 µM each of forward and reverse primers are incubated with 10-50 ng of template DNA and 400 µM of nucleotide mix in the presence of 1-2 U of PHUSION® DNA polymerase. The reaction conditions were as follows:

| 1 cycle | Initial Denaturation | 98° C. | 1 min |
|---|---|---|---|
| 25 cycles | Denaturation | 98° C. | 10 sec |
| | Annealing | | 20 sec |
| | Extension | 72° C. | 30 sec per kb |
| 1 cycle | Final Extension | 72° C. | 5 min |
| 1 cycle | Hold | 4° C. | Forever |

Example 2—Plasmid Construction by Ligation 50-100 ng of restriction enzyme digested plasmid and 3× molar excess of PCR amplified inserts were incubated in the presence of T4 DNA ligase (New England Biolabs). Ligation was carried out at 16° C. for greater than 2 hr. 2 µl of ligation reaction was transformed into DH10B electrocompetent E. coli cells Example 3—Transformation into E. coli ElectroMax DH10B T1 Phage-Resistant Competent Cells 1.5-2 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV using a 1 mm gap cuvette (BioRad, Cat #165-2089); after a pulse 1 ml SOC was added to cells and cells were incubated at 37° C. for 1 h with shaking at 200 rpm. 10 µl of recovery mixture was plated on LB agar plates containing ampicillin at a concentration of 100 µg/ml. Plates were incubated overnight at 37° C.

Example 4—Linearization of Plasmid DNA for Transformation into P. pastoris

Plasmid DNA was digested with either PmeI restriction endonuclease (New England BioLabs, Cat # R0560L) in 1× CUTSMART® Buffer for 1-4 hours at 37° C. or SfiI restriction endonuclease in 1× CUTSMART® Buffer for 1-4 hours at 50° C. (New England BioLabs, Cat # R0123L). Linearized plasmid was gel purified from a 0.8% agarose gel using ZYMOCLEAN™ Gel DNA Recovery Kit (Zymo Research, Cat # D4002). DNA was eluted in 20 µl H₂O.

Example 5—Preparation of *P. pastoris* Transformation-Competent Cells

Selected strains of *P. pastoris* were grown to mid-exponential growth phase (~2 OD) in 25 ml YPD medium. Cells were collected by centrifugation at 930×g for 15 minutes. The cell pellet was resuspended in 2 ml of a solution of 80% YPD and 200 mM HEPES, pH 6.8. 75 µl of 1 M DTT was added. The resuspended cell pellet was mixed at 100 rpm at 30° C. for 25 minutes. A 40 ml volume of ice cold, sterile water was added to the suspension, and the cells were collected by centrifugation at 1125×g for 15 minutes and placed on ice. The cell pellet was resuspended in 40 ml ice cold water and collected as before for two additional wash steps. The cell pellet was then resuspended in 20 ml of ice cold 1 M sorbitol and collected by centrifugation as before. The final cell pellet was suspended in 0.3 ml ice cold, sterile sorbitol, aliquoted and frozen at −80° C.

Example 6—Transformation into *P. pastoris*

30-100 ng of linearized plasmid DNA was transformed into 30 µl of electrocompetent *P. pastoris* cells using a 1 mm gap GenePulser cuvette (BioRad) with a GenePulser (Bio-Rad) set at 1.15 kV. 1 ml of YPD/1M sorbitol was added and mixed at a 1:1 ratio to the cells. The cells were allowed to recover for 3 h at 30° C. with shaking at 100 rpm. 100 µl of the recovery mixture was plated on a YPD plate containing the appropriate antibiotic, and the rest of the cells were plated on a YPD plate with the appropriate antibiotic. Plates were incubated at 30° C. for 48 hours. Primary transformation plates were streaked onto YPD plates with appropriate antibiotic, and plates were incubated for 48 h at 30° C. Individual clones were patched onto YPD plates with antibiotics and the patches were used to do colony PCR or gDNA prep to confirm integration into the chromosome and to grow the strains in shake flasks for further analysis.

Example 7—Growing Cultures in Shake Flasks for Production of LegH

A strain from a fresh patch was inoculated into growth media BMGY (BMY supplemented with 0.75% glycerol) and grown overnight at 30° C. with shaking at 200 rpm. The next day, expression of LegH was induced with methanol by diluting the ON culture with BMMY media (BMY+1% methanol) supplemented with 0.1 mM Ammonium Fe(III) citrate. The culture was grown to an OD600 of 0.5-0.7. Antifoam was added to a final concentration of 0.01%. The cultures were grown for 72 hours total; cultures were supplemented with methanol every 24 hours by adding ⅒ of shake flask volume of 10×BMMY media (BMY+10% methanol). Cells were harvested after 72 h of induced growth by centrifugation.

Example 8—Shake Flask Medium

BMY media was prepared by dissolving 10 g of yeast extract and 20 g soytone in 790 ml water. The mixture was sterilized by autoclaving, and cooled to room temperature. 100 ml 1 M Potassium Phosphate buffer (pH 6.0) and 100 ml 10× Yeast Nitrogen Base without amino acids (13.4 g of YNB powder per 100 mL; Sigma-Aldrich) was filter sterilized (0.2 µm pore size PES) and added to the media. No pH adjustment is required.

| BMY Media Components | |
|---|---|
| Component | Amount, per 1 L |
| Yeast Extract | 10 g |
| Soy peptone (BD) | 20 g |
| Yeast Nitrogen Base without amino acids, 10X solution | 100 mL (results in 13.4 g/L in BMY) |
| 1M Potassium Phosphate Buffer, pH 6.0 | 100 mL |

The following components were dissolved in water, and autoclaved to sterilize.

| Low-Osmolarity Medium for Shake Flask | |
|---|---|
| Component | Amount, g/L |
| Ammonium Sulfate | 15.7 |
| Potassium Phosphate Monobasic | 9.4 |
| Calcium Sulfate Dihydrate | 0.43 |
| Magnesium Sulfate Heptahydrate | 11.7 |
| Sodium Citrate Dihydrate | 1.13 |

Example 9—Fermentation Medium and Feeds

The components indicated below were dissolved and the volume adjusted with water. The components were FCC food grade or equivalent. The medium was sterilized by autoclaving, by steaming in place, or with an equivalent.

| Low-Osmolarity Medium with 95 g/L Glycerol for Fermentation | |
|---|---|
| Component | Amount, g/L |
| Ammonium Sulfate | 15.7 |
| Potassium Phosphate Monobasic | 9.4 |
| Calcium Sulfate Dihydrate | 0.43 |
| Magnesium Sulfate Heptahydrate | 11.7 |
| Sodium Citrate Dihydrate | 1.13 |
| Glycerol, USP grade 99.7% | 95 |

After sterilization, the medium was allowed to cool down to room temperature, and the following was added:

| Component | Amount, mL/L |
|---|---|
| Trace Metals PTM1 Solution | 2 |
| Vitamin Solution | 4 |
| Sigma 204 antifoam or equivalent | 1 |

Trace metals PTM1 solution is available as a powdered mix from Sunrise Science (Cat No. 4052-A-B-1L). Pouch A and pouch B were mixed in 950 mL water, and 5 mL sulfuric acid was added. Some precipitation is expected upon mixing; the mixture was filter sterilized (0.2 µm pore size PES) and stored at 4° C. in the dark.

| Vitamin solution recipe | |
|---|---|
| Component | Amount, g/L |
| biotin | 0.2 |
| calcium pantothenate | 1 |

-continued

| Vitamin solution recipe | |
|---|---|
| Component | Amount, g/L |
| folic acid | 0.2 |
| inositol | 1 |
| niacin | 0.2 |
| p-aminobenzoic acid | 0.2 |
| Pyridoxine hydrochloride | 1 |
| riboflavin | 0.5 |
| thiamine hydrochloride | 1 |
| B12 | 0.1 |

Alternatively, trace metals PTM1 can be made as follows:

| Component | Amount |
|---|---|
| Cupric sulfate - 5H2O | 6.0 g |
| Sodium iodide | 0.08 g |
| Manganese sulfate - H2O | 3.0 g |
| Sodium molybdate - 2H2O | 0.2 g |
| Boric acid | 0.02 g |
| Cobalt chloride | 0.5 g |
| Zinc chloride | 0.5 g |
| Ferrous sulfate - 7H2O | 65.0 g |
| Biotin | 0.2 g |
| Sulfuric acid | 5.0 ml |
| Water | To a final volume of 1 L |

The components are mixed together, filter sterilized and stored at room temperature. The glycerol feed mix was prepared by mixing 17.5 g of AmberFerm 4000 into 320 mL water and stirring to dissolve. The water-Amberferm mixture was added to 850 g of glycerol and mixed well by vigorous stirring. The feed mix was sterilized by autoclaving.

| Glycerol feed solution | |
|---|---|
| Component | Amount, g/L |
| USP grade glycerol | 850 |
| Water | 320 |
| Sensient AmberFerm4000 soy hydrolysate | 17.5 |

The methanol feed was made using 99-100% methanol supplemented with 12 mL/L of PTM1 solution.

Example 10—Protocol for Lab-Scale High Oxygen Transfer Fermentation

Seed Shake Flask Protocol

In a aseptic biosafety hood, low-osmolarity medium and BMY were mixed in a 9:1 low-osmo:BMY ratio. Glycerol, at a concentration of 12.5 g/L, was added to the medium. USP food grade glycerol/glycerin (99.7% purity in a 50% v/v (63% w/w) glycerol/water solution) was used and autoclaved to sterilize. Sigma 204 or an equivalent antifoam was added to the medium at a concentration of 0.25 mL/L. Glycerol seed vials were retrieved, sprayed outside with 70% IPA or ethanol and thawed inside a biosafety hood at room temperature for about 5 min. Baffled shake flasks were inoculated with glycerol seed vials; 1 mL of inoculum vial were used for every 1 L of shake flask medium. Cultures were grown at 30° C. for 24 hours with shaking (200 RPM with a 1" throw). A ratio of between 1:10 and 1:5 of actual medium volume:nominal shake flask volume was used. 2.8 L nominal volume flask with 250 to 500 mL of medium were routinely use with success. The OD at 600 nm was measured after 24 hours of growth; if the OD was 15 or higher, the culture was used to inoculate a fermenter. If the OD was less than 15, the culture was grown for 1-2 more hours before the OD was determined again. If an OD of 15 was not reached after 15 to 30 hours, the seed flask was considered to have failed.

Fermentation Protocol

The fermentation medium and feeds were prepared as described herein. The initial volume should be about 40% of the maximum fermenter volume, e.g., 4 L, if the maximum working volume of the fermenter is 10 L. This is because the process will approach the maximum working volume by the end of the fermentation. The fermenter is inoculated with shake flask seed at 10% inoculum-fermenter ratio, e.g. if 4 L of initial media are present in the fermenter, the fermenter is inoculated with about 0.4 L of shake flask seed. The total volume in the fermenter at this point is referred to T0 volume, e.g. 4.4 L in this representative example. Process controls include the following: 30° C. temperature; dissolved oxygen controlled by agitation-aeration cascade to maintain a 20% saturation set point; and pH controlled via addition of 28% $NH_4OH$, the set point will depend on the phase of the process.

Batch phase (from inoculation to depletion of glycerol, signaled by DO spike): Depending on the responsiveness of the PID control for dissolved oxygen, a strong DO spike or a fast drop in agitation-aeration rates or a combination of both may be observed when the cells deplete the glycerol present in the medium. Fed-batch phase is initiated when this occurs. The duration of the batch phase is approximately 20 hours, but up to 24 hours is considered acceptable. The pH set point is 5.0. The wet cell weight at the end of the batch phase will be approximately 220 g/L.

Fed-batch phase: glycerol feed is initiated to achieve 12-14 g/L/hr of neat glycerol based on T0 volume. The federate was maintained until approximately 350 g/L wet cell weight was reached, which should take about 7-10 hours. The pH set point is 5.0.

Transition phase: A sample is taken before beginning the transition phase. Methanol feed was initiated to achieve 1 g/L/hr of neat methanol, based on the T0 volume, until 1-2 g/L methanol concentration was reached in the fermentation broth. The methanol feed rate was adjusted during the remainder of fermentation so as to maintain a methanol concentration of 0.25-1 g/L in broth. Glycerol federate was reduced from 12-14 g/L/hr to 8-9 g/L/hr of neat glycerol, based on T0 volume, linearly over the course of 2 hours. Stepwise reduction in feed rate every 20 min would be acceptable as well. The pH set point was changed to 3.5, and the fermentation was allowed to naturally adjust to the new set point (i.e., with no addition of acid).

Production phase (from end of glycerol feed ramp-down to end of fermentation): The pH set point was 3.5. A methanol concentration of 0.25-1 g/L was maintained in the fermentation broth. The feed rate of the glycerol was maintained at 8-9 g/L/hr of neat glycerol, based on the T0 volume. Samples were taken approximately every 12 hours. Samples were spun at 4000 to 7000 RCF at 4° C., and the supernatant decanted. The supernatant was saved in a separate tube. Pellets and 3 samples of 5 mL of supernatants at each time point were frozen at −80° C. If a 15-20% DO during production is unable to be maintained, even at maximum aeration and agitation rates for the vessel, the glycerol feed rate can be lowered up to 5 g/L/hr of neat glycerol, based on the T0 volume. Fermentation ended 60 hours after inoculation. At 1000 L scale, the harvest process consisted of shutting down feeds and aeration, chilling the broth to 8° C., and concentrating the paste using a sharples or disk stack centrifuge. Harvesting usually takes about 5-10 hours and does not incur a detectable loss of quality of the product. For lab scale, it is sufficient to collect, in addition to the 3×5 mL samples, an additional 50 mL sample at the end. Wet cell weight was >450 g/L, and spun pellets looked pink, as opposed to spun pellets from pre-induction samples, which looked more white. The color change of the broth from white to a more pronounced pink started following about 6-12 hours of induction.

Part B. Construction of Production Strains

Production Strain MXY0183

Example 11—Cloning Each Enzyme of Heme Biosynthesis Pathway into pGAN or pGAZ Integration Vector pGAN (with the nat selection marker) and pGAZ (with the ZEOCIN™ selection marker) were purchased from Biogrammatics, Inc (Carlsbad, Calif.). Each gene was placed under control of the AOX1 promoter, and the FDH terminator was placed immediately after the stop codon of each gene. The genes in the heme biosynthesis pathway were PCR amplified from wild type P. pastoris strain or subcloned from previous constructs.

The heme biosynthetic pathway, including the enzymes involved in the biosynthesis of heme, are shown in FIG. 1. The intermediates produced during the biosynthesis of heme are shown in the boxes, and the enzyme catalyzing each step is shown to the right. The rate limiting enzymatic steps, as shown in S. cerevisiae, are shown with underlining.

ALA synthase, ALA dehydratase, UPGIII synthase, UPGIII decarboxylase, CPG oxidase and PPG oxidase genes were PCR amplified with primers containing sites for recognition by the restriction endonuclease, BsaI. Oligonucleotides were synthesized by ElimBiopharm.

PHUSION® High-Fidelity DNA Polymerase (New England BioLabs, Cat # M0530L) was used to amplify genes from genomic DNA. PCR products were obtained and purified using DNA Clean&Concentrator-5 (Cat # D4004) and DNA was eluted in 25 µl of $H_2O$. Vector DNA, pGAZ and pGAN, and PCR products were digested with BsaI (New England BioLabs, Cat # R0535S) in 50 µl reaction volume at 37° C.

Linearized vectors and digested PCR products were purified from 0.8% agarose gel using ZYMOCLEAN™ Gel DNA Recovery Kit (Zymo Research Cat # D4002). DNA was eluted in 20 µl $H_2O$. Ligation reactions were set up in 10 µl at 16° C. overnight using T4 DNA Ligase (New England BioLabs, Cat # M0202S).

PBD and ferrochelatase genes were subcloned from previously constructed plasmids: pJAZ_PBD was digested with BstBI(Bsp119I) (ThermoScientific, FD0124) and NotI (ThermoScientific, FD0596) in 1× Fast Digest buffer for 5 min at 37° C. pJAZ_Ferroch was digested with MfeI (MunI, ThermoScientific, FD0753) and NotI (ThermoScientific, FD0596) in 1× Fast Digest buffer for 5 min at 37° C.

Digested products were purified from 0.8% agarose gel using ZYMOCLEA™ Gel DNA Recovery Kit (Zymo Research Cat # D4002). DNA was eluted in 20 µl $H_2O$.

Ligation reactions were set up in 10 µl reaction at 16° C. overnight using T4 DNA Ligase (New England BioLabs, Cat # M0202S).

1.5 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV; cells were incubated at 37° C. in 1 ml SOC for 1 h with shaking at 200 rpm. 10 µl of recovery mixture was plated on LB agar plates containing ampicillin at concentration 100 µg/ml. Plates were incubated overnight at 37° C. Colonies were screened by colony PCR for the presence of the insert. The sequences of the genes were confirmed.

| Designation | Construct | Gene |
|---|---|---|
| pMx0308 | pGAN-ALAsynth | ALA synthase |
| pMx0309 | pGAN-ALAD | ALAD |

| Primer Designation | Gene | Sequence | SEQ ID NO: |
|---|---|---|---|
| Mx00187 | ALAsynth_F | GAGGGTCTCGGATGGAGTTTGTCGCCCGTC | 19 |
| Mx00188 | ALAsynth_R | GAGGGTCTCGATTACAATCTGACTCCTGATGAGG | 20 |
| Mx00189 | ALAdehyd_F | GAGGGTCTCGGATGGTGCATAAGGCTGAATACTTG | 21 |
| Mx00190 | ALAdehyd_R | GAGGGTCTCGATTATTCAGATAACCACTCCAGG | 22 |
| Mx00191 | UroporSynth_F | GAGGGTCTCGGATGCCAAAAGCCATTCTTCTGAAG | 23 |
| Mx00192 | UroporSynth_R | GAGGGTCTCGATTAGTGCACTTTTTGTATAGAC | 24 |
| Mx00193 | UroporDecarb_F | GAGGGTCTCGGATGAGTAGATTTCCAGAACTGAAG | 25 |
| Mx00194 | UroporDecarb_R | GAGGGTCTCGATTATTGAGATCCAATGCG | 26 |
| Mx00195 | CoproOx_F | GAGGGTCTCGGATGGCCATCGACTCTGATATC | 27 |
| Mx00196 | CoproOx_R | GAGGGTCTCGATTATACCCATTCAATAGGAT | 28 |
| Mx00197 | ProtoporOx_F | GAGGGTCTCGGATGCTGAAAAGTCTTGCACCAAA | 29 |
| Mx00198 | ProtoporOx_R | GAGGGTCTCGATTAAATGCCACTGAGGGTAGC | 30 |

| Designation | Construct | Gene |
|---|---|---|
| pMx0310 | pGAN-UPGIIIsyn | Uroporphyrinogen synthase |
| pMx0311 | pGAN-UPGIIIdecarb | Uroporphyrinogen decarboxylase |
| pMx0312 | pGAN-CPGoxi | CPG oxidase |
| pMx0313 | pGAN-PPGoxi | Protoporphyrin oxidase |
| pMx0314 | pGAZ-ALAsyn | ALA synthase |
| pMx0315 | pGAZ-ALAD | ALAD |
| pMx0316 | pGAZ-UPGIIIsyn | Uroporphyrinogen synthase |
| pMx0317 | pGAZ-UPGIIIdecarboxilase | UPGIII decarboxilase |
| pMx0318 | pGAZ-PPGoxidase | PPG oxidase |
| pMx0319 | pGAZ-CPG oxidase | CPG oxidase |
| pMx0320 | pGAN-PBD | PBD |
| pMx0321 | pGAZ-PGC | PBD |
| pMx0322 | pGAZ-Fc | Ferrochelatase |
| pMx0323 | pGAN-Fc | Ferrochelatase |

Example 12—Assembling Heme Biosynthesis Genes on Plasmids for Integration into *P. pastoris* mutS Genome The whole cassette "promoter-gene-terminator" was PCR amplified with primers containing sites for restriction endonucleases to assemble plasmids for integration into the *Pichia* genome.

Assembling Paox1_UPS_FDHterm-Paox1_UPD_FDH term-Paox1_CPO_FDH Term. On pGAN Plasmid (pMx327)

pGAN-CPGoxidase (pMx312) was used as a vector to clone the UPS and UPD cassettes. UPG III synthase cassette was PCR amplified from pMx310 with primers to AOX1 promoter/FDH1 terminator containing NheI and SphI recognition sites for restriction endonucleases correspondingly:

PHUSION® High-Fidelity DNA Polymerase (New England BioLabs, Cat # M0530L) was used to amplify DNA from plasmids.

Obtained PCR products were purified using DNA Clean&Concentrator-5 (Zymo Research, Cat # D4004) and DNA was eluted in 25 µl of $H_2O$.

pGAN-CPGoxidase (pMx312) designated as a vector was digested in 1× CUTSMART® Buffer with NheI-HF (New England BioLabs, Cat # R3131S) and AgeI-HF (New England BioLabs, Cat # R3552S) over night at 37° C.

UPG III synthase cassette PCR product was digested in 1× CUTSMART® Buffer with NheI-HF (New England BioLabs, Cat # R3131S) and SphI-HF (New England BioLabs, Cat # R3182S) over night at 37° C.

UPG III decarboxylase cassette PCR product was digested in 1× CUTSMART® Buffer with SphI-HF (New England BioLabs, Cat # R3182S) and AgeI-HF (New England BioLabs, Cat # R3552S) over night at 37° C.

Digested vector and PCR products were gel purified from 0.8% agarose using ZYMOCLEAN™ Gel DNA Recovery Kit (Zymo Research, Cat # D4002). DNA was eluted in 20 µl $H_2O$.

Three way ligation between UPG III synthase cassette digested with NheI-SphI, UPG III decarboxylase cassette digested with SphI-AgeI and a vector digested with NheI-AgeI was set up in 10 µl at 16° C. overnight using T4 DNA Ligase (New England BioLabs, Cat # M0202S).

1.5 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV; cells were incubated at 37° C. in 1 ml SOC for 1 h with shaking at 200 rpm. 10 µl of recovery mixture was plated on LB agar plates containing ampicillin at a concentration of 100 µg/ml. Plates were incubated overnight at 37° C. Colonies were screened by colony PCR for the presence of the insert. The sequences of the junctions between vector and inserts were confirmed.

Assembling Paox1_ALAsynthase_FDH1term.-Paox1_PPGoxidase_FDH1term-Paox1_Fc_FDH1term.-Paox1_PBD_FDH1term Cassette (pMx330)

| Primer Designation | Recognition Sites | Sequence | SEQ ID NO: |
|---|---|---|---|
| Mx00399 | NheI-pAOX1-F | CAA TCG CTA GCA TCC AAC ATC CAA AGA CGA AAG G | 31 |
| Mx00401 | SphI-FDH1-R | GGA TAG CAT GCA CCT TAT CAA GAT AGC TAG AAA TAG AAA TGG | 32 |

UPG III decarboxylase cassette was PCR amplified from pMx311 with primers to AOX1 promoter/FDH1 terminator containing SphI and AgeI recognition sites for restriction endonucleases correspondingly:

a. PCR Amplification of Gene-Cassettes:

ALAsynthase cassette was PCR amplified from pMx310 with primers to AOX1 promoter/FDH1 terminator containing NheI and XhoI recognition sites for restriction endonucleases correspondingly:

| Primer Designation | Recognition Sites | Sequence | SEQ ID NO: |
|---|---|---|---|
| Mx00402 | SphI-pAOX1I-F | CAA TAG CAT GCA ACA TCC AAA GAC GAA AGG TTG AAT G | 33 |
| Mx00404 | AgeI-FDH1-R | CAT GGT ACC GGT ACC TTA TCA AGA TAG CTA GAA ATA GAA ATGG | 34 |

| Primer Designation | Recognition Sites | Sequence | SEQ ID NO: |
|---|---|---|---|
| Mx00399 | NheI-pAOX1-F | CAA TCG CTA GCA TCC AAC ATC CAA AGA CGA AAG G | 35 |
| Mx00400 | XhoI-FDH1-R | GAT ATT GCT CGA GAC CTT ATC AAG ATA GCT AGA AAT AGA AAT G | 36 |

PPGoxidase cassette was PCR amplified from pMx313 with primers to AOX1 promoter/FDH1 terminator containing XhoI and AflII recognition sites for restriction endonucleases correspondingly:

| Primer Designation | Recognition Sites | Sequence | SEQ ID NO: |
|---|---|---|---|
| Mx00403 | XhoI-pAOX1-F | CAA TCT CGA GAA CAT CCA AAG ACG AAA GGT TG | 37 |
| Mx00437 | AflII-FDH1-R | CAA CCA TTT CTA TTT CTA GCT ATC TTG ATA AGG TCT TAA GTC CA | 38 |

Ferrochelatase cassette was PCR amplified from pMx323 with primers to AOX1 promoter/FDH1 terminator containing AflII and AgeI recognition sites for restriction endonucleases correspondingly:

| Primer Designation | Recognition Sites | Sequence | SEQ ID NO: |
|---|---|---|---|
| Mx00404 | AgeI-FDH1-R | CAT GGT ACC GGT ACC TTA TCA AGA TAG CTA GAA ATA GAA ATG G | 39 |
| Mx00436 | AflII-pAOX1-F | TTA CTT AAG TCC AAC ATC CAA AGA CGA AAG GTT G | 40 |

G418 marker was PCR amplified from pJAG plasmid purchased from Biogrammatics using the following primers:

| Primer Designation | Recognition Sites | Sequence | SEQ ID NO: |
|---|---|---|---|
| Mx00438 | MluI-G418-F | TCA CAG ACG CGT TGA ATT GTC C | 41 |
| Mx00439 | BbvCI-G418-R | TTG CTC CTC AGC TTA GAA GAA CTC GTC AAG AAG GCG ATA CAA GTG | 42 |

PHUSION® High-Fidelity DNA Polymerase (New England BioLabs, Cat # M0530L) was used to amplify DNA from plasmids. The PCR products were obtained and purified using DNA Clean&Concentrator-5 (Zymo Research, Cat # D4004) and DNA was eluted in 25 μl of H₂O.

b. Preparation of Vectors pGAZ-PBD (pMx321) designated as a vector was digested in 1× CUTSMART® Buffer with NheI-HF (New England BioLabs, Cat # R3131S) and XhoI (New England BioLabs, Cat # R0146S) overnight at 37° C.

pGAZ-ALAsyn.-PBD (pMx328) was digested in 1× NEBuffer3.1 with MluI (New England BioLabs, Cat # R0198S) and BbvCI (New England BioLabs, Cat # R0601S) overnight at 37° C.

pGAG-ALAsyn-PBD (pMx332) was digested in 1× CUTSMART® Buffer with XhoI (New England BioLabs, Cat # R0146S) and AgeI-HF (New England BioLabs, Cat # R3552S) overnight at 37° C.

c. Making Intermediate Constructs and Assembling a Final Cassette

Digested vector and PCR products were gel purified from 0.8% agarose using Gel DNA Recovery Kit (Zymo Research, Cat # D4002). DNA was eluted in 20 μl of H₂O.

pGAZ-PBD (pMx321) vector, digested with NheI-XhoI restriction endonucleases, was ligated with ALAsynthase cassette PCR product digested with the same enzymes in 10 μl reaction at 16° C. overnight using T4 DNA Ligase (New England BioLabs, Cat # M0202S) to yield a pGAZ-ALAsyn.-PBD plasmid (pMx328).

pGAG-ALAsyn-PBD (pMx332) digested with XhoI and AgeI-HF restriction endonucleases was ligated with PPGoxidase cassette and Ferrochelatase cassette PCR products digested with XhoI, AflII and AflII, AgeI-HF restriction endonucleases correspondingly in a three way ligation reaction using T4 DNA Ligase (New England BioLabs, Cat # M0202S) to yield a pGAG-ALAsynthase_PPGoxidase_Fc_PBD (pMx330).

Figure 2:
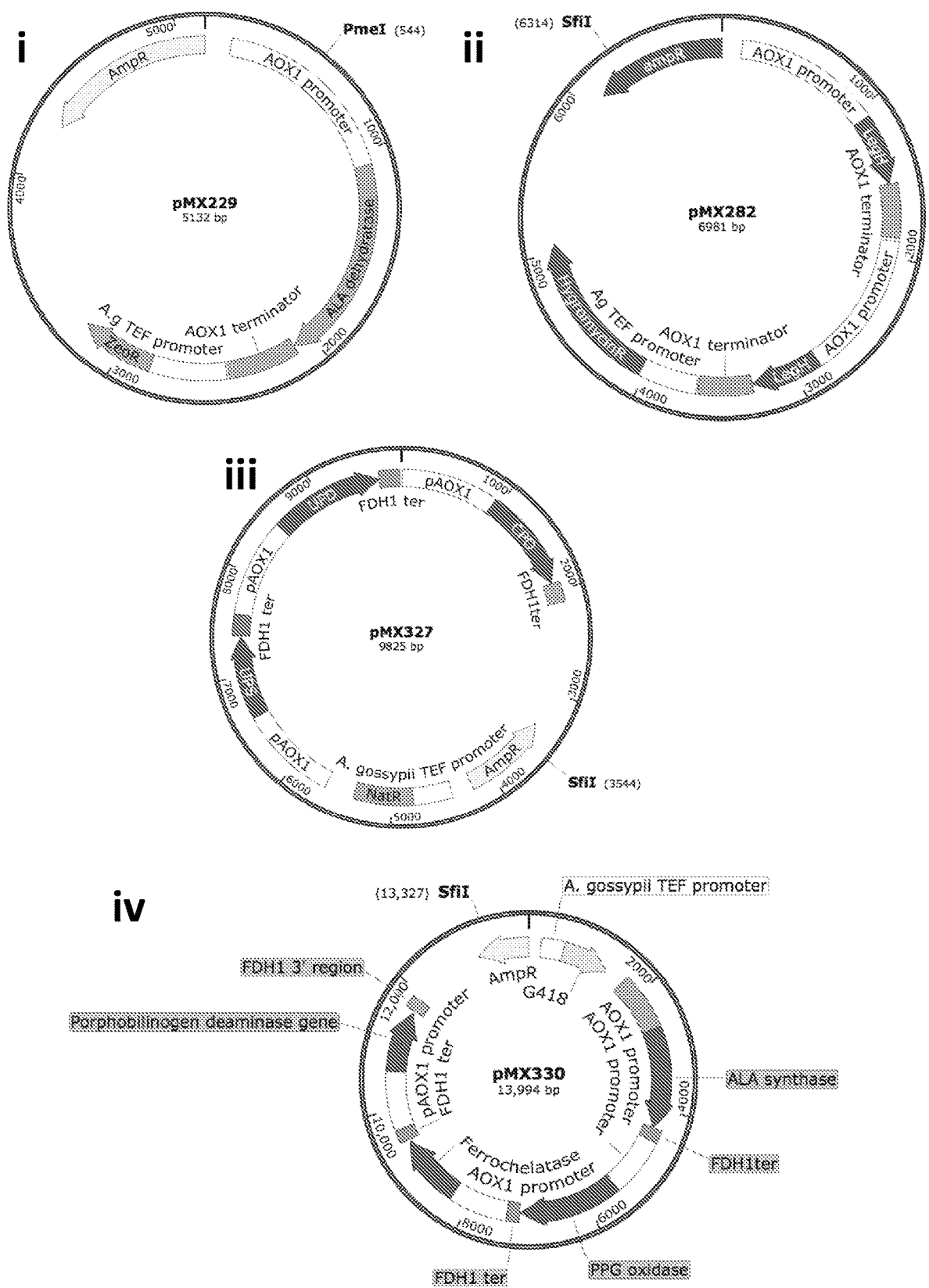
FIG. 2 are schematics of plasmids used in the construction of production strain MXY0183.
Figure 3:
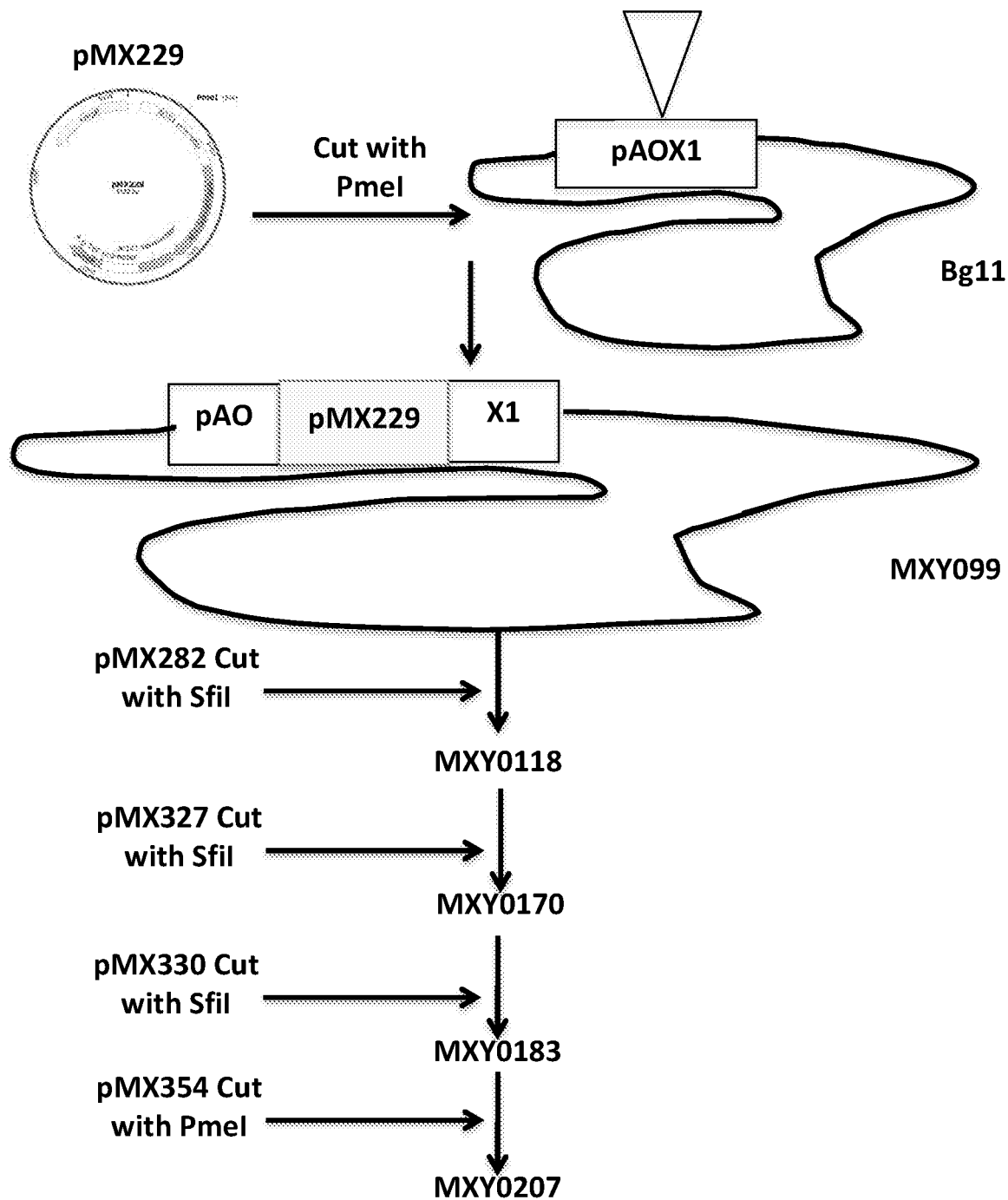
FIG. 3 is a schematic showing the generation of the production strains, MXY0183 and MXY0207, from the parent strain, Bg11.

1.5 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV; cells were incubated at 37° C. in 1 ml SOC for 1 h with shaking at 200 rpm. 10 µl of recovery mixture was plated on LB agar plates containing ampicillin at a concentration of 100 µg/ml. Plates were incubated overnight at 37° C. Colonies were screened by colony PCR for the presence of the insert. The sequences of junctions between the vector and the inserts were confirmed.

deaminase (PBD) (the enzymes catalyzing steps 1, 7, 8 and 3, respectively) from the *P. pastoris* genome were assembled on plasmid pMX330 (FIG. 2*iv* and FIG. 3). pMX330 was linearized with the SfiI restriction endonuclease and transformed into MXY0170, leading to the generation of strain MXY0183 (FIG. 3). The genotype of MXY0183 was confirmed using PCR and qPCR.

Production Strain MXY0207

Example 14—Construction of pGAB Expression Vector

The pGAB expression vector (FIG. 4A) was constructed by replacing the open reading frame of the ZEOCIN™

| Designation | Construct | Gene |
|---|---|---|
| pMx0327 | pGAN-UPGsyn_UPGdecarb_CPGoxy | UPGsyn_UPGdecarb_CPGoxy |
| pMx0328 | pGAZ-ALAsyn-PGC | ALAsyn-PBD |
| pMx0330 | pGAG-ALAsyn_PBD_PPG_Fc | ALAsyn_PBD_PPG_Fc |
| pMx0332 | pGAG-ALAsyn_PBD | G418 marker |

Example 13—Integration of Linearized Plasmids with Gene Cassettes into *P. pastoris* Bgl11 Genome The plasmids that were used to generate the production strain, MXY0183, are shown in FIG. 2. The steps taken to make the modifications that led to production strain, MXY0183, are depicted in FIG. 3.

The first enzyme to be introduced into the *P. pastoris* Bgl11 genome was ALAD. A plasmid containing pAOX1-driven ALAD (pMX229, FIG. 2*i* and FIG. 3) was linearized using PmeI restriction enzyme (New England BioLab). Linearized plasmid was purified from 0.8% agarose gel as described and transformed into *P. pastoris* using homologous recombination at the native AOX1 locus, generating strain MXY099 (FIG. 3).

A plasmid containing two copies of the soybean LegH gene (sequence optimized for *P. pastoris*; SEQ ID NO:3) under the control of the pAOX1 promoter designated pMX282 (FIG. 2*ii* and FIG. 3) was linearized using SfiI restriction enzyme. Linearized plasmid was purified from a 0.8% agarose gel as described and transformed into the *P. pastoris* strain containing ALAD, generating the strain MXY0118 (FIG. 3). qPCR was used and determined that strain MXY0118 contained several copies of the LegH gene, likely due to concatamerization of the plasmid, pMX282, at the time of recombination.

Plasmid pMX327 (FIG. 2*iii* and FIG. 3) containing genes encoding Uroporphyrinogen III synthase (UPS), Uroporphyrinogen III decarboxylase (UPD) and Coproporphyrinogen III oxidase (CPO) (the enzymes catalyzing steps 4, 5 and 6, respectively) under control of the AOX1 promoter was linearized with the SfiI restriction endonuclease and introduced into MXY0118, yielding strain MXY0170 (FIG. 3).

Genes encoding ALA synthase (ALAS), Protoporphyrin III oxidase (PPO), Ferrochelatase (FC) and Porphobilinogen resistance gene in the pGAZ vector (BioGrammatics, Inc., Carlsbad, Calif.) with the open reading frame from the Blasticidin S deaminase (BSD) gene from *Aspergillus terreus*, which allows for selection of transformants carrying the plasmid with the antibiotic Blasticidin S.

The BSD open reading frame was amplified from a commercially synthesized DNA molecule using oligonucleotide primers MxO0476 and MxO0477 using a high fidelity polymerase chain reaction as described herein.

| Primer Designation | Description | Sequence | SEQ ID NO: |
|---|---|---|---|
| MxO0477 | BSD Reverse | TTA GTC TTG CTC CTC AGC TTA GCC | 43 |
| MxO0476 | BSD Forward | TCA CAG ACG CGT TGA ATT GTC C | 44 |

The BSD PCR product was purified by gel electrophoresis on a 1% agarose gel in 1×TBE buffer (89 mM Tris, 89 mM boric acid, 2 mM EDTA, pH 8.3) and visualized using SYBR™ Safe DNA gel stain (Life Technologies, Carlsbad, Calif.). The desired DNA fragment was excised from the agarose gel and the DNA was recovered using the ZYMOCLEAN™ Gel DNA Recovery Kit (Zymo Research, Irvine, Calif.).

The purified BSD PCR product and pGAZ vector were digested with 10 units each of the MluI and BbvCI restriction endonucleases (New England Biolabs, Ipswich, Mass.) for 1 hour at 37° C. in 1× NEBuffer 3.1 (100 mM NaCl, 50 mM Tris-HCl, 10 mM MgCl$_2$, 100 µg/ml BSA, pH 7.9 @ 25° C.). Digested DNA products were recovered by gel electrophoresis as described above.

The purified, MluI and BbvCI digested BSD product and pGAZ vector were incubated with 400 units of T4 DNA ligase (New England Biolabs) in 1×T4 DNA ligase reaction buffer (50 mM Tris-HCl, 10 mM MgCl$_2$, 1 mM ATP, 10 mM DTT, pH 7.5 @ 25° C.) in a 20 µl reaction, at 16° C. for 2 hours in a 20 µl reaction. Electrocompetent *E. coli* DH10B cells were transformed with 2 µl of the ligation reaction and antibiotic resistant transformants were selected on LSB agar plates supplemented with 100 μg/μl ampicillin.

Example 15—Construction of Mxr1 Expression Vector

Figure 4:
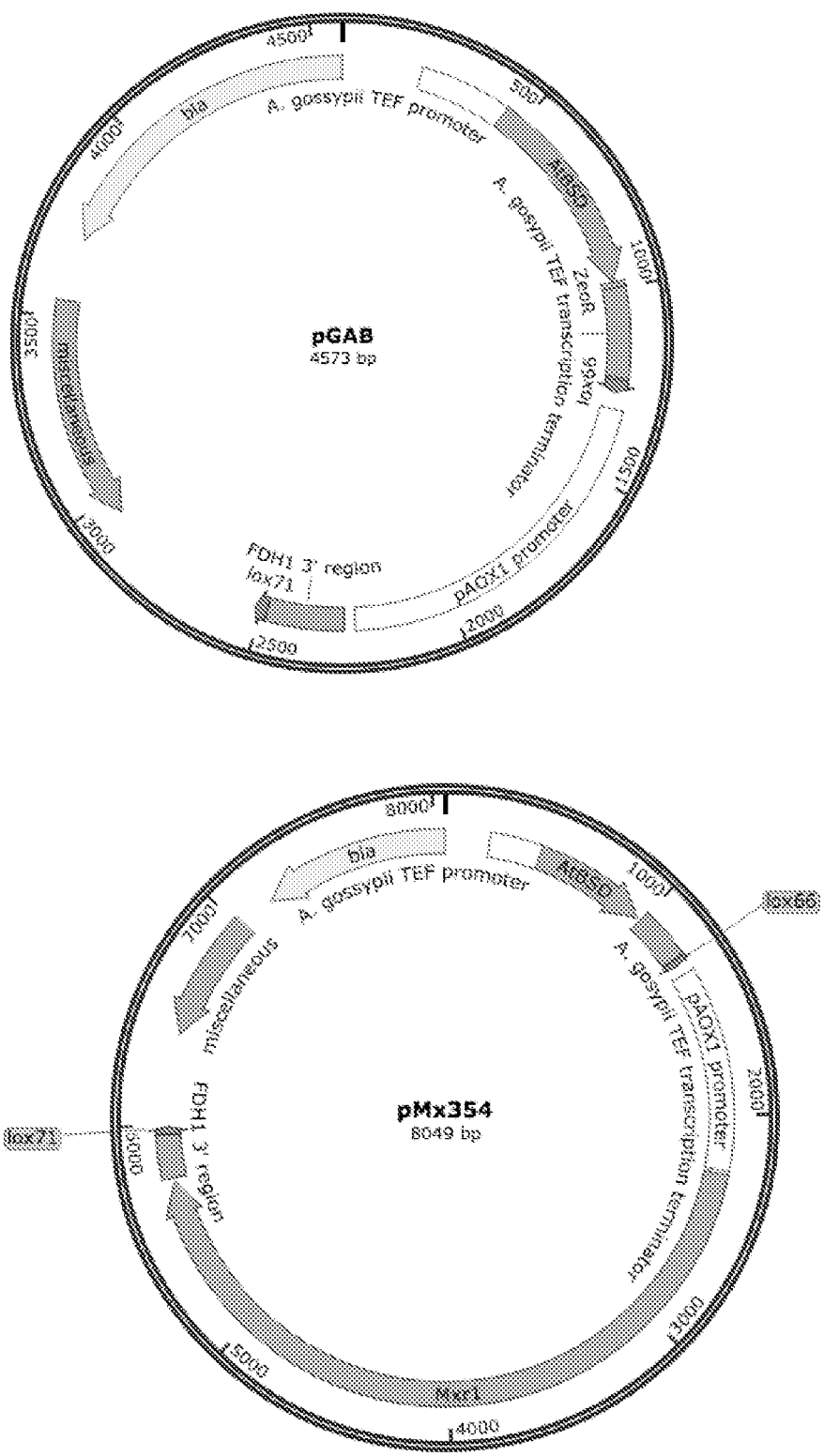
FIG. 4 are schematics showing plasmids pGAB and pMx354.

The Mxr1 expression vector, pMx354, was constructed by introducing the Mxr1 open reading frame into the pGAB vector (FIG. 4B). The Mxr1 open reading frame was inserted into pGAB with the translation start immediately downstream of the methanol-inducible alcohol oxidase 1 (AOX1) promoter from *Pichia pastoris* and the translation stop signal immediately followed by the transcription terminator sequence from the *P. pastoris* FDH1 gene.

The open reading frame encoding the Mxr1 protein was amplified from genomic DNA isolated from *Pichia pastoris* strain Bg11 MutS obtained from BioGrammatics, Inc. (Carlsbad, Calif.). The Mxr1 open reading frame was amplified from *P. pastoris* genomic DNA with primers MxO0495 (TTT TGC GGC CGC ATG AGC AAT CTA CCC CCA ACT TTT G (SEQ ID NO:45)) and MxO0496 (AAA AGC GGC CGC CTA GAC ACC ACC ATC TAG TCG GTT (SEQ ID NO:46)), which appended flanking NotI restriction endonuclease recognition sites. Amplification was accomplished using the polymerase chain reaction as described herein.

The amplified Mxr1 PCR product and the pGAB vector were digested with 10 units of NotI restriction endonuclease (New England Biolabs) for 1 hour at 37° C. in 1× NEBuffer 3.1 (100 mM NaCl, 50 mM Tris-HCl, 10 mM MgCl$_2$, 100 m/ml BSA, pH 7.9 @ 25° C.). Following digestion, the NotI-digested pMx352 vector was treated with 5 units Antarctic phosphatase (New England Biolabs) for 15 minutes at 37° C. in 1× Antarctic phosphatase buffer (50 mM Bis-Tris-Propane-HCl, 1 mM MgCl$_2$, 0.1 mM ZnCl$_2$, pH 6 @ 25° C.).

The NotI-digested amplified Mxr1 fragment and pMx352 vector were separated by electrophoresis on a 1% agarose gel in 1× TBE buffer (89 mM Tris, 89 mM boric acid, 2 mM EDTA, pH 8.3) and visualized using SYBR™ Safe DNA gel stain (Life Technologies, Carlsbad, Calif.). The desired DNA fragments were excised from the agarose gel and the DNA was recovered using the ZYMOCLEAN™ Gel DNA Recovery Kit (Zymo Research, Irvine, Calif.).

The NotI-digested fragment containing Mxr1 open reading frame was introduced into pGAB at a NotI site immediately downstream of the AOX1 promoter by ligation. A mixture containing 137 ng of NotI-digested DNA encoding the Mxr1 open reading frame and 60 ng of NotI-digested, phosphatase-treated pMx352 was incubate with 400 units of T4 DNA ligase (New England Biolabs) in 1×T4 DNA ligase reaction buffer (50 mM Tris-HCl, 10 mM MgCl$_2$, 1 mM ATP, 10 mM DTT, pH 7.5 @ 25° C.) in a 20 μl reaction, at 16° C., for 2 hours in a 20 μl reaction. Electrocompetent *E. coli* DH10B cells were transformed with 2 μl of the ligation reaction and antibiotic resistant transformants were selected on LSB agar plates supplemented with 100 μg/μl ampicillin. Plates were incubated overnight at 37° C. Colonies were screened for the presence of the insert by PCR using primers MxO0495 and MxO0496. The sequence of the final vector was confirmed by DNA sequencing.

During cloning, 6 additional amino acids were introduced at the N-terminus of Mxr1. The Mxr1 open reading frame is shown under the section "Nucleic acid sequences", with residual amino acids from the cloning shown with underlining. *Pichia* production strains containing the Mxr1 sequence having the additional 6-amino acids at the N-terminus and *Pichia* strains containing the wild type Mxr1 (i.e., without the additional 6 amino acids at the N-terminus) were indistinguishable in fermentation tanks.

Example 16—Construction of Native Mxr1 Expression Vector

A plasmid containing the Mxr1 transcription regulator gene under the control of the pAOX1 promoter, designated pMX354, was used as a template for PCR amplification. The 3' end of the AOX1 promoter, the LegH open reading frame, and the AOX1 terminator were amplified from pMX354 using primers MxO0617 and MxO0647 shown below. The AOX1 terminator, linker and the 5' end of the AOX1 promoter were amplified from pMX382 using primers MxO0618 and MxO0646.

| Primer Designation | Sequence | SEQ ID NO: |
|---|---|---|
| MxO0646 | ACTAGATGGTGGTGTCTAGTCAAGAGGATGTCAGAATGCCATTTG | 47 |
| MxO0647 | TCTGACATCCTCTTGACTAGACACCACCATCTAGTCGGTTTTCTAG | 48 |

PCR products were obtained and purified using DNA Clean&Concentrator-5 and DNA was eluted in 12 μl of H$_2$O. The purified PCR products were then combined and used as a template for a subsequent round of PCR amplification using primers MxO0617 and MxO0618. The resulting PCR product was composed of the 3' end of the AOX1 promoter, followed by the Mxr1 open reading frame, the AOX1 terminator, a short linker sequence, and the 5' end of the AOX1 promoter. The PCR product was obtained and purified as described herein. The purified PCR product was cloned into the pCR™-Blunt II-TOPO® vector using the Zero Blunt® TOPO® PCR Cloning Kit (Invitrogen, Cat # K2800-20) to create the pMX402 vector.

Example 17—Construction of *P. pastoris* Strains MXY0206 and MXY0207

The pMx354 Mxr1 expression vector (FIG. 4B) was introduced into the MXY0183 strain by DNA transformation (FIG. 3).

The pMx354 vector (1.5 μg) was linearized at a unique PmeI site in the AOX1 promoter sequences by digestion with 20 units of the PmeI restriction endonuclease (New England Biolabs) for 1 hour at 37° C. in 1×NEBuffer 4 (50 mM Potassium Acetate, 20 mM Tris-acetate, 10 mM Magnesium Acetate, 1 mM DTT, pH 7.9@25° C.).

The PmeI-digested pMX354 vector was purified by gel electrophoresis recovered using the ZYMOCLEAN™ Gel DNA Recovery Kit as described above. The linearized pMX354 vector was introduced into strain MXY0183 by transformation and selection on blasticidin-containing medium. Two independent clones were obtained from the transformation, and they were designated MXY0206 and MXY0207. The presence of an additional copy of Mxr1 under the control of the AOX1 promoter in these strains was confirmed by PCR.

Production Strain MXY0291

Example 18—Construction of Strains MXY0213 and MXY0260

Figure 5:
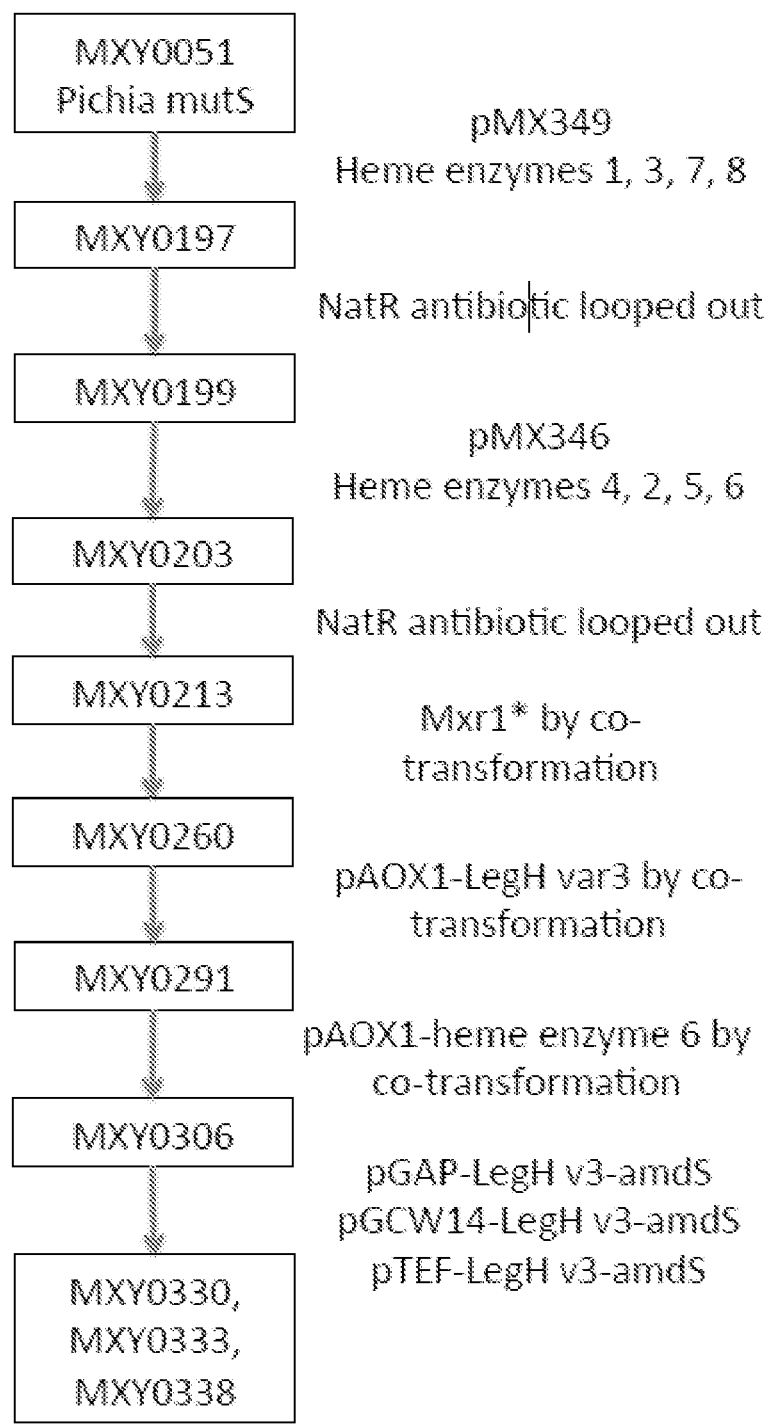
FIG. 5 is a schematic showing the generation of the antibiotic selection free production strains, MXY0291 and MXY0338, from the parent strain, Bg11.
Figure 6:
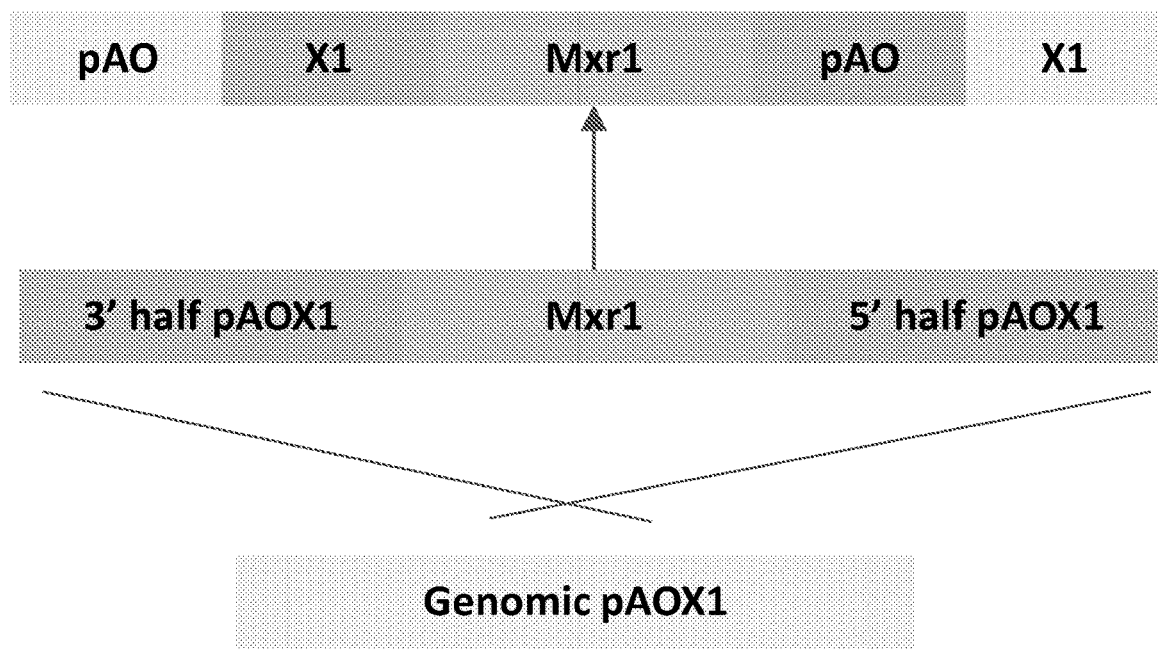
FIG. 6 is a schematic of the linear pieces of DNA containing Mxr1 and LegH var 3 that were introduced by co-transformation to make the production strain MXY0291.
Figure 6:
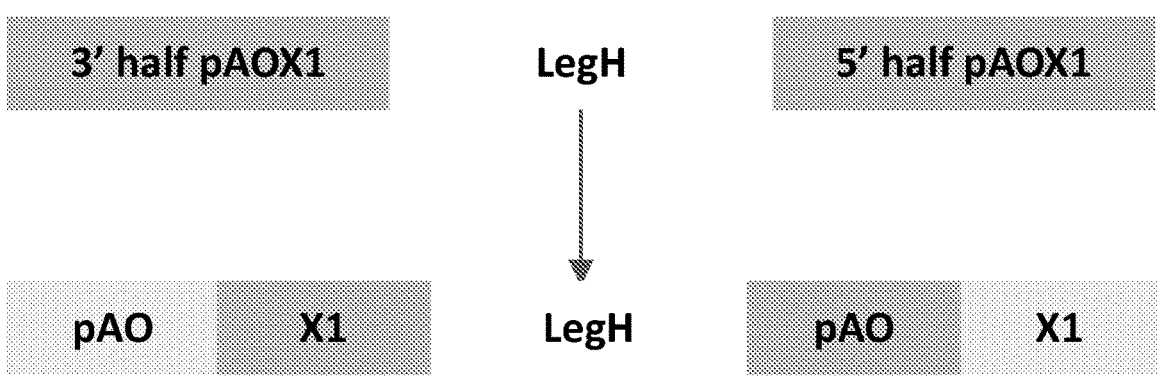

FIG. 5 shows the steps taken to construct antibiotic marker free strain MXY0213 that contains 7 enzymes of the heme biosynthetic pathway. A linear piece of DNA containing variant Mxr1 (6 extra amino acids at N terminus) under pAOX1, with homology to the pAOX1 promoter on each end, was introduced using co-transformation (FIG. 5 and FIG. 6i). This linear Mxr1 expression cassette was simultaneously introduced into Pichia strain MXY213 with the pIL75 plasmid by transformation. The pIL75 vector carries a panARS autonomous replication sequence (Liachko & Dunham, 2014, FEMS Yeast Res., 14:364-7), which allows for maintenance of the plasmid vector without integration into the genome of the transformed cells, and a kanMX marker for selection of transformants with the antibiotic G418. Transformed cells were selected on media supplemented with G418 for the presence of kanMX marker on the pIL75 plasmid. Pichia transformants were screened by colony PCR for transformants that took up both the pIL75 plasmid and had correctly integrated the Mxr1 expression cassette.

Example 19—Co-Transformation to Introduce the LegH Expression Cassette into Pichia A plasmid containing a different Pichia pastoris-codon optimized variant of soybean LegH gene (variant 3; SEQ ID NO:5) under the control of the pAOX1 promoter designated pMX399 was used as a source of template for PCR amplification of the gene. The backbone from TOPO cloning plasmid pMX401 was PCR amplified. The insert and vector were assembled using GIBSON ASSEMBLY® (NEB GIBSON ASSEMBLY® kit) to generate plasmid pMX422. This plasmid was used as a template for a subsequent round of PCR amplification using primers MxO0617 and MxO0618 shown below.

| Primer Designation | Sequence | SEQ ID NO: |
|---|---|---|
| MxO0617 | AAACGCTGTCTTGGAACCTAATATGAC | 49 |
| MxO0618 | AAACTGTCAGTTTTGGGCCATTTG | 50 |

The resulting PCR product was composed of, in the 5' to 3' direction, the 3' end of the AOX1 promoter, followed by the LegH var 3 open reading frame, the AOX1 terminator, a short linker sequence, and the 5' end of the AOX1 promoter (FIG. 6ii). The PCR product was obtained and purified by agarose gel electrophoresis as described herein.

Transformants with LegH expression cassette integrated into the genome were screened by PCR and characterized for LegH gene copy number using qPCR.

Example 20—Curing Transformants of Plasmid Vectors Bearing Selection Markers In clones where the soybean LegH expression cassette was shown to be correctly integrated by colony PCR and in high copy number by qPCR, the pIL75 plasmid required for selection on G418 was eliminated by relaxing selection for the antibiotic. Transformants were streaked out for single colonies on media lacking G418 antibiotic. Because the panARS plasmid is not stably maintained in the absence of selection, the pIL75 was rapidly lost from the transformed cells under this condition. The resulting Pichia strain, MXY0291, contains sequences for LegH expression in copy number similar to MXY0207, but lacks heterologous sequences for selection.

Production Strains MXY0330, MXY0333, and MXY0338

Example 21—Construction of Strain MXY0306

Genotype PCR of strain MXY0291 revealed that a portion of the CPGoxidase coding sequence had been deleted during construction of this strain. The full-length CPGoxidase coding region was restored by replacement of the truncated copy. Briefly, a linear DNA fragment containing the pAOX1 promoter and full-length CPGoxidase coding region was generated by PCR amplification from plasmid pMX312 using primers MxO0866 and MxO0867 shown below.

| Primer Designation | Sequence | SEQ ID NO: |
|---|---|---|
| MxO0866 | ACGCTGTCTTGGAACCTAATATGAC | 51 |
| MxO0867 | TACCCATTCAATAGGATTTTGTAGTACCTGC | 52 |

The linear pAOX1-CPGoxidase DNA fragment was introduced into strain MXY0291 by co-transformation with the pIL75 plasmid. Transformants were selected on media containing G418 and then screened for the presence of the full-length CPGoxidase coding region by PCR. An isolate containing the full-length CPGoxidase was identified and subsequently cured of the plasmid vector required for selection on G418 as described above. This strain was designated MXY0306 (see FIG. 5).

Example 22—Linear Constructs for Hybrid Promoter Strains

Figure 7:
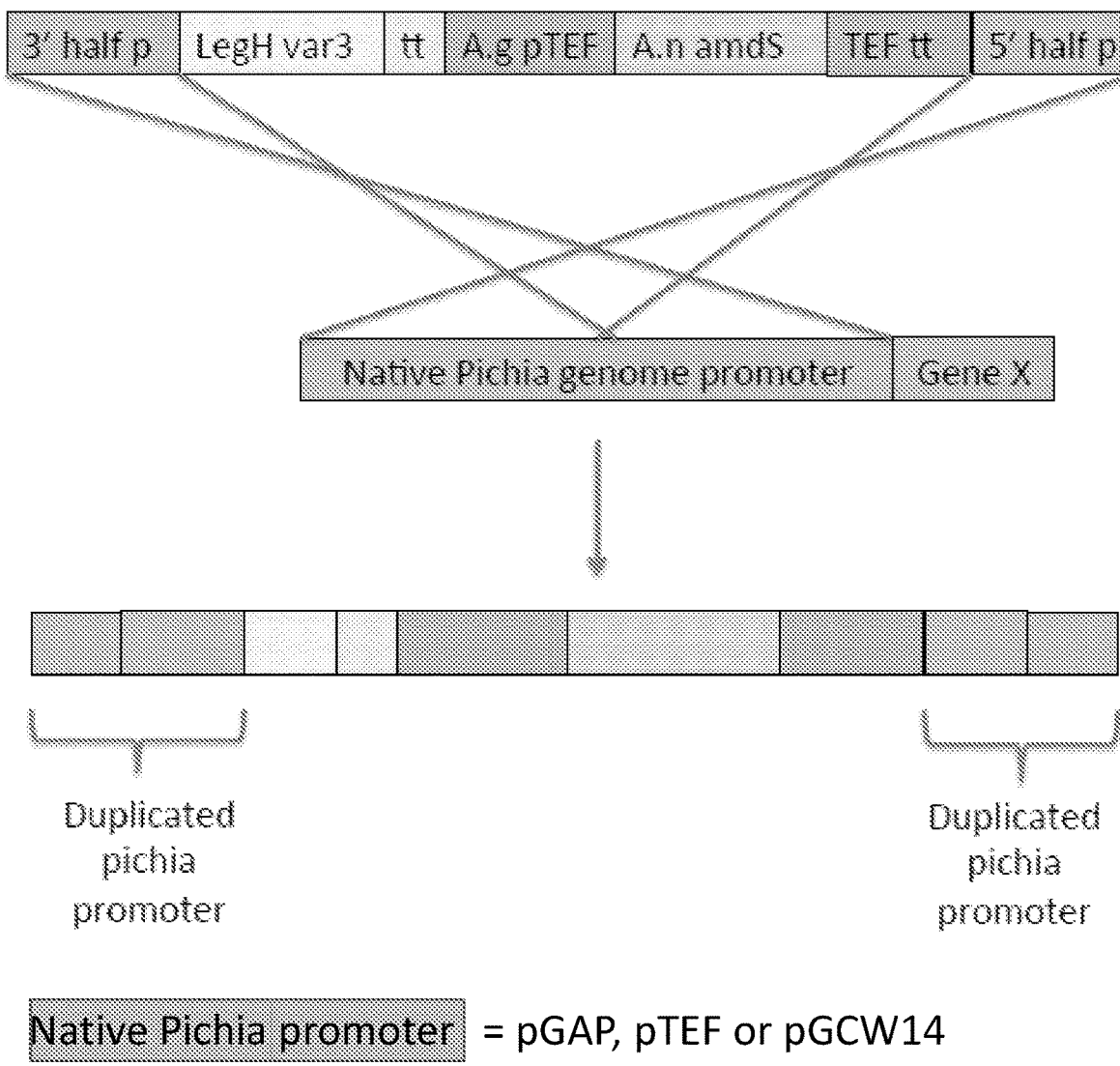
FIG. 7 is a schematic showing the linear construct expressing LegH under control of native *Pichia* non-pAOX1 constitutive promoters.

LegH variant 3 was expressed under the direction of each of the three native Pichia pastoris constitutive promoters indicated herein. The linear constructs are shown in FIG. 7, and contained the 3' half of the promoter, followed by LegH var3, followed by the FDH1 transcription terminator. This was immediately followed by the antibiotic resistance cassette containing the pTEF promoter from Ashbya gossypii, the acetamidase gene (amdS) from Aspergillus nidulans and the TEF terminator from Ashbya gossypii. Finally, the construct contained the 5' half of the promoter. This linear cassette was amplified using the oligonucleotide primers listed in the Table below to generate constructs that contain several hundred base pairs on the 5' and 3' ends that are homologous to the respective promoter in the native Pichia genome.

Primers Used to Amplify the Linear Constructs

| Primer designation | Sequence | SEQ ID NO: |
|---|---|---|
| MXO0718 | GAGCTTCTTCTACGGCCCCC | 53 |
| MXO0723 | TCCAGCAGAGTAAAATTTCCTAGGGAC | 54 |
| MXO0724 | CTCTTTTAGGTTTTAAGTTGTGGGAACAGTAACA | 55 |
| MXO0729 | GTGGGTGCTTCTTTGCGTGG | 56 |
| MXO0730 | AGAATTGCCATCAAGAGACTCAGGACT | 57 |
| MXO0735 | GATAGAGAGAAATCGCAAACTTTGAGAGGAAG | 58 |

Competent MXY0306 cells were transformed with each of the linear cassettes and transformants containing the amdS selection cassette were selected based on their ability to grow on agar plates containing acetamide as the sole nitrogen source. These strains were purified, isolated and the presence of LegH under control of the constitutive promoter was verified by PCR (FIG. 5).

Example 23—Nucleic Acid Sequences

Mxr1 nucleic acid sequence (the underlined nucleotides encode 6 amino acid at N-term introduced during cloning)
(SEQ ID NO: 1)
ATGCGAGACCGCGGCCGCATGAGCAATCTACCCCCAACTTTTGGTTCCAC

TAGACAATCTCCAGAAGACCAATCACCTCCCGTGCCCAAGGAGCTGTCAT

TCAATGGGACCACACCCTCAGGAAAGCTACGCTTATTTGTCTGTCAGACA

TGTACTCGAGCATTTGCTCGTCAGGAACACTTGAAACGACACGAAAGGTC

TCACACCAAGGAGAAACCTTTCAGCTGCGGCATTTGTTCTCGTAAATTCA

GCCGTCGAGATCTGTTATTGAGACATGCCCAAAAACTGCACAGCAACTGC

TCTGATGCGGCCATAACAAGACTAAGGCGCAAGGCAACTCGTCGGTCTTC

TAATGCCGCGGGTTCCATATCTGGTTCTACTCCGGTGACAACGCCAAATA

CTATGGGTACGCCCGAAGATGGCGAGAAACGAAAAGTTCAGAAACTGGCC

GGCCGCCGGGACTCAAATGAACAGAAACTGCAACTGCAACAACAACATCT

ACAGCAACAACCACAGTTGCAATACCAACAATCTCTTAAGCAGCATGAAA

ATCAAGTCCAGCAGCCTGATCAAGATCCATTGATATCCCCGAGAATGCAA

TTATTCAATGATTCCAACCATCACGTAAACAATTTGTTTGATCTTGGACT

AAGAAGAGCTTCCTTCTCCGCCGTTAGTGGAAATAATTATGCCCATTATG

TGAATAATTTTCAACAAGATGCCTCTTCTACCAATCCAAATCAAGATTCA

AATAATGCCGAATTTGAGAATATTGAATTTTCTACCCCACAAATGATGCC

CGTTGAAGATGCTGAAACTTGGATGAACAACATGGGTCCAATTCCGAACT

TCTCTCTCGATGTGAACAGGAACATTGGTGATAGCTTTACAGATATACAA

CACAAGAATTCAGAGCCTATTATATCCGAACCGCCCAAGGACACCGCTCC

AAACGACAAGAAGTTGAATGGCTACTCTTTTTACGAAGCCCCCATCAAGC

CATTAGAATCCCTATTTTCTGTCAGGAATACAAAGAGAAACAAGTATAAA

ACAAATGACGACTCTCCAGACACCGTGGATAATAACTCCGCACCGGCTGC

-continued

TAATACCATTCAAGAACTTGAGTCTTCTTTGAATGCATCCAAGAATTTTT

GCTTGCCAACTGGTTATTCCTTCTATGGTAATTTGGACCAACAGACTTTC

TCTAACACGTTATCATGCACTTCTTCTAATGCCACAATTTCGCCCATTCT

ACTCGATAACTCCATTAATAATAACTCCACTAGTGACGTGAGACCAGAAT

TTAGAACACAAAGTGTCACCTCTGAAATGAGTCAAGCCCCTCCCCCTCCT

CAAAAAAACAACTCGAAATATTCCACCGAAGTTCTTTTTACCAGCAACAT

GCGGTCGTTTATTCACTACGCTCTTTCCAAGTATCCTTTTATTGGTGTGC

CCACTCCAACTCTTCCGGAGAACGAAAGACTAAATGAATATGCTGATTCA

TTCACCAACCGTTTCTTAAATCATTATCCTTTCATACATGTCACGATTCT

CAAAGAATACTCCCTTTTCAAGGCAATTTTAGATGAGAATGAGTCGACTA

AGAACTGGGAAAATAATCAGTTTTACTTAGAGAACCAACGAATATCAATT

GTTTGTCTTCCTCTTTTGGTGGCTACGATAGGTGCAGTACTATCAAACAA

CAAAAAGGATGCTTCGAATTTATACGAAGCTTCAAGGCGTTGTATTCATG

TTTACTTAGATTCCAGGAAAAAGATACCCACTTCCTTGTCCGCAAATAAC

AATGACTCTCCACTTTGGCTAATTCAATCCCTGACGTTATCTGTTATGTA

TGGGTTATTTGCGGACAATGACATTAGTTTGAATGTCGTGATCAGACAAG

TTAACGCACTTATTCTCTGGTCAAGACTTCGGGCCTGAATAGGACCTCAA

TTATAGATCTTTTCAACATCAACAAACCTTTGGATAATGAACTCTGGAAT

CAATTCGTGAAAATAGAGTCCACCGTAAGGACAATCCACACGATTTTTCA

AATCAGTTCCAACTTAAGCGCCTTGTACAATATTATTCCATCGTTGAAAA

TTGATGACCTAATGATTACTCTACCAGTTCCCACAACACTTTGGCAAGCT

GATTCTTTTGTGAAATTCAAAAGTCTAAGTTACGGAAATCAGATCCCTTT

TCAATATACAAGAGTACTACAGAATTTGATTGATTACAATCAGCCATTGA

GCGATGGAAAATTTTTGTATGAAAACCATGTAAGTGAGTTTGGACTCATA

TGCCTACAGAATGGTCTACACCAATACAGCTATTTCCAAAATTGACTGCT

GTCAATAACAGAGAAGATGCGCTATTCACAAAGGTTGTTAATTCACTTCA

CAGTTGGGATAGGATGATTTCGAATTCTGATTTGTTTCCAAAGAAGATAT

ATCAGCAGAGTTGCTTGATTTTGGACTCAAAGTTGCTTAATAATTTCCTG

ATTGTCAAGAGCTCATTGAAAGTTTCGACCGGAGACGTTAGTTCTTTGAA

TAAGTTAAAAGAAAACGTGTGGCTTAAAAACTGGAATCAAGTGTGTGCTA

```
TCTATTATAACAGCTTCATGAACATTCCTGCTCCCAGTATTCAAAAGAAG
TACAATGACATAGAGTTTGTGGATGACATGATTAATTTGAGTCTAATCAT
CATCAAGATTATGAAACTCATTTTCTATAACAATGTCAAAGACAATTATG
AGGATGAAAATGACTTCAAATTGCAAGAGTTAAATTTAACATTTGACAAT
TTTGATGAGAAAATATCCTTGAATTTGACAATATTATTCGATATATTTTT
GATGATCTACAAGATAATTACCAATTACGAAAAGTTTATGAAGATCAAAC
ACAAGTTTAATTACTACAATTCTAATTCGAATATAAGCTTCTTGCATCAT
TTCGAACTCTCCTCGGTTATCAATAACACCCAAATGAACCAGAATGATTA
TATGAAAACAGATATTGATGAAAAGCTTGATCAGCTTTTCCACATCTATC
AACATTTTTCCGGCTGTATCTGGATTTAGAAAAGTTTATGAAGTTCAAAT
TCAACTATCATGACTTTGAGACAGAGTTTTCAAGTCTCTCAATATCCAAT
ATACTGAACACTCATGCTGCTTCTAACAATGACACAAATGCTGCTGATGC
TATGAATGCCAAGGATGAAAAAATATCTCCCACAACTTTGAATAGCGTAT
TACTTGCTGATGAAGGAAATGAAAATTCCGGTCGTAATAACGATTCAGAC
CGCCTGTTCATGCTGAACGAGCTAATTAATTTTGAAGTAGGTTTGAAATT
TCTCAAGATAGGTGAGTCATTTTTTGATTTCTTGTATGAGAATAACTACA
AGTTCATCCACTTCAAAAACTTAAATGACGGAATGTTCCACATCAGGATA
TACCTAGAAAACCGACTAGATGGTGGTGTCTAG
```

Mxr1 protein sequence (the underlined 6 amino acid at N-term introduced during cloning)
(SEQ ID NO: 2)

<u>MRDRGR</u>MSNLPPTFGSTRQSPEDQSPPVPKELSFNGTTPSGKLRLFVCQT
CTRAFARQEHLKRHERSHTKEKPFSCGICSRKFSRRDLLLRHAQKLHSNC
SDAAITRLRRKATRRSSNAAGSISGSTPVTTPNTMGTPEDGEKRKVQKLA
GRRDSNEQKLQLQQQHLQQQPQLQYQQSLKQHENQVQQPDQDPLISPRMQ
LFNDSNHHVNNLFDLGLRRASFSAVSGNNYAHYVNNFQQDASSTNPNQDS
NNAEFENIEFSTPQMMPVEDAETWMNNMGPIPNFSLDVNRNIGDSFTDIQ
HKNSEPIISEPPKDTAPNDKKLNGYSFYEAPIKPLESLFSVRNTKRNKYK
TNDDSPDTVDNNSAPAANTIQELESSLNASKNFCLPTGYSFYGNLDQQTF
SNTLSCTSSNATISPILLDNSINNNSTSDVRPEFRTQSVTSEMSQAPPPP
QKNNSKYSTEVLFTSNMRSFIHYALSKYPFIGVPTPTLPENERLNEYADS
FTNRFLNHYPFIHVTILKEYSLFKAILDENESTKNWENNQFYLENQRISI
VCLPLLVATIGAVLSNNKKDASNLYEASRRCIHVYLDSRKKIPTSLSANN
NDSPLWLIQSLTLSVMYGLFADNDISLNVVIRQVNALNSLVKTSGLNRTS
IIDLFNINKPLDNELWNQFVKIESTVRTIHTIFQISSNLSALYNIIPSLK
IDDLMITLPVPTTLWQADSFVKFKSLSYGNQIPFQYTRVLQNLIDYNQPL
SDGKFLYENHVSEFGLICLQNGLHQYSYFQKLTAVNNREDALFTKVVNSL
HSWDRMISNSDLFPKKIYQQSCLILDSKLLNNFLIVKSSLKVSTGDVSSL
NKLKENVWLKNWNQVCAIYYNSFMNIPAPSIQKKYNDIEFVDDMINLSLI
IIKIMKLIFYNNVKDNYEDENDFKLQELNLTFDNFDEKISLNLTILFDIF
LMIYKIITNYEKFMKIKHKFNYYNSNSNISFLHHFELSSVINNTQMNQND
YMKTDIDEKLDQLFHIYQTFFRLYLDLEKFMKFKFNYHDFETEFSSLSIS
NILNTHAASNNDTNAADAMNAKDEKISPTTLNSVLLADEGNENSGRNNDS
DRLFMLNELINFEVGLKFLKIGESFFDFLYENNYKFIHFKNLNDGMFHIR
IYLENRLDGGV*

Pichia pastoris-Codon-optimized LegH nucleic acid sequence
(SEQ ID NO: 3)
```
ATGGGTGCTTTCACCGAGAAGCAGGAAGCACTTGTTTCCTCTTCGTTCGA
AGCTTTTAAGGCTAACATCCCTCAATACTCTGTTGTGTTTTACACGTCCA
TTCTAGAAAAAGCTCCTGCTGCCAAGGACCTCTTCTCTTTTCTGTCCAAC
GGTGTAGATCCATCCAATCCCAAATTAACAGGTCACGCTGAGAAATTGTT
CGGTTTAGTCAGAGATAGCGCTGGACAATTGAAAGCAAATGGTACTGTGG
TTGCTGATGCTGCCTTGGGCAGCATCCATGCACAGAAGGCAATTACAGAC
CCACAATTTGTTGTTGTGAAGGAAGCTCTGCTTAACTATAAAGGAAGCCG
TCGGAGACAAATGGAGTGACGAGTTGTCATCAGCTTGGGAGGTAGCTTAT
GATGAGTTGGCCGCAGCAATCAAAAAGGCATTCTAA
```

Pichia pastoris-Codon-optimized LegH amino acid sequence
(SEQ ID NO: 4)
MGAFTEKQEALVSSSFEAFKANIPQYSVVFYTSILEKAPAAKDLFSFLSN
GVDPSNPKLTGHAEKLFGLVRDSAGQLKANGTVVADAALGSIHAQKAITD
PQFVVVKEALLKTIKEAVGDKWSDELSSAWEVAYDELWIKKAF Pichia pastoris-Codon-optimized LegH variant 3 nucleic acid sequence
(SEQ ID NO: 5)
```
ATGGGTGCATTTACAGAAAAACAAGAGGCTTTAGTATCCTCATCTTTTGA
AGCTTTCAAAGCCAATATTCCTCAATACTCCGTTGTTTTCTATACGTCCA
TTTTGGAAAAGGCTCCAGCAGCTAAGGACCTTTTCTCTTTCTTGTCGAAC
GGCGTGGATCCCTCAAATCCTAAGCTGACTGGTCACGCCGAGAAGCTTTT
TGGTTTGGTCAGAGACAGCGCCGGACAGCTGAAAGCTAACGGTACAGTTG
TGGCAGATGCTGCCTTGGGATCTATACATGCACAAAAGGCTATCACCGAC
CCACAGTTTGTGGTTGTAAAAGAGGCTCTACTCAAAACTATCAAGGAAGC
AGTTGGTGACAAATGGAGCGATGAATTGTCCAGTGCATGGGAGGTCGCTT
ACGATGAGTTAGCTGCTGCAATCAAAAAGGCTTTCTAA
```

Pichia pastoris-Codon-optimized LegH variant 3 amino acid sequence
(SEQ ID NO: 6)
MGAFTEKQEALVSSSFEAFKANIPQYSVVFYTSILEKAPAAKDLFSFLSN
GVDPSNPKLTGHAEKLFGLVRDSAGQLKANGTVVADAALGSIHAQKAITD
PQFVVVKEALLKTIKEAVGDKWSDELSSAWEVAYDELAAAIKKAF Pichia pastoris pAOX1 promoter
(SEQ ID NO: 7)
```
GATCTAACATCCAAAGACGAAAGGTTGAATGAAACCTTTTTGCCATCCGA
CATCCACAGGTCCATTCTCACACATAAGTGCCAAACGCAACAGGAGGGGA
TACACTAGCAGCAGACCGTTGCAAACGCAGGACCTCCACTCCTCTTCTCC
TCAACACCCACTTTTGCCATCGAAAAACCAGCCCAGTTATTGGGCTTGAT
TGGAGCTCGCTCATTCCAATTCCTTCTATTAGGCTACTAACACCATGACT
TTATTAGCCTGTCTATCCTGGCCCCCCTGGCGAGGTTCATGTTTGTTTAT
TTCCGAATGCAACAAGCTCCGCATTACACCCGAACATCACTCCAGATGAG
```

GGCTTTCTGAGTGTGGGGTCAAATAGTTTCATGTTCCCCAAATGGCCCAA

AACTGACAGTTTAAACGCTGTCTTGGAACCTAATATGACAAAAGCGTGAT

CTCATCCAAGATGAACTAAGTTTGGTTCGTTGAAATGCTAACGGCCAGTT

GGTCAAAAGAAACTTCCAAAAGTCGGCATACCGTTTGTCTTGTTTGGTA

TTGATTGACGAATGCTCAAAAATAATCTCATTAATGCTTAGCGCAGTCTC

TCTATCGCTTCTGAACCCCGGTGCACCTGTGCCGAAACGCAAATGGGGAA

ACACCCGCTTTTTGGATGATTATGCATTGTCTCCACATTGTATGCTTCCA

AGATTCTGGTGGGAATACTGCTGATAGCCTAACGTTCATGATCAAAATTT

AACTGTTCTAACCCCTACTTGACAGCAATATATAAACAGAAGGAAGCTGC

CCTGTCTTAAACCTTTTTTTTTATCATCATTATTAGCTTACTTTCATAAT

TGCGACTGGTTCCAATTGACAAGCTTTTGATTTTAACGACTTTTAACGAC

AACTTGAGAAGATCAAAAAACAACTAATTATTCGAAACG

Pichia pastoris pGAP promoter
(SEQ ID NO: 8)
CGACTATTATCGATCAATGAAATCCATCAAGATTGAAATCTTAAAATTGC

CCCTTTCACTTGACAGGATCCTTTTTTGTAGAAATGTCTTGGTGTCCTCG

TCCAATCAGGTAGCCATCTCTGAAATATCTGGCTCCGTTGCAACTCCGAA

CGACCTGCTGGCAACGTAAAATTCTCCGGGGTAAAACTTAAATGTGGAGT

AATGGAACCAGAAACGTCTCTTCCCTTCTCTCTCCTTCCACCGCCCGTTA

CCGTCCCTAGGAAATTTTACTCTGCTGGAGAGCTTCTTCTACGGCCCCCT

TGCAGCAATGCTCTTCCCAGCATTACGTTGCGGGTAAAACGGAGGTCGTG

TACCCGACCTAGCAGCCCAGGGATGGAAAAGTCCCGGCCGTCGCTGGCAA

TAATAGCGGGCGGACGCATGTCATGAGATTATTGGAAACCACCAGAATCG

AATATAAAAGGCGAACACCTTTCCCAATTTTGGTTTCTCCTGACCCAAAG

ACTTTAAATTTAATTTATTTGTCCCTATTTCAATCAATTGAACAACTATC

AAAACACG

Pichia pastoris pGCW14 promoter
(SEQ ID NO: 9)
CAGGTGAACCCACCTAACTATTTTTAACTGGGATCCAGTGAGCTCGCTGG

GTGAAAGCCAACCATCTTTTGTTTCGGGGAACCGTGCTCGCCCCGTAAAG

TTAATTTTTTTTTCCCGCGCAGCTTTAATCTTTCGGCAGAGAAGGCGTTT

TCATCGTAGCGTGGGAACAGAATAATCAGTTCATGTGCTATACAGGCACA

TGGCAGCAGTCACTATTTTGCTTTTTAACCTTAAAGTCGTTCATCAATCA

TTAACTGACCAATCAGATTTTTTGCATTTGCCACTTATCTAAAAATACTT

TTGTATCTCGCAGATACGTTCAGTGGTTTCCAGGACAACACCCAAAAAAA

GGTATCAATGCCACTAGGCAGTCGGTTTTATTTTTGGTCACCCACGCAAA

GAAGCACCCACCTCTTTTAGGTTTTAAGTTGTGGGAACAGTAACACCGCC

TAGAGCTTCAGGAAAAACCAGTACCTGTGACCGCAATTCACCATGATGCA

GAATGTTAATTTAAACGAGTGCCAAATCAAGATTTCAACAGACAAATCAA

TCGATCCATAGTTACCCATTCCAGCCTTTTCGTCGTCGAGCCTGCTTCAT

TCCTGCCTCAGGTGCATAACTTTGCATGAAAAGTCCAGATTAGGGCAGAT

TTTGAGTTTAAAATAGGAAATATAAACAAATATACCGCGAAAAAGGTTTG

TTTATAGCTTTTCGCCTGGTGCCGTACGGTATAAATACATACTCTCCTCC

CCCCCCTGGTTCTCTTTTTCTTTTGTTACTTACATTTTACCGTTCCGTCA

CTCGCTTCACTCAACAACAAAA

Pichia pastoris pTEF1 promoter
(SEQ ID NO: 10)
ATAACTGTCGCCTCTTTTATCTGCCGCACTGCATGAGGTGTCCCCTTAGT

GGGAAAGAGTACTGAGCCAACCCTGGAGGACAGCAAGGGAAAAATACCTA

CAACTTGCTTCATAATGGTCGTAAAAACAATCCTTGTCGGATATAAGTGT

TGTAGACTGTCCCTTATCCTCTGCGATGTTCTTCCTCTCAAAGTTTGCGA

TTTCTCTCTATCAGAATTGCCATCAAGAGACTCAGGACTAATTTCGCAGT

CCCACACGCACTCGTACATGATTGGCTGAAATTTCCCTAAAGAATTTCTT

TTTCACGAAAATTTTTTTTTTACACAAGATTTTCAGCAGATATAAAATGG

AGAGCAGGACCTCCGCTGTGACTCTTCTTTTTTTTCTTTTATTCTCACTA

CATACATTTTAGTTATTCGCCAAC

Heme biosynthesis enzyme 1- ALA Synthase
(SEQ ID NO: 11)
ATGGAGTTTGTCGCCCGTCAGTCCATGAATGCCTGTCCCTTTGTCAGGTC

AACTTCTACCCACCATTTGAAGAAGTTGGCAGCAAACAGTTCTCTAGCTG

CTACTGCTAGTCATTGTCCCGTGGTTGGCCCTGCTCTCCAACAGCAGAGA

TACTACTCTCAACCTTCCAAGCCAGCCCAAGCCCAAACCTCCGACATTGC

TACTGGGATCAAGAAGGATGTTTCTCCGATCCGTATGGACTCTAATGAAA

CCGCCTTTGATTACAATGGAATGTATGAGTCTGATCTTGCGAATAAACGT

AAAGATAACTCGTATCGTTATTTCAATAACATCAACCGTCTAGCCAAGGA

GTTTCCCAAGGCACATCGCCAGACCGAAGATGACAAGGTGACCGTCTGGT

GCTCTAACGACTACTTAGGAATGGGTAGGCATCCTGAGATTATCAAAACC

ATGAAGGCTACCATGGACAAGTACGGTTCCGGAGCAGGAGGAACTAGGAA

CATTGCAGGTCATAACCACGCCGCTATCAATTTGGAAAGCGAGTTGGCTT

GCTTGAACAAGAAGGAAGCGGCTCTGGTGTTTTCATCATGTTTCATAGCT

AACGATGCAATCATCTCGTTGTTGGGACAAAAAATCAAAAATTTGGTCAT

TTTCTCTGACCAGTCGAATCATGCTTCCATGATATTGGGTGTGCGTAACT

CCAAAGCGAAGAAGCACATCTTCAAGCACAACAATTTGAAGGATCTGGAG

TCGCAGTTAGCTCAGTACCCCAAGTCGACTCCTAAACTGATCGCCTTCGA

GTCAGTTTACTCTATGTGTGGATCTGTGGCTCCCATTGAGAAGATTTGCG

ATTTGGCTAAAAGGTACGGTGCCCTCACCTTCTTGGATGAAGTTCATGCT

GTTGGAATGTATGGTCCTCATGGACAGGGTGTAGCTGAGCATTTGGACTT

TGATCTGCATTTACAGTCTGGAATCGCCAGTCCTAGCGTGGTGGACAAAC

GCACCATATTGGATCGTGTCGACATGATTACTGGTACTTGCGGAAAGTCA

TTTGGTACTGTTGGAGGTTACGTTGCTGGTAGTGCCAACCTAATTGATTG

GTTAAGATCCTATGCGCCAGGTTTCATTTTCACTACCACACTTCCTCCTG

CTATCATGGCTGGTACAGCCACTTCTGTTCGTATTGTTAGGGCCGACATT

GAGGCCCGTATCAAGCAACAGCTTAATACTCGCTACGTCAAAGACTCATT

TGAAAACCTTGGTATTCCAGTCATTCCAAACCCAAGTCACATTGTTCCTG

TTCTAGTTGGAATGCTGCAGATGCCAAGAAGGCATCCGATATGTTATGAA

CAAACACCGTATTTATGTTCAAGCTATTAACTACCCTACTGTGCCTGTCG

GTGAAGAACGACTAAGGATTACTCCTACTCCAGGTCATGGAAAGGAGATT

TGTGACCAGCTGATCAGCGCTGTCGACGATGTTTTTACTGAGCTTAATTT

ACCAAGAATCAACAAATGGCAGTCCCAAGGTGGTCATTGCGGTGTTGGTG

ATGCTAATTACGTACCAGAACCCAATCTGTGGACTCAGGACCAGCTCAGC

TTGACAAACCAAGACTTGCACTCCATGTGCACAACCCAGTGATTGAGCAG

ATCGAAACCTCATCAGGAGTCAGATTGTAG

Heme biosynthesis enzyme 2-ALA dehydratase
(SEQ ID NO: 12)
ATGGTGCATAAGGCTGAATACTTGGACGACCACCCAACTCAGATTTCCAG

CATTCTTTCAGGAGGTTACAACCACCCATTACTTCGTGAATGGCAACATG

AACGTCAACTCAACAAAAACATGTTCATCTTTCCCCTGTTTGTCACAGAT

CGACCAGACGAAGAAGAACTTATTCCTAGTCTACCTAATATCAAGAGGTT

TGGCGTTAACAAGTTGATTCCTTATGTAGGAGGTTTGGTTTCCAAAGGAT

TGAGGGCGGTGATCCTATTTGGTGTTCCTCTGAAGCCCGGTGTGAAAGAT

GAAGAAGGAACGGCCGCTGATGATCCAGAGGGACCTGTTATCCAAGCCAT

CAAACACTTGAGAAAGAACTTTCCTGACCTGTATATCATCACCGATGTCT

GTCTATGTGAGTACACCAGCCATGGACATTGTGGAATACTATATGAGGAT

GGCACTATCAACAGAGAGCTCTCAGTCCGTCGTATTGCTGCTGTAGCTGT

CAAATATGCTCAAGCTGGAGCCAACTCTGTGGCTCCTTCTGATATGACTG

ACGGCAGAATAAGAGATATTAAAGAAGGCTTACTAAGTGCAGGACTGGCA

CATAAAACGTTTGTTATGTCCTACGCTGCAAAATTCTCTGGTAATTTGTA

TGGCCCTTTCAGAGATGCTGCAGGTTCCTGTCCATCTCAAGGGGACAGAA

AATGTTACCAGCTTCCTTCTGGAGGAAAAGGGTTGGCCCATCGTGCTCTG

ATTCGTGATATGAATGAAGGCACTGATGGAATTATTGTCAAACCATCTAC

ATTCTATTTGGACATTGTCGCTGATGCTTATCAGCTTTGTAAAGACTATC

CTATCTGCTGTTACCAGGTTTCTGGAGAGTACGCCATGCTACATGCAGCG

GCAGAGAAGAATATTGTTGATCTGAAATCAATCGCTTTTGAAGCTCATCA

AGGATTCTTGCGGGCTGGAGCTCGTTTAATCATTAGTTACTTTACCCCTG

AATTCCTGGAGTGGTTATCTGAATGA

Heme biosynthesis enzyme 3-Porphobilinogen
deaminase
(SEQ ID NO: 13)
ATGAACCAAATCGAACAGAGCGGACCCATTGATTGCAGTTCCTTGAAATT

GGGGTCCCGAAAGTCCGCTCTGGCTATAATCCAGGCAGAAATCGTCCGCC

AATTGATATTGAAAGAATACCCTGAATTGGAGACGAAGTTGGTCAGTGTG

TCCACCCTGGGGGACCAAGTCCAGAATAAAGCACTTTTCACGTTTGGAGG

AAAATCTTTGTGGACCAAAGAACTTGAGATGTTGTTGTTGGAGAGTGTGG

GAGGATTTGACCAAATAGACATGATTGTACACTCGTTGAAAGACATGCCA

ACTCATTTACCAGACGAATTTGAGCTGGGTTGCATTATTGAAAGAGAAGA

CCCTAGAGACGCTTTGGTCGTGCAAGATGGTTTATCTTACAAGTCATTGG

CCGACCTTCAGAGGGAGCTGTGGTCGGTACGTCTTCGGTTAGAAGATCG

GCTCAACTACTGAAGAATTTCCCTCATCTGAAATTCAAATCTGTTAGAGG

AAACCTTCAGACCAGACTAAGAAAATTAGATGATCCAGATTCCGAGTACT

GCTGTCTCCTCCTTGCAGCAGCCGGTTTAATCAGGACAGGCTTACAACAC

AGAATTTCAATGTATTTGAACGACGATGTGATGTACCACTCCGTCGGACA

AGGAGCATTAGGAGTAGAGATCAGAAAAGGTGACCAATTCATGAAAAATA

TCTGTGAAAAGATTGGGCATAGAACCACCACCCTTCGTTGTCTTGCAGAG

AGAGCACTGCTGAGATATCTAGAGGGAGGCTGCTCGGTGCCAATTGGGGT

CTCCACTATTTATAGCGAGGATACGAAGGAACTTACCATGAACTCCCTAG

TCGTCAGTTGTAACGGTCGTGACTCGGTAACAGAATCAATGACTGAAGTC

GTGACTACTGAAGAGCAAGCTGAAGATTTCGGTGAAAGGCTGGCCCAGAA

GCTCATAGATCAAGGTGCGAAACGCATTCTTGACGAGATCAACTTCAACA

AGATCAAAGAGATTAAGGAAGAGGGTTTACATTAA

Heme biosynthesis enzyme 4-Uroporphyrinogen III
synthase
(SEQ ID NO: 14)
ATGCCAAAAGCCATTCTTCTGAAGAATAAAACTACACCGAAGGATCCTTA

TCTGGAGAACTTCGTAAGTAGTGGCTACTCGACCGATTTCGTACCACTTT

TAGATCATATTCACATGGAGAAATCTGAGATCATCGCATTTCTCAAGACT

GACTACTTTTGCATAAAACTTTGGCGTTTATTATTACGTCCCAAAGAGC

TGTAGAAATGCTGAATGAGTGTATGCAAATACTGAGACGTACTGATCCTG

AAATTACACAAATCATCTATAGTAAACCTGTCTATACAGTTGGCCCTGCC

ACCTACAGAATACTTGCGGATGCTGGCTTCGTGGATCTACGAGGCGGAGA

TAAGGCAGGAAACGGATCCATTCTAGCCCAGATAATTTTGAATGATGACA

TTTACACTGGAATTGAAGATTCTGACAAGCATATAACGTTTTTCACGGGA

GAAACAAGGAGAGACATAATTCCCAAATGTTTACTCTCTAACAACTTTCA

ACTTTACGAAAAGATTGTCTACAAGACTCTTCCTAGGGATGATATCGTGA

CTAGATTCAAGTCTGCCGTTGACAGCATCGACCAATCGCAAAGAAGTTCC

AGTTGGGTGGTCTTCTTTTCGCCTCAAGGAACAGAGGACATTGTAACGTA

TCTTCAACACACCAAAGACCAATTTAATATTGCATCTATCGGGCCAACCA

CAGAAAAATACCTTCTAAGCAAAAACCTGAAACCAAAAGTTGTGGCACCT

AAGCCAGAGCCTATCTCTTTACTATTGTCTATACAAAAAGTGCACTAA

Heme biosynthesis enzyme 5-Uroporphyrinogen III
decarboxylase
(SEQ ID NO: 15)
ATGAGTAGATTTCCAGAACTGAAGAATGACCTTATTTTAAGGGCAGCTCG

TGGTGAAAAAGTTGAACGTCCCCCAATATGGATTATGAGACAGGCCGGAA

GATATCTTCCGGAGTACCATGAGGTCAAAGGAGGTAGGGACTTCTTTGAA

ACTTGCAGGGATGCTGAGATTGCTTCTGAAATTACTATCCAGCCGATTAC

GCATTTTGACGGTCTGATCGATGCAGCTATTATCTTCAGTGATATCTTGG

TGATTCCTCAAGCTATGGGCATGGAAGTTAAGATGGTGGACAAAGTTGGC

CCACAGTTCCCAATCCGCTAAGAAACCGTCTGACTTGGATCATTTGAA

AAAAGACGTTGACGTTTTGAAGGAACTCGATTGGGCCTTCAAAGCTATCT

CATTGACCAGAAAAAACTCAATGGACGAGTGCCTTTGCTTGGATTTTGT

GGTGCTCCTTGGACTCTACTGGTTTATATGACTGAAGGAGGCGGTACCAA

-continued
```
GATGTTTCGATTTGCAAAAGAGTGGATCTACAAGTTTACCAAGGAATCTC
ATCAATTACTCCAACAGATCACTGACGTTGCAGTTGAATTCTTAGCTCAG
CAAGTTGTTGCAGGTGCCCAAATGTTACAAGTTTTTGAATCTTGGGCGG
TGAATTGGGGCCTGATGAATTCGATGAGTTTTCTTTGCCTTATTTGAGAC
AGATTTCCTCTAAACTTCCCCTGAGGTTGAAGGAACTTGGAATCACAGAG
AATGTTCCCATAACTGTCTTTGCTAAAGGCTCTTGGTACGCCTTGGAGCA
ATTGTGCGACAGTGGTTATGATGTTGTCTCGTTGGATTGGTTATTCCGTC
CAAGTGATGCTGTCCAGATTGCTAACGGAAGAATCGCATTGCAAGGTAAT
CTTGACCCTGGAACCATGTACGGCTCCAAAGAAACCATTTCCAAGAAAGT
GGACAAAATGATCAAGGGTTTTGGTGGAGGAAAGCAAAACTACATAATTA
ATTTTGGACACGGCACTCATCCATTCATGGATCCAGAACAGATCAGATGG
TTCTTACAAGAATGTCATCGCATTGGATCTCAATAG
```
Heme biosynthesis enzyme 6-Coproporphyrinogen III oxidase
(SEQ ID NO: 16)
```
ATGGCCATCGACTCTGATATCAATCTAAGCTCTCCCAATGATTCCATCCG
TCAAAGGATGTTCGAGCTTATCCAGCGGAAGCAACTCGAAATTGTCGCTG
CATTGGAGGCAATTGAAGGAAACGATACCAAATTTCGTTCTGATTCTTGG
GAAAGAGGAGCCGAAGGTGGAGGAGGAAGATCTATGCTTATTCAAGATGG
AAGAGTGTTTGAAAGGCTGGTGTAAATATTTCCAAGGTTCATGGCGTAT
TGCCTCCTCAAGCTGTGAGCCAGATGAGAAATGACCACTCCAAGCTAGAT
CTGCCTGCGGGAACCTCTCTGAAGTTCTTTGCCTGTGGGCTTTCGTTGGT
CATTCATCCCCATAATCCCCATGCTCCAACTACCCATCTGAATTATCGCT
ACTTCGAAACTTGGGATGAAACTGGAAAGCCTCACACCTGGTGGTTTGGG
GGCGGTGCTGATTTAACGCCTTCGTACCTGTATCCCGAGGATGCCAAGCA
ATTCCATCAAGCCCATAAGGATGCCCTGGACAAACACGATGTTAGCTTGT
ACCCGAGATTCAAAAAGTGGTGTGATGAATACTTTCTGATCAAACATCGA
AATGAAACTAGAGGTATTGGGGGTATTTTCTTTGATGATTTTGACGAGTT
TGATGCTGAGAGGTCCCTGAAGTTGGTTGAAGATTGTTTCAATGCTTTCT
TGGAATCTTATCCCGCTATCACTCGAAAAAGGATGGACACCCCTTCAACT
GATGCTGAGAAGAACTGGCAACAAATTAGAAGAGGAAGATATGTCGAATT
CAACTTAGTATTGGATAGAGGTACTCAATTTGGTTTGAGAACGCCTGGAT
CTCGTGTTGAAAGTATTTTGATGTCGTTGCCAAGAACAGCTGGTTGGGTC
TATGATCATCATCCAGAGCCTGGCTCCAGAGAAGAGGAGTTATTGCAGGT
ACTACAAAATCCTATTGAATGGGTATGA
```
Heme biosynthesis enzyme 7-Protoporphyrinogen oxidase
(SEQ ID NO: 17)
```
ATGCTGAAAAGTCTTGCACCAAATTCCTCAATTGCCGTTTTAGGTTCAGG
GATATCTGGATTGACTTTCAGCTTTTTTTTGAATCGGTTGCGTCCCGATG
TTAAGATCCATATCTTTGAAAAATCCAAGAGGTTGGAGGATGGATCAGAT
CAGAAGAGCATGAAACTTTTCATTTTGAAAAGGGACCCAGAACTTTGAGA
GGCACAAATACGGGTACCTTGATGTTGTTGGATCTTCTTACCAAGATAGG
AGCAAATGACAAGGTCCTGGGACTGCACAAAGATTCTCTTGCTAATAAAA
AGTATCTGTTGTCCCCGTTCTCAGATGTTCACGGAAACAACGCAAAGCTT
CTTCAAGTGCCACAGGATTTCAGCTCTTTTGTAAAGTTCATGTTTGACCC
GTTGTCTAAGGATCTCATTCTCGGTCTTTTGAAAGAACCATGGCAACCAA
AATTAAAGTATTCAGATGAGTCGGTTGACCATTTTTTCAACAGAAGATTT
GCTACCAAACTATCAGAGAATATCGTCAGCGCAATTGTGCATGGAATCTA
TGCGGGCGACGTGAAGAAGTTAAGTGTGAAAGCCATCTTCCCTAGGCTCC
CTGAGATGGAACAGGAAAGTGGCTCTATTATAAGGTATATGATCGCCCAA
TACAGGACAAAAAGAACGTCAAACAAAAAGTTGACCCTTTTTTGGCAGA
TTATGAAAATTGATCGGTACATCTTTGAGTTTCAAAAATATTTCTTTGT
TTCTGAAAAACTTTCCCATGCTGAGTTTTCAGGGTGGACTACAGAAACTT
CCCATCTCATTGAAGAACCATTTATCACAGATTGAAAACATCAAGTTTCA
TTTTGACAGCAAAATCAAAAACATTGCTTTGGAGAGCGGTAAGGTGGCAT
TGACTGACCATGATCAGGTTTATCTTGTTGACCATGTGAGATCTACCATT
AATACCAACGAATTGGCCAAAATCATTTCACCCGTTGTTCCAAGTTCTAC
TAAGAAAAAATCCGTTTTCAAATCCAAAGCGAATGGCCCAGGGCTGGTCA
AATGTTTGAGCTGGCTACACTATACAAATATACTAATGTGCAACATTTAT
ATACCTAAGCACGTCTCAAAATCTATCACCGGATTTGGATACTTGGTTCC
TCGATCAATGTCTTCTCAGGCATCCAAACTTCTCGGTGTCATATTTGACT
CAGACATCGAGACTGCAATGACTCCTAATTTTACAGAGGCCAACATTACG
GCGATAAACAGTAACTCTGCATCTCCCAAGCAACTCCAAAAGTTTTCTGA
CCAATTCGTCAATAATGATCTCCCTAAATACACCAAGTTGACGCTAATGC
TTGGAGGTCATTATCTCAAGTCGGAGGCAGACATGCCCGGTTCCGCAGAG
AGTAAACATGCTGTCAAGGCGATTCTGTCAAATCACCTGAATATTGATCT
AGATGAGTTTGCATCTTTGCCAGACTTCAAGATGGAAATCACCAAGATCC
CCAACTGCATTCCCCAATATGAAGTTGGGTATCTTGATCTCAAGAGAAAG
GTTCAGAATGCAGCCTCCAAAGAGTTCAACGACCAAATAAGTTTTGGAGG
CATGGCATTTGGTGATGGTGTGGGATCCCTGACTGTGTCCAGAATGCAT
TCAAAGATTCGGCTACCCTCAGTGGCATTTAA
```
Heme biosynthesis enzyme 8- Ferrochelatase
(SEQ ID NO: 18)
```
ATGCTTAACCGTCGTTTCCAATCTACCGTGTCCTCGAGTCTGAACAAGGG
CACTGGAATAGTGTTCATGAATATGGGTGGTCCCTCCACTGTCAAGGAAA
CCTATGACTTTTTATTTCGTCTTTTCTCGGACGGAGATTTAATCCCGTTT
GGCAGATTTCAGAACATCCTGGCCCGCTTCATTGCAAGTAGAAGAACACC
CAAAATTGAATCCTACTACAAAGCTATCGGAGGTGGGTCTCCTATCCGAA
AGTGGTCTGAATACCAGAGTTCTAAACTATGTGAAAAATTAGACATTATC
AGTCCACAATCGGCTCCTCATAAGCCTTATGTTGCCTTCAGATACGCTAA
TCCTCTCACTGAAGATACTTTACAAAAGATGAAAAATGATGGAATTACTA
AGGCCATTGCCTTTTCTCAATATCCGCAATTTAGTTATTCAACCACCGGA
TCATCGATTAACGAACTTTACAGGCAATCGAAAATTTTGGACCCTGATCA
ATCTATTAAATGGACAGTTATAGATCGCTGGCCTGACCACCCAGCCTTAG
```

```
-continued
TTAAAACTTTCGCAGCTCATATCAAAGATACTCTAAACAGATTCAAAACT

GAAAATGGACTGACTGACACAAAAGACGTCGTCCTCCAATTCAGTGCTCA

TTCTTTACCAATGGATATTGTCAATAAAGGAGATTCGTATCCTGCAGAAG

TCGCAGCGAGTGTCTTTGCCATTATGAAAGAACTTAACTTCTCAAATCCT

TATAAATTAACCTGGCAATCACAGGTTGGCCCAAAGCCTTGGCTGGGTGC

TCAAACTGAAAAAATTACCAAGCAGCTAGCATCCAGTGATGTTCCTGGAG

TCGTTTTGGTTCCTATTGCCTTTACCTCTGATCATATTGAAACTCTCCAT

GAACTGGATATTGAACTGATTCAAGAACTACCTAATCCTTCAAAAGTAAA

GCGAGTTGAATCGTTGAACGGAGACCAAACTTTCATTGACTCCTTGGCAG

AACTAGTGAAGAGTCACATTGATTCGAAGGTTGTATTTTCCAACCAGTTG

CCATTGGATTCCATGCTGGGAGTAGTGTCAGATAATTCCCTCACAGATCC

AAAAGAGTTTTTCAGAGCCCATTGA
```

Part C. Results and Discussion

Example 24—Characterization of Strain MXY0183

Optimum growth conditions for Strain MXY0183 include a target pH of 3.0 to 6.0 and temperatures of 28-35° C. In order to produce the LegH protein, strain MXY0183 must be alive and growing aerobically for a period of 6 days.

Figure 8:
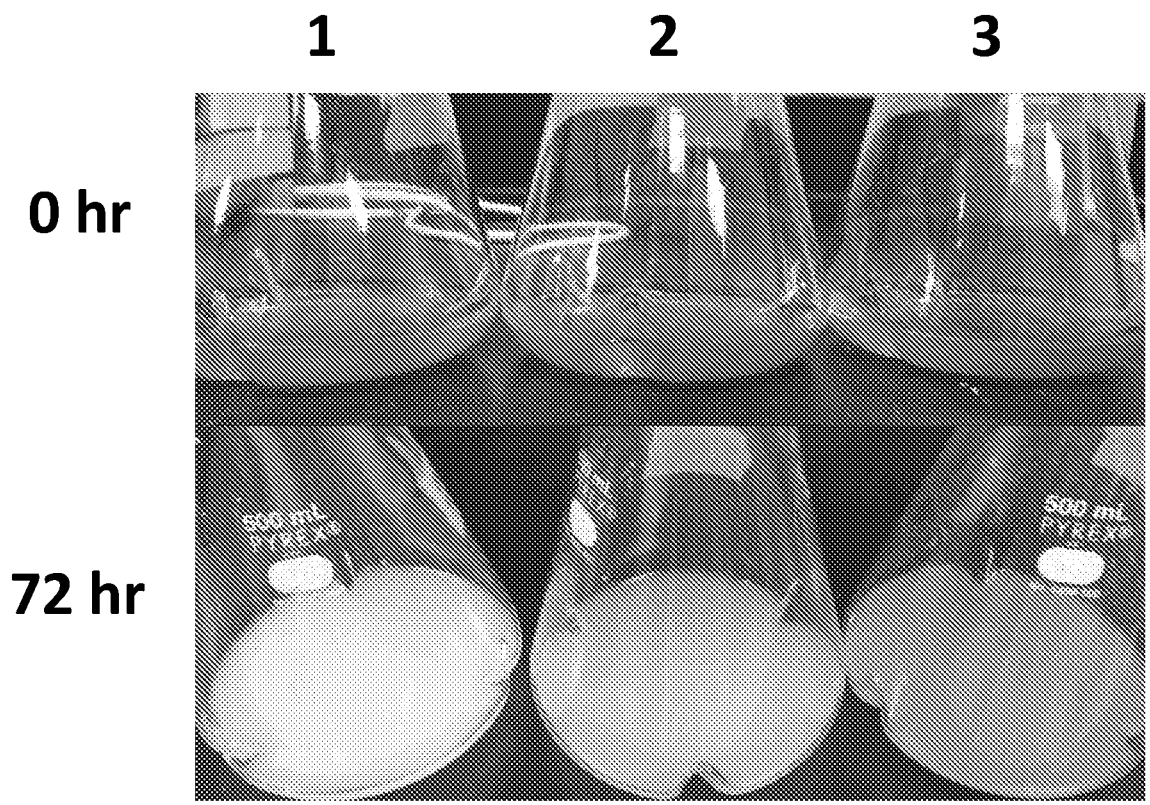
FIG. 8 is a photograph showing the phenotypic changes associated with strain, MXY0183. Shake flasks at the start of induction (0 hr) and 72 hr post-induction are shown. 1, MXY0051; 2, MXY0118; 3, MXY0183.

Expression of the genes associated with strain MXY0183 resulted in phenotypic changes to the strain. FIG. 8 shows photographs of shake flasks at the start of induction (0 hr) and 72 hr post-induction. The flasks designated #1 contain the host strain, MXY0051. The flasks designated #2 and #3 contain one of the intermediate strains (i.e., MXY0118, containing >10 copies of the LegH gene and the ALA dehydratase from the heme biosynthetic pathway) and the production strain (i.e., MXY0183, containing >10 copies of the LegH gene and the 8 enzymes from the heme biosynthetic pathway), respectively. The characteristic red color in flask #3 after 72 hours demonstrates the production of heme-bound LegH.

Figure 9:
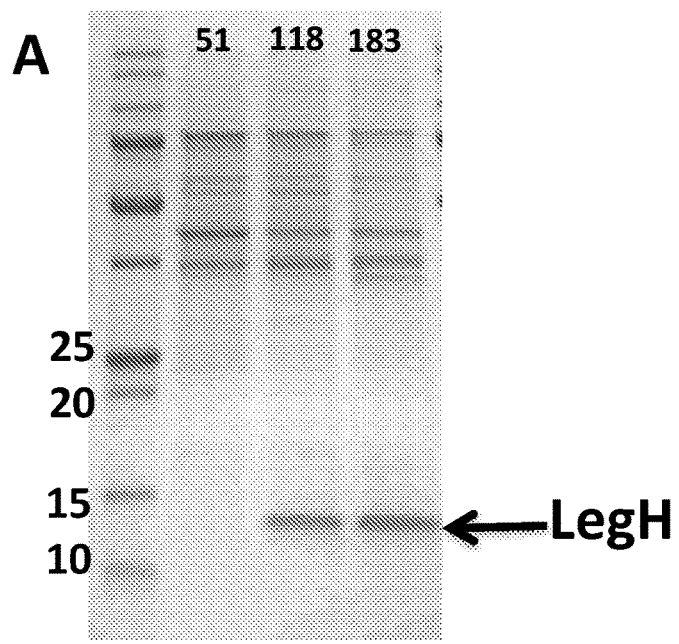
FIG. 9 shows the production of LegH from the modified *P. pastoris* strains. Panel A is a SDS gel showing lysates from *P. pastoris* strains grown in shake flasks: 51, MXY0051; 118, MXY0118; 183, MXY0183. Panel B is a table comparing LegH production from strains MXY0118, MXY0183, and MXY0207.

After growing in shake flasks, the *P. pastoris* strains indicated above, MXY0051, MXY0118, and MXY0183, were lysed and the proteins run on a SDS gel (FIG. 9A). The arrow shows the position of the LegH protein. A comparison of LegH production in strain MXY0183 and in strain MXY0118 is shown in FIG. 9B, which demonstrates the efficiency of heme loading of the LegH protein by the MXY0183 strain.

Example 25—Characterization of Strain MXY0207

Figure 10:
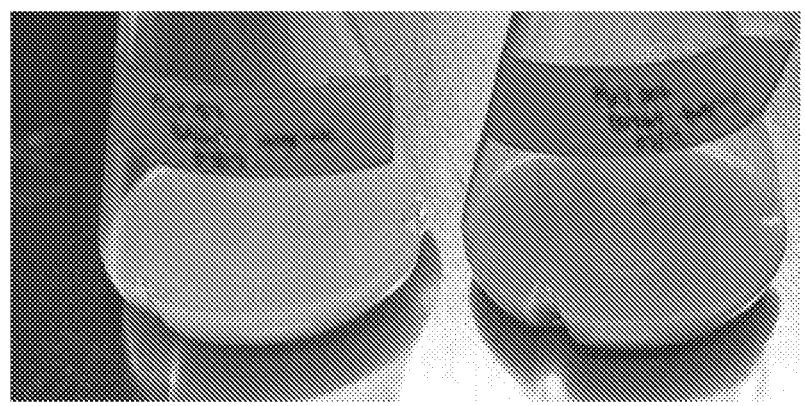
FIG. 10 shows data from experiments with strain MXY0206. Panel A is a photograph of shake flask cultures of strains MXY0183 (left) and MXY0206 (right) after 48 hr of growth in repressing carbon source. Panel B is a photograph of cell pellets from shake flask cultures of strains MXY0183 (left) and MXY0206 (right) after 48 hr of growth in BMY media. Panel C is a graph showing the relative yield of heme-loaded LegH (in the absence of any induction agent).
Figure 10:
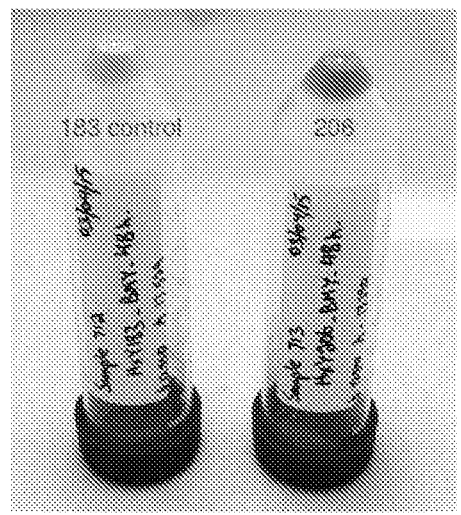

Experiments were then performed to determine the benefits of overexpressing the transcriptional activator, Mxr1, in the presence of the genes encoding the 8 enzymes involved in heme biosynthesis. Strain MXY0183, which contains >10 copies of the LegH sequence and the genes encoding the 8 enzymes involved in heme biosynthesis, and sister strains MXY0206 and MXY0207, which contain >10 copies of the LegH sequence, the genes encoding the 8 enzymes involved in heme biosynthesis, and the Mxr1 transcriptional activator, were grown in shake flask cultures in the presence of glycerol, which is a repressing carbon source for these strains. Photographs of the shake flask cultures after 48 hr are shown in FIG. 10A, and photographs of the pellets from cells grown on BMY media for 48 hours with no additional source of carbon are shown in FIG. 10B; these experiments demonstrated that significant expression of transgenes (e.g. heme enzymes) under the control of the AOX1 promoter occurs in the absence of an inducing carbon source when a repressing carbon source is consumed in the growth medium of a strain in which Mxr1 is also expressed from the AOX1 promoter. The relative yield of heme-loaded LegH, when shake flask cultures were grown in the absence of induction agent, is shown in FIG. 10C. These experiments demonstrated that significant production of a recombinant, heme-loaded protein is accomplished from AOX1 promoter-driven transgenes in the absence of methanol induction in *Pichia* strains in which Mxr1 expression is also driven by the AOX1 promoter.

Select strains were grown in 2 L fermenter tanks, and the relative yield of LegH and heme-loaded LegH was determined (FIG. 11). Compared to strain MXY0183, the MXY0207 strain produced even more LegH and was able to produce enough heme to heme-load the LegH protein very effectively.

Example 26—Characterization of Strain MXY0291

As described above in Examples 18-20, strain MXY0291 was constructed to recapitulate the LegH production ability of MXY0207, while being free of antibiotic resistance genes. It was determined that strain MXY0291 contained ~16 copies of LegH var3, Mxr1 and 7 of the 8 heme biosynthetic enzymes. When grown in 2 L fermenter tanks, this strain showed improved LegH yield compared to MXY0207. This improvement was seen both in induction media containing methanol/glycerol and methanol/dextrose (D-glucose) (FIG. 11).

Example 27—Characterization of Hybrid Promoter Strains

Additional copies of soybean leghemoglobin (LegH) were expressed under three different constitutive promoters, pGAP, pGCW14 and pTEF1, in a strain that already contains several copies of LegH, all heme biosynthetic enzymes, and the transcriptional factor Mxr1 under control of the promoter, pAOX1 (referred to above as MXY0291). When induced by methanol in the presence of dextrose (i.e., D-glucose), the constitutive promoters and pAOX1 drive expression of LegH while only the pAOX1 promoter drives expression of the heme enzymes. This leads to further improvement in LegH yield compared to previous strain MXY0291 (FIG. 11).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A methylotrophic yeast cell comprising a recombinant nucleic acid molecule, wherein the recombinant nucleic acid molecule comprises a first exogenous nucleic acid encoding a methanol expression regulator 1 (Mxr1) transcriptional activator operably linked to at least one methanol-inducible promoter element comprising a sequence to which the Mxr1 transcriptional activator binds, wherein the recombinant nucleic acid molecule comprises a second exogenous nucleic acid encoding a heterologous polypeptide operably linked to at least one methanol-inducible promoter element.

2. The yeast cell of claim 1, wherein the methylotrophic yeast cell is of a yeast selected from the group consisting of *Candida*, *Hansenula*, *Pichia* and *Torulopsis*.

3. The yeast cell of claim 1, wherein the cell is a *Pichia* cell.

4. The yeast cell of claim 1, wherein the cell is a *Pichia pastoris* cell.

5. The yeast cell of claim 1, wherein the recombinant nucleic acid molecule is stably integrated into the genome of the methylotrophic yeast cell.

6. The yeast cell of claim 1, wherein the recombinant nucleic acid molecule is extrachromosomally expressed from a replication-competent plasmid.

7. The yeast cell of claim 1, wherein the exogenous nucleic acid encoding a transcriptional activator comprises a Mxr1 sequence from *Pichia pastoris*.

8. The yeast cell of claim 1, wherein the transcriptional activator comprises the sequence shown in SEQ ID NO: 59.

9. The yeast cell of claim 8, wherein the transcriptional activator is encoded by the nucleic acid sequence shown in SEQ ID NO: 60.

10. The yeast cell of claim 1, wherein the at least one methanol-inducible promoter element is selected from the group consisting of an alcohol oxidase 1 (AOX1) promoter element from *Pichia pastoris*, an alcohol oxidase (AOD1) promoter element from *Candida boidinii*, a methanol oxidase (MOX) promoter element from *Hansenula polymorpha*, a methanolica alcohol oxidase (MOD1) promoter element from *Pichia methanolica*, a dihydroxyacetone synthase (DHAS) promoter element from *Pichia pastoris*, a formaldehyde dehydrogenase (FLD1) promoter element from *Pichia pastoris*, and a peroxin 8 (PEX8) promoter element from *Pichia pastoris*.

11. The yeast cell of claim 1, wherein the at least one methanol-inducible promoter element is an alcohol oxidase 1 (AOX1) promoter element from *Pichia pastoris*.

12. The yeast cell of claim 1, wherein the second exogenous nucleic acid encodes at least one heterologous polypeptide involved in biosynthesis of an iron co-factor.

13. The yeast cell of claim 12, wherein the iron co-factor is heme.

14. The yeast cell of claim 13, wherein the at least one polypeptide involved in the biosynthesis of heme is selected from the group consisting of aminolevulinic acid (ALA) synthase, ALA dehydratase, porphobilinogen deaminase, uroporphyrinogen (UPG) III synthase, UPG III decarboxylase, coproporphyrinogen (CPG) oxidase, protoporphyrin (PPG) oxidase, and ferrochelatase.

15. The yeast cell of claim 13, wherein the at least one polypeptide involved in the biosynthesis of heme comprises two or more polypeptides selected from the group consisting of ALA synthase, ALA dehydratase, porphobilinogen deaminase, UPG III synthase, UPG III decarboxylase, CPG oxidase, PPG oxidase, and ferrochelatase.

16. A method for expressing a heterologous polypeptide in a cell, the method comprising:
   providing the yeast cell of claim 1; and
   culturing the cell under conditions for expression of the recombinant nucleic acid molecule,
   thereby expressing the heterologous polypeptide.

17. The method of claim 16, wherein the heterologous polypeptide is a member of globin family PF00042.

18. The method of claim 16, wherein the heterologous polypeptide is a plant hemoglobin.

19. The method of claim 18, wherein the plant hemoglobin is leghemoglobin.

20. The method of claim 19, wherein the leghemoglobin has a sequence selected from the group consisting of SEQ ID NO:4 and SEQ ID NO:6.

21. The method of claim 16, wherein the introducing step comprises a technique selected from the group consisting of transduction, electroporation, biolistic particle delivery, and chemical transformation.

22. The method of claim 16, wherein the conditions under which the cell is cultured comprises addition of iron or a pharmaceutically or metabolically acceptable salt thereof.

23. The method of claim 16, wherein the culturing step comprises culturing the cell in the presence of methanol.

24. The method of claim 16, wherein the culturing step comprises culturing the cell in the absence of methanol.

25. The method of claim 16, wherein the culturing step comprises culturing the cell in the absence of selection.

26. A methylotrophic *Pichia* yeast cell comprising a recombinant nucleic acid molecule, wherein the recombinant nucleic acid molecule comprises:
 a nucleic acid encoding a Mxr1 transcriptional activator sequence from *P. pastoris*;
 a nucleic acid encoding a member of globin family PF00042; and a nucleic acid encoding at least one polypeptide involved in heme biosynthesis, wherein each nucleic acid is operably linked to a methanol-inducible promoter element, wherein the methanol-inducible promoter element comprises at least one sequence to which a Mxrl1 transcriptional activator binds.

27. The yeast cell of claim 26, wherein the member of the globin family is leghemoglobin.

28. The yeast cell of claim 26, wherein the methanol-inducible promoter element is an alcohol oxidase 1 (AOX1) promoter element from *P. pastoris*.

* * * * *

```
                              SEQUENCE LISTING

<160> NUMBER OF SEQ ID NOS: 60

<210> SEQ ID NO 1
<211> LENGTH: 3486
<212> TYPE: DNA
<213> ORGANISM: Komagataella phaffii

<400> SEQUENCE: 1
atgcgagacc gcggccgcat gagcaatcta cccccaactt ttggttccac tagacaatct      60
ccagaagacc aatcacctcc cgtgcccaag gagctgtcat tcaatgggac cacaccctca     120
ggaaagctac gcttatttgt ctgtcagaca tgtactcgag catttgctcg tcaggaacac     180
ttgaaacgac acgaaaggtc tcacaccaag gagaaacctt tcagctgcgg catttgttct     240
cgtaaattca gccgtcgaga tctgttattg agacatgccc aaaaactgca cagcaactgc     300
tctgatgcgg ccataacaag actaaggcgc aaggcaactc gtcggtcttc taatgccgcg     360
ggttccatat ctggttctac tccggtgaca acgccaaata ctatgggtac gcccgaagat     420
ggcgagaaac gaaaagttca gaaactggcc ggccgccggg actcaaatga acagaaactg     480
caactgcaac aacaacatct acagcaacaa ccacagttgc aataccaaca atctcttaag     540
cagcatgaaa atcaagtcca gcagcctgat caagatccat tgatatcccc gagaatgcaa     600
ttattcaatg attccaacca tcacgtaaac aatttgtttg atcttggact aagaagagct     660
tccttctccg ccgttagtgg aaataattat gcccattatg tgaataattt tcaacaagat     720
gcctcttcta ccaatccaaa tcaagattca aataatgccg aatttgagaa tattgaattt     780
tctaccccac aaatgatgcc cgttgaagat gctgaaactt ggatgaacaa catgggtcca     840
attccgaact tctctctcga tgtgaacagg aacattggtg atagctttac agatatacaa     900
cacaagaatt cagagcctat tatatccgaa ccgcccaagg acaccgctcc aaacgacaag     960
aagttgaatg gctactcttt ttacgaagcc cccatcaagc cattagaatc cctattttct    1020
gtcaggaata caaagagaaa caagtataaa acaaatgacg actctccaga caccgtggat    1080
aataactccg caccggctgc taataccatt caagaacttg agtcttcttt gaatgcatcc    1140
aagaattttt gcttgccaac tggttattcc ttctatggta atttggacca acagactttc    1200
tctaacacgt tatcatgcac ttcttctaat gccacaattt cgcccattct actcgataac    1260
tccattaata ataactccac tagtgacgtg agaccagaat ttagaacaca aagtgtcacc    1320
tctgaaatga gtcaagcccc tcccctcct caaaaaaaca actcgaaata ttccaccgaa    1380
gttcttttta ccagcaacat gcggtcgttt attcactacg ctcttttccaa gtatcctttt    1440 attggtgtgc ccactccaac tcttccggag aacgaaagac taaatgaata tgctgattca    1500
ttcaccaacc gtttcttaaa tcattatcct ttcatacatg tcacgattct caagaatac    1560 tcccttttca aggcaattt agatgagaat gagtcgacta agaactggga aaataatcag    1620
ttttacttag agaaccaacg aatatcaatt gtttgtcttc ctcttttggt ggctacgata    1680
ggtgcagtac tatcaaacaa caaaaaggat gcttcgaatt tatacgaagc ttcaaggcgt    1740
tgtattcatg tttacttaga ttccaggaaa aagatacccca cttccttgtc cgcaaataac    1800
aatgactctc cactttggct aattcaatcc ctgacgttat ctgttatgta tgggttattt    1860
gcggacaatg acattagttt gaatgtcgtg atcagacaag ttaacgcact taattctctg    1920
```

-continued

```
gtcaagactt cgggcctgaa taggacctca attatagatc ttttcaacat caacaaacct   1980
ttggataatg aactctggaa tcaattcgtg aaaatagagt ccaccgtaag gacaatccac   2040 acgattttc aaatcagttc aacttaagc gccttgtaca atattattcc atcgttgaaa     2100
attgatgacc taatgattac tctaccagtt cccacaacac tttggcaagc tgattctttt   2160
gtgaaattca aaagtctaag ttacggaaat cagatccctt tcaatatac aagagtacta    2220 cagaatttga ttgattacaa tcagccattg agcgatggaa aattttttgta tgaaaaccat  2280 gtaagtgagt ttggactcat atgcctacag aatggtctac accaatacag ctatttccaa   2340
aaattgactg ctgtcaataa cagagaagat gcgctattca caaggttgt taattcactt    2400 cacagttggg ataggatgat ttcgaattct gatttgtttc caagaagat atatcagcag    2460 agttgcttga ttttggactc aaagttgctt aataatttcc tgattgtcaa gagctcattg   2520
aaagtttcga ccggagacgt tagttctttg aataagttaa agaaaacgt gtggcttaaa    2580 aactggaatc aagtgtgtgc tatctattat aacagcttca tgaacattcc tgctcccagt   2640
attcaaaaga agtacaatga catagagttt gtggatgaca tgattaattt gagtctaatc   2700
atcatcaaga ttatgaaact cattttctat aacaatgtca aagacaatta tgaggatgaa   2760
aatgacttca aattgcaaga gttaaattta acatttgaca attttgatga gaaaatatcc   2820
ttgaatttga caatattatt cgatatattt ttgatgatct acaagataat taccaattac   2880
gaaaagttta tgaagatcaa acacaagttt aattactaca attctaattc gaatataagc   2940
ttcttgcatc atttcgaact ctcctcggtt atcaataaca cccaaatgaa ccagaatgat   3000
tatatgaaaa cagatattga tgaaaagctt gatcagcttt tccacatcta tcaaacatt    3060 ttccggctgt atctggattt agaaaagttt atgaagttca aattcaacta tcatgacttt   3120
gagacagagt tttcaagtct ctcaatatcc aatatactga acactcatgc tgcttctaac   3180
aatgacacaa atgctgctga tgctatgaat gccaaggatg aaaaaatatc tcccacaact   3240
ttgaatagcg tattacttgc tgatgaagga aatgaaaatt ccggtcgtaa taacgattca   3300
gaccgcctgt tcatgctgaa cgagctaatt aattttgaag taggtttgaa atttctcaag   3360
ataggtgagt catttttga tttcttgtat gagaataact acaagttcat ccacttcaaa   3420
aacttaaatg acggaatgtt ccacatcagg atatacctag aaaaccgact agatggtggt   3480
gtctag                                                             3486
```

<210> SEQ ID NO 2
<211> LENGTH: 1161
<212> TYPE: PRT
<213> ORGANISM: Komagataella phaffii

<400> SEQUENCE: 2

```
Met Arg Asp Arg Gly Arg Met Ser Asn Leu Pro Pro Thr Phe Gly Ser
1               5                   10                  15

Thr Arg Gln Ser Pro Glu Asp Gln Ser Pro Val Pro Lys Glu Leu
            20                  25                  30

Ser Phe Asn Gly Thr Thr Pro Ser Gly Lys Leu Arg Leu Phe Val Cys
        35                  40                  45

Gln Thr Cys Thr Arg Ala Phe Ala Arg Gln Glu His Leu Lys Arg His
    50                  55                  60

Glu Arg Ser His Thr Lys Glu Lys Pro Phe Ser Cys Gly Ile Cys Ser
65                  70                  75                  80

Arg Lys Phe Ser Arg Arg Asp Leu Leu Leu Arg His Ala Gln Lys Leu
```

```
                         85                  90                  95
His Ser Asn Cys Ser Asp Ala Ala Ile Thr Arg Leu Arg Arg Lys Ala
                100                 105                 110

Thr Arg Arg Ser Ser Asn Ala Ala Gly Ser Ile Ser Gly Ser Thr Pro
            115                 120                 125

Val Thr Thr Pro Asn Thr Met Gly Thr Pro Glu Asp Gly Glu Lys Arg
        130                 135                 140

Lys Val Gln Lys Leu Ala Gly Arg Arg Asp Ser Asn Glu Gln Lys Leu
145                 150                 155                 160

Gln Leu Gln Gln Gln His Leu Gln Gln Gln Pro Gln Leu Gln Tyr Gln
                165                 170                 175

Gln Ser Leu Lys Gln His Glu Asn Gln Val Gln Gln Pro Asp Gln Asp
                180                 185                 190

Pro Leu Ile Ser Pro Arg Met Gln Leu Phe Asn Asp Ser Asn His His
            195                 200                 205

Val Asn Asn Leu Phe Asp Leu Gly Leu Arg Arg Ala Ser Phe Ser Ala
        210                 215                 220

Val Ser Gly Asn Asn Tyr Ala His Tyr Val Asn Asn Phe Gln Gln Asp
225                 230                 235                 240

Ala Ser Ser Thr Asn Pro Asn Gln Asp Ser Asn Asn Ala Glu Phe Glu
                245                 250                 255

Asn Ile Glu Phe Ser Thr Pro Gln Met Met Pro Val Glu Asp Ala Glu
            260                 265                 270

Thr Trp Met Asn Asn Met Gly Pro Ile Pro Asn Phe Ser Leu Asp Val
        275                 280                 285

Asn Arg Asn Ile Gly Asp Ser Phe Thr Asp Ile Gln His Lys Asn Ser
        290                 295                 300

Glu Pro Ile Ile Ser Glu Pro Pro Lys Asp Thr Ala Pro Asn Asp Lys
305                 310                 315                 320

Lys Leu Asn Gly Tyr Ser Phe Tyr Glu Ala Pro Ile Lys Pro Leu Glu
                325                 330                 335

Ser Leu Phe Ser Val Arg Asn Thr Lys Arg Asn Lys Tyr Lys Thr Asn
            340                 345                 350

Asp Asp Ser Pro Asp Thr Val Asp Asn Ser Ala Pro Ala Ala Asn
            355                 360                 365

Thr Ile Gln Glu Leu Glu Ser Ser Leu Asn Ala Ser Lys Asn Phe Cys
        370                 375                 380

Leu Pro Thr Gly Tyr Ser Phe Tyr Gly Asn Leu Asp Gln Gln Thr Phe
385                 390                 395                 400

Ser Asn Thr Leu Ser Cys Thr Ser Ser Asn Ala Thr Ile Ser Pro Ile
                405                 410                 415

Leu Leu Asp Asn Ser Ile Asn Asn Asn Ser Thr Ser Asp Val Arg Pro
            420                 425                 430

Glu Phe Arg Thr Gln Ser Val Thr Ser Glu Met Ser Gln Ala Pro Pro
        435                 440                 445

Pro Pro Gln Lys Asn Asn Ser Lys Tyr Ser Thr Glu Val Leu Phe Thr
    450                 455                 460

Ser Asn Met Arg Ser Phe Ile His Tyr Ala Leu Ser Lys Tyr Pro Phe
465                 470                 475                 480

Ile Gly Val Pro Thr Pro Thr Leu Pro Glu Asn Glu Arg Leu Asn Glu
                485                 490                 495

Tyr Ala Asp Ser Phe Thr Asn Arg Phe Leu Asn His Tyr Pro Phe Ile
            500                 505                 510
```

```
His Val Thr Ile Leu Lys Glu Tyr Ser Leu Phe Lys Ala Ile Leu Asp
            515                 520                 525
Glu Asn Glu Ser Thr Lys Asn Trp Glu Asn Asn Gln Phe Tyr Leu Glu
            530                 535                 540
Asn Gln Arg Ile Ser Ile Val Cys Leu Pro Leu Leu Val Ala Thr Ile
545                 550                 555                 560
Gly Ala Val Leu Ser Asn Asn Lys Lys Asp Ala Ser Asn Leu Tyr Glu
                    565                 570                 575
Ala Ser Arg Arg Cys Ile His Val Tyr Leu Asp Ser Arg Lys Lys Ile
                580                 585                 590
Pro Thr Ser Leu Ser Ala Asn Asn Asp Ser Pro Leu Trp Leu Ile
                595                 600                 605
Gln Ser Leu Thr Leu Ser Val Met Tyr Gly Leu Phe Ala Asp Asn Asp
            610                 615                 620
Ile Ser Leu Asn Val Val Ile Arg Gln Val Asn Ala Leu Asn Ser Leu
625                 630                 635                 640
Val Lys Thr Ser Gly Leu Asn Arg Thr Ser Ile Ile Asp Leu Phe Asn
                    645                 650                 655
Ile Asn Lys Pro Leu Asp Asn Glu Leu Trp Asn Gln Phe Val Lys Ile
                660                 665                 670
Glu Ser Thr Val Arg Thr Ile His Thr Ile Phe Gln Ile Ser Ser Asn
            675                 680                 685
Leu Ser Ala Leu Tyr Asn Ile Ile Pro Ser Leu Lys Ile Asp Asp Leu
            690                 695                 700
Met Ile Thr Leu Pro Val Pro Thr Thr Leu Trp Gln Ala Asp Ser Phe
705                 710                 715                 720
Val Lys Phe Lys Ser Leu Ser Tyr Gly Asn Gln Ile Pro Phe Gln Tyr
                    725                 730                 735
Thr Arg Val Leu Gln Asn Leu Ile Asp Tyr Asn Gln Pro Leu Ser Asp
                740                 745                 750
Gly Lys Phe Leu Tyr Glu Asn His Val Ser Glu Phe Gly Leu Ile Cys
            755                 760                 765
Leu Gln Asn Gly Leu His Gln Tyr Ser Tyr Phe Gln Lys Leu Thr Ala
            770                 775                 780
Val Asn Asn Arg Glu Asp Ala Leu Phe Thr Lys Val Val Asn Ser Leu
785                 790                 795                 800
His Ser Trp Asp Arg Met Ile Ser Asn Ser Asp Leu Phe Pro Lys Lys
                    805                 810                 815
Ile Tyr Gln Gln Ser Cys Leu Ile Leu Asp Ser Lys Leu Leu Asn Asn
                820                 825                 830
Phe Leu Ile Val Lys Ser Ser Leu Lys Val Ser Thr Gly Asp Val Ser
            835                 840                 845
Ser Leu Asn Lys Leu Lys Glu Asn Val Trp Leu Lys Asn Trp Asn Gln
850                 855                 860
Val Cys Ala Ile Tyr Tyr Asn Ser Phe Met Asn Ile Pro Ala Pro Ser
865                 870                 875                 880
Ile Gln Lys Lys Tyr Asn Asp Ile Glu Phe Val Asp Asp Met Ile Asn
                    885                 890                 895
Leu Ser Leu Ile Ile Ile Lys Ile Met Lys Leu Ile Phe Tyr Asn Asn
                900                 905                 910
Val Lys Asp Asn Tyr Glu Asp Glu Asn Asp Phe Lys Leu Gln Glu Leu
            915                 920                 925
```

Asn Leu Thr Phe Asp Asn Phe Asp Glu Lys Ile Ser Leu Asn Leu Thr
    930                 935                 940

Ile Leu Phe Asp Ile Phe Leu Met Ile Tyr Lys Ile Ile Thr Asn Tyr
945                 950                 955                 960

Glu Lys Phe Met Lys Ile Lys His Lys Phe Asn Tyr Tyr Asn Ser Asn
                965                 970                 975

Ser Asn Ile Ser Phe Leu His His Phe Glu Leu Ser Ser Val Ile Asn
            980                 985                 990

Asn Thr Gln Met Asn Gln Asn Asp Tyr Met Lys Thr Asp Ile Asp Glu
        995                 1000                1005

Lys Leu Asp Gln Leu Phe His Ile Tyr Gln Thr Phe Phe Arg Leu
    1010                1015                1020

Tyr Leu Asp Leu Glu Lys Phe Met Lys Phe Lys Phe Asn Tyr His
    1025                1030                1035

Asp Phe Glu Thr Glu Phe Ser Ser Leu Ser Ile Ser Asn Ile Leu
    1040                1045                1050

Asn Thr His Ala Ala Ser Asn Asn Asp Thr Asn Ala Ala Asp Ala
    1055                1060                1065

Met Asn Ala Lys Asp Glu Lys Ile Ser Pro Thr Thr Leu Asn Ser
    1070                1075                1080

Val Leu Leu Ala Asp Glu Gly Asn Glu Asn Ser Gly Arg Asn Asn
    1085                1090                1095

Asp Ser Asp Arg Leu Phe Met Leu Asn Glu Leu Ile Asn Phe Glu
    1100                1105                1110

Val Gly Leu Lys Phe Leu Lys Ile Gly Glu Ser Phe Phe Asp Phe
    1115                1120                1125

Leu Tyr Glu Asn Asn Tyr Lys Phe Ile His Phe Lys Asn Leu Asn
    1130                1135                1140

Asp Gly Met Phe His Ile Arg Ile Tyr Leu Glu Asn Arg Leu Asp
    1145                1150                1155

Gly Gly Val
    1160

<210> SEQ ID NO 3
<211> LENGTH: 438
<212> TYPE: DNA
<213> ORGANISM: Artificial Sequence
<220> FEATURE:
<223> OTHER INFORMATION: Glycine max leghemoglobin codon-optimized for
      Pichia pastoris

<400> SEQUENCE: 3
atgggtgctt tcaccgagaa gcaggaagca cttgtttcct cttcgttcga agcttttaag      60
gctaacatcc tcaatactc tgttgtgttt tacacgtcca ttctagaaaa agctcctgct     120
gccaaggacc tcttctcttt tctgtccaac ggtgtagatc catccaatcc caaattaaca     180
ggtcacgctg agaaattgtt cggtttagtc agagatagcg ctggacaatt gaaagcaaat     240
ggtactgtgg ttgctgatgc tgccttgggc agcatccatg cacagaaggc aattacagac     300
ccacaatttg ttgttgtgaa ggaagctctg cttaaaacta taaggaagc cgtcggagac     360 aaatggagtg acgagttgtc atcagcttgg gaggtagctt atgatgagtt ggccgcagca     420
atcaaaaagg cattctaa                                                  438

<210> SEQ ID NO 4
<211> LENGTH: 145
<212> TYPE: PRT

<213> ORGANISM: Artificial Sequence
<220> FEATURE:
<223> OTHER INFORMATION: Glycine max leghemoglobin codon-optimized for Pichia pastoris

<400> SEQUENCE: 4

```
Met Gly Ala Phe Thr Glu Lys Gln Glu Ala Leu Val Ser Ser Ser Phe
1               5                   10                  15

Glu Ala Phe Lys Ala Asn Ile Pro Gln Tyr Ser Val Val Phe Tyr Thr
            20                  25                  30

Ser Ile Leu Glu Lys Ala Pro Ala Ala Lys Asp Leu Phe Ser Phe Leu
        35                  40                  45

Ser Asn Gly Val Asp Pro Ser Asn Pro Lys Leu Thr Gly His Ala Glu
    50                  55                  60

Lys Leu Phe Gly Leu Val Arg Asp Ser Ala Gly Gln Leu Lys Ala Asn
65                  70                  75                  80

Gly Thr Val Val Ala Asp Ala Ala Leu Gly Ser Ile His Ala Gln Lys
                85                  90                  95

Ala Ile Thr Asp Pro Gln Phe Val Val Lys Glu Ala Leu Leu Lys
            100                 105                 110

Thr Ile Lys Glu Ala Val Gly Asp Lys Trp Ser Asp Glu Leu Ser Ser
        115                 120                 125

Ala Trp Glu Val Ala Tyr Asp Glu Leu Ala Ala Ile Lys Lys Ala
    130                 135                 140

Phe
145
```

<210> SEQ ID NO 6
<211> LENGTH: 438
<212> TYPE: DNA
<213> ORGANISM: Artificial Sequence
<220> FEATURE:
<223> OTHER INFORMATION: Glycine max leghemoglobin codon-optimized for Pichia pastoris

<400> SEQUENCE: 5

```
atgggtgcat ttacagaaaa acaagaggct ttagtatcct catcttttga agctttcaaa    60
gccaatattc tcaatactc cgttgttttc tatacgtcca ttttggaaaa ggctccagca   120
gctaaggacc ttttctcttt cttgtcgaac ggcgtggatc cctcaaatcc taagctgact   180
ggtcacgccg agaagctttt tggtttggtc agagacagcg ccggacagct gaaagctaac   240
ggtacagttg tggcagatgc tgccttggga tctatacatg cacaaaaggc tatcaccgac   300
ccacagtttg tggttgtaaa agaggctcta ctcaaaacta tcaaggaagc agttggtgac   360
aaatggagcg atgaattgtc cagtgcatgg gaggtcgctt acgatgagtt agctgctgca   420
atcaaaaagg ctttctaa                                                438
```

<210> SEQ ID NO 6
<211> LENGTH: 145
<212> TYPE: PRT
<213> ORGANISM: Artificial Sequence
<220> FEATURE:
<223> OTHER INFORMATION: Glycine max leghemoglobin codon-optimized for Pichia pastoris

<400> SEQUENCE: 6

```
Met Gly Ala Phe Thr Glu Lys Gln Glu Ala Leu Val Ser Ser Ser Phe
1               5                   10                  15

Glu Ala Phe Lys Ala Asn Ile Pro Gln Tyr Ser Val Val Phe Tyr Thr
```

```
                   20                  25                  30
Ser Ile Leu Glu Lys Ala Pro Ala Ala Lys Asp Leu Phe Ser Phe Leu
            35                  40                  45

Ser Asn Gly Val Asp Pro Ser Asn Pro Lys Leu Thr Gly His Ala Glu
        50                  55                  60

Lys Leu Phe Gly Leu Val Arg Asp Ser Ala Gly Gln Leu Lys Ala Asn
 65                  70                  75                  80

Gly Thr Val Val Ala Asp Ala Ala Leu Gly Ser Ile His Ala Gln Lys
                85                  90                  95

Ala Ile Thr Asp Pro Gln Phe Val Val Lys Glu Ala Leu Leu Lys
            100                 105                 110

Thr Ile Lys Glu Ala Val Gly Asp Lys Trp Ser Asp Glu Leu Ser Ser
        115                 120                 125

Ala Trp Glu Val Ala Tyr Asp Glu Leu Ala Ala Ile Lys Lys Ala
    130                 135                 140

Phe
145

<210> SEQ ID NO 7
<211> LENGTH: 939
<212> TYPE: DNA
<213> ORGANISM: Pichia pastoris

<400> SEQUENCE: 7
gatctaacat ccaaagacga aaggttgaat gaaacctttt tgccatccga catccacagg     60
tccattctca cacataagtg ccaaacgcaa caggagggga tacactagca gcagaccgtt    120
gcaaacgcag gacctccact cctcttctcc tcaacaccca cttttgccat cgaaaaacca    180
gcccagttat tgggcttgat tggagctcgc tcattccaat tccttctatt aggctactaa    240
caccatgact ttattagcct gtctatcctg gccccctgg cgaggttcat gtttgtttat     300
ttccgaatgc aacaagctcc gcattacacc cgaacatcac tccagatgag ggctttctga    360
gtgtggggtc aaatagtttc atgttcccca aatggcccaa aactgacagt ttaaacgctg    420
tcttggaacc taatatgaca aaagcgtgat ctcatccaag atgaactaag tttggttcgt    480
tgaaatgcta acggccagtt ggtcaaaaag aaacttccaa aagtcggcat accgtttgtc    540
ttgtttggta ttgattgacg aatgctcaaa ataatctca ttaatgctta gcgcagtctc     600
tctatcgctt ctgaaccccg gtgcacctgt gccgaaacgc aaatggggaa acacccgctt    660
tttggatgat tatgcattgt ctccacattg tatgcttcca agattctggt gggaatactg    720
ctgatagcct aacgttcatg atcaaaattt aactgttcta ccccctactt gacagcaata    780
tataaacaga aggaagctgc cctgtcttaa acctttttttt ttatcatcat tattagctta    840
ctttcataat tgcgactggt tccaattgac aagcttttga ttttaacgac ttttaacgac    900
aacttgagaa gatcaaaaaa caactaatta ttcgaaacg                           939

<210> SEQ ID NO 8
<211> LENGTH: 558
<212> TYPE: DNA
<213> ORGANISM: Pichia pastoris

<400> SEQUENCE: 8
cgactattat cgatcaatga aatccatcaa gattgaaatc ttaaaattgc ccctttcact     60
tgacaggatc cttttttgta gaaatgtctt ggtgtcctcg tccaatcagg tagccatctc    120
tgaaatatct ggctccgttg caactccgaa cgacctgctg gcaacgtaaa attctccggg    180
```

```
gtaaaactta aatgtggagt aatggaacca gaaacgtctc ttcccttctc tctccttcca      240
ccgcccgtta ccgtccctag gaaatttttac tctgctggag agcttcttct acggcccct     300 tgcagcaatg ctcttcccag cattacgttg cgggtaaaac ggaggtcgtg tacccgacct     360
agcagcccag ggatggaaaa gtcccggccg tcgctggcaa taatagcggg cggacgcatg     420
tcatgagatt attggaaacc accagaatcg aatataaaag gcgaacacct ttcccaattt     480
tggtttctcc tgacccaaag actttaaatt taatttattt gtccctattt caatcaattg     540
aacaactatc aaaacacg                                                   558
```

```
<210> SEQ ID NO 9
<211> LENGTH: 822
<212> TYPE: DNA
<213> ORGANISM: Pichia pastoris

<400> SEQUENCE: 9
```

```
caggtgaacc cacctaacta ttttttaactg ggatccagtg agctcgctgg gtgaaagcca     60
accatctttt gtttcgggga accgtgctcg ccccgtaaag ttaattttttt tttcccgcgc    120 agctttaatc tttcggcaga gaaggcgttt tcatcgtagc gtgggaacag aataatcagt    180
tcatgtgcta tacaggcaca tggcagcagt cactattttg cttttttaacc ttaaagtcgt    240 tcatcaatca ttaactgacc aatcagattt tttgcatttg ccacttatct aaaaatactt    300
ttgtatctcg cagatacgtt cagtggtttc caggacaaca cccaaaaaaa ggtatcaatg    360
ccactaggca gtcggtttta ttttttggtca cccacgcaaa gaagcaccca cctcttttag    420 gtttttaagtt gtgggaacag taacaccgcc tagagcttca ggaaaaacca gtacctgtga    480
ccgcaattca ccatgatgca gaatgttaat ttaaacgagt gccaaatcaa gatttcaaca    540
gacaaatcaa tcgatccata gttacccatt ccagccttttt cgtcgtcgag cctgcttcat    600
tcctgcctca ggtgcataac tttgcatgaa aagtccagat tagggcagat tttgagttta    660
aaataggaaa tataaacaaa tataccgcga aaaaggtttg tttatagctt ttcgcctggt    720
gccgtacggt ataaatacat actctcctcc cccccctggt tctctttttc ttttgttact    780
tacattttac cgttccgtca ctcgcttcac tcaacaacaa aa                        822
```

```
<210> SEQ ID NO 10
<211> LENGTH: 424
<212> TYPE: DNA
<213> ORGANISM: Pichia pastoris

<400> SEQUENCE: 10
```

```
ataactgtcg cctctttttat ctgccgcact gcatgaggtg tccccttagt gggaaagagt      60
actgagccaa ccctggagga cagcaaggga aaaatacctta caacttgctt cataatggtc    120
gtaaaaacaa tccttgtcgg atataagtgt tgtagactgt cccttatcct ctgcgatgtt    180
cttcctctca aagtttgcga tttctctcta tcagaattgc catcaagaga ctcaggacta    240
atttcgcagt cccacacgca ctcgtacatg attggctgaa atttccctaa agaatttctt    300
tttcacgaaa atttttttttt tacacaagat tttcagcaga tataaaatgg agagcaggac    360
ctccgctgtg actcttcttt tttttctttt attctcacta catacattttt agttattcgc    420 caac                                                                  424
```

```
<210> SEQ ID NO 11
<211> LENGTH: 1683
<212> TYPE: DNA
```

<213> ORGANISM: Pichia pastoris

<400> SEQUENCE: 11

| | | |
|---|---|---|
| atggagtttg tcgcccgtca gtccatgaat gcctgtccct tgtcaggtc aacttctacc | 60 |
| caccatttga agaagttggc agcaaacagt tctctagctg ctactgctag tcattgtccc | 120 |
| gtggttggcc ctgctctcca acagcagaga tactactctc aaccttccaa gccagcccaa | 180 |
| gcccaaacct ccgacattgc tactgggatc aagaaggatg tttctccgat ccgtatggac | 240 |
| tctaatgaaa ccgcctttga ttacaatgga atgtatgagt ctgatcttgc gaataaacgt | 300 |
| aaagataact cgtatcgtta tttcaataac atcaaccgtc tagccaagga gtttcccaag | 360 |
| gcacatcgcc agaccgaaga tgacaaggtg accgtctggt gctctaacga ctacttagga | 420 |
| atgggtaggc atcctgagat tatcaaaacc atgaaggcta ccatggacaa gtacggttcc | 480 |
| ggagcaggag gaactaggaa cattgcaggt cataaccacg ccgctatcaa tttggaaagc | 540 |
| gagttggctt gcttgaacaa gaaggaagcg gctctggtgt tttcatcatg tttcatagct | 600 |
| aacgatgcaa tcatctcgtt gttgggacaa aaaatcaaaa atttggtcat tttctctgac | 660 |
| cagtcgaatc atgcttccat gatattgggt gtgcgtaact ccaaagcgaa gaagcacatc | 720 |
| ttcaagcaca acaatttgaa ggatctggag tcgcagttag ctcagtaccc caagtcgact | 780 |
| cctaaactga tcgccttcga gtcagtttac tctatgtgtg gatctgtggc tcccattgag | 840 |
| aagatttgcg atttggctaa aaggtacggt gccctcacct tcttggatga agttcatgct | 900 |
| gttggaatgt atggtcctca tggacagggt gtagctgagc atttggactt tgatctgcat | 960 |
| ttacagtctg gaatcgccag tcctagcgtg gtggacaaac gcaccatatt ggatcgtgtc | 1020 |
| gacatgatta ctggtacttg cggaaagtca tttggtactg ttggaggtta cgttgctggt | 1080 |
| agtgccaacc taattgattg gttaagatcc tatgcgccag gtttcatttt cactaccaca | 1140 |
| cttcctcctg ctatcatggc tggtacagcc acttctgttc gtattgttag ggccgacatt | 1200 |
| gaggcccgta tcaagcaaca gcttaatact cgctacgtca agactcatt tgaaaacctt | 1260 |
| ggtattccag tcattccaaa cccaagtcac attgttcctg ttctagttgg aaatgctgca | 1320 |
| gatgccaaga aggcatccga tatgttaatg aacaaacacc gtatttatgt tcaagctatt | 1380 |
| aactacccta ctgtgcctgt cggtgaagaa cgactaagga ttactcctac tccaggtcat | 1440 |
| ggaaaggaga tttgtgacca gctgatcagc gctgtcgacg atgtttttac tgagcttaat | 1500 |
| ttaccaagaa tcaacaaatg gcagtcccaa ggtggtcatt gcggtgttgg tgatgctaat | 1560 |
| tacgtaccag aacccaatct gtggactcag gaccagctca gcttgacaaa ccaagacttg | 1620 |
| cactccaatg tgcacaaccc agtgattgag cagatcgaaa cctcatcagg agtcagattg | 1680 |
| tag | 1683 |

<210> SEQ ID NO 12
<211> LENGTH: 1026
<212> TYPE: DNA
<213> ORGANISM: Pichia pastoris

<400> SEQUENCE: 12

| | | |
|---|---|---|
| atggtgcata aggctgaata cttggacgac cacccaactc agatttccag cattctttca | 60 |
| ggaggttaca accaccccatt acttcgtgaa tggcaacatg aacgtcaact caacaaaaac | 120 |
| atgttcatct ttcccctgtt tgtcacagat cgaccagacg aagaagaact tattcctagt | 180 |
| ctacctaata tcaagaggtt tggcgttaac aagttgattc cttatgtagg aggtttggtt | 240 |
| tccaaaggat tgagggcggt gatcctattt ggtgttcctc tgaagcccgg tgtgaaagat | 300 |

```
gaagaaggaa cggccgctga tgatccagag ggacctgtta tccaagccat caaacacttg      360
agaaagaact ttcctgacct gtatatcatc accgatgtct gtctatgtga gtacaccagc      420
catggacatt gtggaatact atatgaggat ggcactatca acagagagct ctcagtccgt      480
cgtattgctg ctgtagctgt caaatatgct caagctggag ccaactctgt ggctccttct      540
gatatgactg acggcagaat aagagatatt aagaaggct tactaagtgc aggactggca       600
cataaaacgt ttgttatgtc ctacgctgca aaattctctg gtaatttgta tggccctttc      660
agagatgctg caggttcctg tccatctcaa ggggacagaa atgttacca gcttccttct       720 ggaggaaaag ggttggccca tcgtgctctg attcgtgata tgaatgaagg cactgatgga      780
attattgtca aaccatctac attctatttg acattgtcg ctgatgctta tcagctttgt       840
aaagactatc ctatctgctg ttaccaggtt tctggagagt acgccatgct acatgcagcg      900
gcagagaaga atattgttga tctgaaatca atcgcttttg aagctcatca aggattcttg      960
cgggctggag ctcgtttaat cattagttac tttaccctg aattcctgga gtggttatct       1020
gaatga                                                                  1026

<210> SEQ ID NO 13
<211> LENGTH: 1035
<212> TYPE: DNA
<213> ORGANISM: Pichia pastoris

<400> SEQUENCE: 13
atgaaccaaa tcgaacagag cggacccatt gattgcagtt ccttgaaatt ggggtcccga       60
aagtccgctc tggctataat ccaggcagaa atcgtccgcc aattgatatt gaaagaatac      120
cctgaattgg agacgaagtt ggtcagtgtg tccaccctgg gggaccaagt ccagaataaa      180
gcacttttca cgtttggagg aaaatctttg tggaccaaag aacttgagat gttgttgttg      240
gagagtgtgg gaggatttga ccaaatagac atgattgtac actcgttgaa agacatgcca      300
actcatttac cagacgaatt tgagctgggt tgcattattg aaagagaaga ccctagagac      360
gctttggtcg tgcaagatgg tttatcttac aagtcattgg ccgaccttcc agagggagct      420
gtggtcggta cgtcttcggt tagaagatcg gctcaactac tgaagaattt ccctcatctg      480
aaattcaaat ctgttagagg aaaccttcag accagactaa gaaaattaga tgatccagat      540
tccgagtact gctgtctcct ccttgcagca gccggtttaa tcaggacagg cttacaacac      600
agaatttcaa tgtatttgaa cgacgatgtg atgtaccact ccgtcggaca aggagcatta      660
ggagtagaga tcagaaaagg tgaccaattc atgaaaaata tctgtgaaaa gattgggcat      720
agaaccacca cccttcgttg tcttgcagag agagcactgc tgagatatct agagggaggc      780
tgctcggtgc caattggggt ctccactatt tatagcgagg atacgaagga acttaccatg      840
aactccctag tcgtcagttg taacggtcgt gactcggtaa cagaatcaat gactgaagtc      900
gtgactactg aagagcaagc tgaagatttc ggtgaaaggc tggcccagaa gctcatagat      960
caaggtgcga aacgcattct tgacgagatc aacttcaaca agatcaaaga gattaaggaa      1020
gagggtttac attaa                                                        1035

<210> SEQ ID NO 14
<211> LENGTH: 798
<212> TYPE: DNA
<213> ORGANISM: Pichia pastoris

<400> SEQUENCE: 14
```

```
atgccaaaag ccattcttct gaagaataaa actacaccga aggatcctta tctggagaac      60
ttcgtaagta gtggctactc gaccgatttc gtaccacttt tagatcatat tcacatggag    120
aaatctgaga tcatcgcatt tctcaagact gactacttttt tgcataaaac tttggcgttt    180
attattacgt cccaaagagc tgtagaaatg ctgaatgagt gtatgcaaat actgagacgt    240
actgatcctg aaattacaca atcatctat agtaaacctg tctatacagt tggccctgcc     300
acctacagaa tacttgcgga tgctggcttc gtggatctac gaggcggaga taaggcagga    360
aacggatcca ttctagccca gataattttg aatgatgaca tttacactgg aattgaagat    420
tctgacaagc atataacgtt tttcacggga gaaacaagga gagacataat cccaaatgt     480 ttactctcta acaactttca actttacgaa agattgtct acaagactct tcctagggat     540
gatatcgtga ctagattcaa gtctgccgtt gacagcatcg accaatcgca aagaagttcc    600
agttgggtgg tcttctttc gcctcaagga acagaggaca ttgtaacgta tcttcaacac     660
accaaagacc aatttaatat tgcatctatc gggccaacca cagaaaaata ccttctaagc    720
aaaaacctga accaaaagt tgtggcacct aagccagagc ctatctcttt actattgtct    780
atacaaaaag tgcactaa                                                   798

<210> SEQ ID NO 15
<211> LENGTH: 1086
<212> TYPE: DNA
<213> ORGANISM: Pichia pastoris

<400> SEQUENCE: 15
atgagtagat ttccagaact gaagaatgac cttatttaa gggcagctcg tggtgaaaaa       60
gttgaacgtc ccccaatatg gattatgaga caggccggaa gatatcttcc ggagtaccat    120
gaggtcaaag gaggtaggga cttctttgaa acttgcaggg atgctgagat tgcttctgaa    180
attactatcc agccgattac gcattttgac ggtctgatcg atgcagctat tatcttcagt    240
gatatcttgg tgattcctca agctatgggc atggaagtta agatggtgga caaagttggc    300
ccacagttcc ccaatccgct aagaaaaccg tctgacttgg atcatttgaa aaaagacgtt    360 gacgtttttga aggaactcga ttgggccttc aaagctatct cattgaccag aaaaaaactc    420
aatggacgag tgcctttgct tggattttgt ggtgctcctt ggactctact ggtttatatg    480
actgaaggag gcggtaccaa gatgtttcga tttgcaaaag agtggatcta caagtttacc    540
aaggaatctc atcaattact ccaacagatc actgacgttg cagttgaatt cttagctcag    600
caagttgttg caggtgccca aatgttacaa gttttttgaat cttggggcgg tgaattgggg    660
cctgatgaat tcgatgagtt ttctttgcct tatttgagac agatttcctc taaacttccc    720
ctgaggttga aggaacttgg aatcacagag aatgttccca taactgtctt tgctaaaggc    780
tcttggtacg ccttggagca attgtgcgac agtggttatg atgttgtctc gttggattgg    840
ttattccgtc caagtgatgc tgtccagatt gctaacggaa gaatcgcatt gcaaggtaat    900
cttgaccctg aaccatgta cggctccaaa gaaaccattt ccaagaaagt ggacaaaatg    960
atcaagggtt ttggtggagg aaagcaaaac tacataatta atttttggaca cggcactcat   1020 ccattcatgg atccagaaca gatcagatgg ttcttacaag aatgtcatcg cattggatct   1080
caatag                                                                1086

<210> SEQ ID NO 16
<211> LENGTH: 978
<212> TYPE: DNA
<213> ORGANISM: Pichia pastoris
```

<400> SEQUENCE: 16

```
atggccatcg actctgatat caatctaagc tctcccaatg attccatccg tcaaaggatg      60
ttcgagctta tccagcggaa gcaactcgaa attgtcgctg cattggaggc aattgaagga     120
aacgatacca aatttcgttc tgattcttgg gaaagaggag ccgaaggtgg aggaggaaga     180
tctatgctta ttcaagatgg aagagtgttt gaaaaggctg gtgtaaatat ttccaaggtt     240
catggcgtat tgcctcctca agctgtgagc cagatgagaa atgaccactc caagctagat     300
ctgcctgcgg aacctctct gaagttcttt gcctgtgggc tttcgttggt cattcatccc      360
cataatcccc atgctccaac tacccatctg aattatcgct acttcgaaac ttgggatgaa     420
actggaaagc ctcacacctg gtggtttggg ggcggtgctg atttaacgcc ttcgtacctg     480
tatcccgagg atgccaagca attccatcaa gcccataagg atgccctgga caaacacgat     540
gttagcttgt acccgagatt caaaaagtgg tgtgatgaat actttctgat caaacatcga     600
aatgaaacta gaggtattgg gggtattttc tttgatgatt ttgacgagtt tgatgctgag     660
aggtccctga agttggttga agattgtttc aatgctttct ggaatcttta tcccgctatc     720
actcgaaaaa ggatggacac cccttcaact gatgctgaga gaactggca acaaattaga      780
agaggaagat atgtcgaatt caacttagta ttggatagag gtactcaatt tggtttgaga     840
acgcctggat ctcgtgttga agtatttttg atgtcgttgc caagaacagc tggttgggtc     900
tatgatcatc atccagagcc tggctccaga gaagaggagt tattgcaggt actacaaaat     960
cctattgaat gggtatga                                                   978
```

<210> SEQ ID NO 17
<211> LENGTH: 1683
<212> TYPE: DNA
<213> ORGANISM: Pichia pastoris

<400> SEQUENCE: 17

```
atgctgaaaa gtcttgcacc aaattcctca attgccgttt taggttcagg gatatctgga      60
ttgactttca gcttttttt gaatcggttg cgtcccgatg ttaagatcca tatctttgaa     120
aaatccaagc aggttggagg atggatcaga tcagaagagc atgaaacttt tcattttgaa     180
aagggaccca gaactttgag aggcacaaat acgggtacct tgatgttgtt ggatcttctt     240
accaagatag gagcaaatga caaggtcctg ggactgcaca aagattctct tgctaataaa     300
aagtatctgt tgtccccgtt ctcagatgtt cacggaaaca acgcaaagct tcttcaagtg     360
ccacaggatt tcagctcttt tgtaaagttc atgtttgacc cgttgtctaa ggatctcatt     420
ctcggtcttt tgaaagaacc atggcaacca aaattaaagt attcagatga gtcggttgac     480
catttttca acagaagatt tgctaccaaa ctatcagaga atatcgtcag cgcaattgtg     540
catggaatct atgcgggcga cgtgaagaag ttaagtgtga agccatctt ccctaggctc     600
cctgagatgg aacaggaaag tggctctatt ataaggtata tgatcgccca atacaggaca     660
aaaaagaacg tcaaacaaaa agttgaccct tttttggcag attatgaaaa attgatcggt     720
acatctttga gtttcaaaaa tatttctttg tttctgaaaa actttcccat gctgagtttt     780
cagggtggac tacagaaact tcccatctca ttgaagaacc attatcaca gattgaaaac     840
atcaagtttc attttgacag caaaatcaaa acattgctt tggagagcgg taaggtggca     900
ttgactgacc atgatcaggt ttatcttgtt gaccatgtga gatctaccat taataccaac     960
gaattggcca aaatcatttc acccgttgtt ccaagttcta ctaagaaaaa atccgttttc    1020
```

| | | | | |
|---|---|---|---|---|
| aaatccaaag | cgaatggccc | agggctggtc | aaatgtttga | gctggctaca | ctatacaaat | 1080 |
| atactaatgt | gcaacattta | tatacctaag | cacgtctcaa | aatctatcac | cggatttgga | 1140 |
| tacttggttc | ctcgatcaat | gtcttctcag | gcatccaaac | ttctcggtgt | catatttgac | 1200 |
| tcagacatcg | agactgcaat | gactcctaat | tttacagagg | ccaacattac | ggcgataaac | 1260 |
| agtaactctg | catctcccaa | gcaactccaa | aagttttctg | accaattcgt | caataatgat | 1320 |
| ctccctaaat | acaccaagtt | gacgctaatg | cttggaggtc | attatctcaa | gtcggaggca | 1380 |
| gacatgcccg | gttccgcaga | gagtaaacat | gctgtcaagg | cgattctgtc | aaatcacctg | 1440 |
| aatattgatc | tagatgagtt | tgcatctttg | ccagacttca | agatggaaat | caccaagatc | 1500 |
| cccaactgca | ttccccaata | tgaagttggg | tatcttgatc | tcaagagaaa | ggttcagaat | 1560 |
| gcagcctcca | aagagttcaa | cgaccaaata | agttttggag | gcatggcatt | tggtgatggt | 1620 |
| gtggggatcc | ctgactgtgt | ccagaatgca | ttcaaagatt | cggctaccct | cagtggcatt | 1680 |
| taa | | | | | 1683 |

<210> SEQ ID NO 18
<211> LENGTH: 1125
<212> TYPE: DNA
<213> ORGANISM: Pichia pastoris

<400> SEQUENCE: 18

| | | | | | |
|---|---|---|---|---|---|
| atgcttaacc | gtcgtttcca | atctaccgtg | tcctcgagtc | tgaacaaggg | cactggaata | 60 |
| gtgttcatga | atatgggtgg | tccctccact | gtcaaggaaa | cctatgactt | tttatttcgt | 120 |
| cttttctcgg | acggagattt | aatcccgttt | ggcagatttc | agaacatcct | ggcccgcttc | 180 |
| attgcaagta | gaagaacacc | caaaattgaa | tcctactaca | aagctatcgg | aggtgggtct | 240 |
| cctatccgaa | agtggtctga | ataccagagt | tctaaactat | gtgaaaaatt | agacattatc | 300 |
| agtccacaat | cggctcctca | taagccttat | gttgccttca | gatacgctaa | tcctctcact | 360 |
| gaagatactt | tacaaaagat | gaaaaatgat | ggaattacta | aggccattgc | ctttttctcaa | 420 |
| tatccgcaat | ttagttattc | aaccaccgga | tcatcgatta | acgaacttta | caggcaatcg | 480 |
| aaaattttgg | accctgatca | atctattaaa | tggacagtta | tagatcgctg | gcctgaccac | 540 |
| ccagccttag | ttaaaacttt | cgcagctcat | atcaaagata | ctctaaacag | attcaaaact | 600 |
| gaaaatggac | tgactgacac | aaaagacgtc | gtcctccaat | tcagtgctca | ttcttttacca | 660 |
| atggatattg | tcaataaagg | agattcgtat | cctgcagaag | tcgcagcgag | tgtctttgcc | 720 |
| attatgaaag | aacttaactt | ctcaaatcct | tataaattaa | cctggcaatc | acaggttggc | 780 |
| ccaaagcctt | ggctgggtgc | tcaaactgaa | aaaattacca | agcagctagc | atccagtgat | 840 |
| gttcctggag | tcgttttggt | tcctattgcc | tttacctctg | atcatattga | aactctccat | 900 |
| gaactggata | ttgaactgat | tcaagaacta | cctaatcctt | caaaagtaaa | gcgagttgaa | 960 |
| tcgttgaacg | gagaccaaac | tttcattgac | tccttggcag | aactagtgaa | gagtcacatt | 1020 |
| gattcgaagg | ttgtattttc | caaccagttg | ccattggatt | ccatgctggg | agtagtgtca | 1080 |
| gataattccc | tcacagatcc | aaaagagttt | ttcagagccc | attga | | 1125 |

<210> SEQ ID NO 19
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 19
gagggtctcg gatggagttt gtcgcccgtc    30

<210> SEQ ID NO 20
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 20
gagggtctcg attacaatct gactcctgat gagg    34

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
gagggtctcg gatggtgcat aaggctgaat acttg    35

<210> SEQ ID NO 22
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 22
gagggtctcg attattcaga taaccactcc agg    33

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 23
gagggtctcg gatgccaaaa gccattcttc tgaag    35

<210> SEQ ID NO 24
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 24
gagggtctcg attagtgcac tttttgtata gac    33

<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 25
gagggtctcg gatgagtaga tttccagaac tgaag    35

<210> SEQ ID NO 26
<211> LENGTH: 29
<212> TYPE: DNA

<213> ORGANISM: Artificial Sequence
<220> FEATURE:
<223> OTHER INFORMATION: Synthetic oligonucleotide

<400> SEQUENCE: 26
gagggtctcg attattgaga tccaatgcg                              29

<210> SEQ ID NO 27
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 27
gagggtctcg gatggccatc gactctgata tc                          32

<210> SEQ ID NO 28
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 28
gagggtctcg attataccca ttcaatagga t                           31

<210> SEQ ID NO 29
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 29
gagggtctcg gatgctgaaa agtcttgcac caaa                        34

<210> SEQ ID NO 30
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 30
gagggtctcg attaaatgcc actgagggta gc                          32

<210> SEQ ID NO 31
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 31
caatcgctag catccaacat ccaaagacga aagg                        34

<210> SEQ ID NO 32
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 32
ggatagcatg cacccttatca agatagctag aaatagaaat gg              42

<210> SEQ ID NO 33
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 33
caatagcatg caacatccaa agacgaaagg ttgaatg                         37

<210> SEQ ID NO 34
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 34
catggtaccg gtaccttatc aagatagcta gaaatagaaa tgg                  43

<210> SEQ ID NO 35
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 35
caatcgctag catccaacat ccaaagacga aagg                            34

<210> SEQ ID NO 36
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 36
gatattgctc gagaccttat caagatagct agaaatagaa atg                  43

<210> SEQ ID NO 37
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 37
caatctcgag aacatccaaa gacgaaaggt tg                              32

<210> SEQ ID NO 38
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 38
caaccatttc tatttctagc tatcttgata aggtcttaag tcca                 44

<210> SEQ ID NO 39
<211> LENGTH: 43
<212> TYPE: DNA
<213> ORGANISM: Artificial Sequence
<220> FEATURE:

<223> OTHER INFORMATION: Synthetic oligonucleotide

<400> SEQUENCE: 39
catggtaccg gtaccttatc aagatagcta gaaatagaaa tgg         43

<210> SEQ ID NO 40
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 40
ttacttaagt ccaacatcca aagacgaaag gttg         34

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
tcacagacgc gttgaattgt cc         22

<210> SEQ ID NO 42
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 42
ttgctcctca gcttagaaga actcgtccaa catcaagtg         39

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
ttagtcttgc tcctcagctt agcc         24

<210> SEQ ID NO 44
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 44
tcacagacgc gttgaattgt cc         22

<210> SEQ ID NO 45
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 45
ttttgcggcc gcatgagcaa tctacccca acttttg         37

```
<210> SEQ ID NO 46
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 46
aaaagcggcc gcctagacac caccatctag tcggtt                              36

<210> SEQ ID NO 47
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 47
actagatggt ggtgtctagt caagaggatg tcagaatgcc atttg                    45

<210> SEQ ID NO 48
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 48
tctgacatcc tcttgactag acaccaccat ctagtcggtt ttctag                   46

<210> SEQ ID NO 49
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 49
aaacgctgtc ttggaaccta atatgac                                        27

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
aaactgtcag ttttgggcca tttg                                           24

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
acgctgtctt ggaacctaat atgac                                          25

<210> SEQ ID NO 52
<211> LENGTH: 31
<212> TYPE: DNA
<213> ORGANISM: Artificial Sequence
<220> FEATURE:
<223> OTHER INFORMATION: Synthetic oligonucleotide
```

```
<400> SEQUENCE: 52
tacccattca ataggatttt gtagtacctg c                              31

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
gagcttcttc tacggccccc                                            20

<210> SEQ ID NO 54
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 54
tccagcagag taaaatttcc tagggac                                    27

<210> SEQ ID NO 55
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 55
ctcttttagg ttttaagttg tgggaacagt aaca                            34

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
gtgggtgctt ctttgcgtgg                                            20

<210> SEQ ID NO 57
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 57
agaattgcca tcaagagact caggact                                    27

<210> SEQ ID NO 58
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 58
gatagagaga aatcgcaaac tttgagagga ag                              32

<210> SEQ ID NO 59
<211> LENGTH: 1155
```

<212> TYPE: PRT
<213> ORGANISM: Komagataella pastoris

<400> SEQUENCE: 59

```
Met Ser Asn Leu Pro Pro Thr Phe Gly Ser Thr Arg Gln Ser Pro Glu
1               5                   10                  15

Asp Gln Ser Pro Pro Val Pro Lys Glu Leu Ser Phe Asn Gly Thr Thr
            20                  25                  30

Pro Ser Gly Lys Leu Arg Leu Phe Val Cys Gln Thr Cys Thr Arg Ala
        35                  40                  45

Phe Ala Arg Gln Glu His Leu Lys Arg His Glu Arg Ser His Thr Lys
50                  55                  60

Glu Lys Pro Phe Ser Cys Gly Ile Cys Ser Arg Lys Phe Ser Arg Arg
65                  70                  75                  80

Asp Leu Leu Leu Arg His Ala Gln Lys Leu His Ser Asn Cys Ser Asp
                85                  90                  95

Ala Ala Ile Thr Arg Leu Arg Arg Lys Ala Thr Arg Arg Ser Ser Asn
            100                 105                 110

Ala Ala Gly Ser Ile Ser Gly Ser Thr Pro Val Thr Pro Asn Thr
        115                 120                 125

Met Gly Thr Pro Glu Asp Gly Glu Lys Arg Lys Val Gln Lys Leu Ala
    130                 135                 140

Gly Arg Arg Asp Ser Asn Glu Gln Lys Leu Gln Leu Gln Gln His
145                 150                 155                 160

Leu Gln Gln Gln Pro Gln Leu Gln Tyr Gln Ser Leu Lys Gln His
                165                 170                 175

Glu Asn Gln Val Gln Gln Pro Asp Gln Asp Pro Leu Ile Ser Pro Arg
            180                 185                 190

Met Gln Leu Phe Asn Asp Ser Asn His His Val Asn Asn Leu Phe Asp
        195                 200                 205

Leu Gly Leu Arg Arg Ala Ser Phe Ser Ala Val Ser Gly Asn Asn Tyr
    210                 215                 220

Ala His Tyr Val Asn Asn Phe Gln Gln Asp Ala Ser Ser Thr Asn Pro
225                 230                 235                 240

Asn Gln Asp Ser Asn Asn Ala Glu Phe Glu Asn Ile Glu Phe Ser Thr
                245                 250                 255

Pro Gln Met Met Pro Val Glu Asp Ala Glu Thr Trp Met Asn Asn Met
            260                 265                 270

Gly Pro Ile Pro Asn Phe Ser Leu Asp Val Asn Arg Asn Ile Gly Asp
        275                 280                 285

Ser Phe Thr Asp Ile Gln His Lys Asn Ser Glu Pro Ile Ile Ser Glu
    290                 295                 300

Pro Pro Lys Asp Thr Ala Pro Asn Asp Lys Leu Asn Gly Tyr Ser
305                 310                 315                 320

Phe Tyr Glu Ala Pro Ile Lys Pro Leu Glu Ser Leu Phe Ser Val Arg
                325                 330                 335

Asn Thr Lys Arg Asn Lys Tyr Lys Thr Asn Asp Asp Ser Pro Asp Thr
            340                 345                 350

Val Asp Asn Asn Ser Ala Pro Ala Ala Asn Thr Ile Gln Glu Leu Glu
        355                 360                 365

Ser Ser Leu Asn Ala Ser Lys Asn Phe Cys Leu Pro Thr Gly Tyr Ser
    370                 375                 380

Phe Tyr Gly Asn Leu Asp Gln Gln Thr Phe Ser Asn Thr Leu Ser Cys
385                 390                 395                 400
```

```
Thr Ser Ser Asn Ala Thr Ile Ser Pro Ile Leu Leu Asp Asn Ser Ile
                405                 410                 415

Asn Asn Asn Ser Thr Ser Asp Val Arg Pro Glu Phe Arg Thr Gln Ser
            420                 425                 430

Val Thr Ser Glu Met Ser Gln Ala Pro Pro Pro Gln Lys Asn Asn
        435                 440                 445

Ser Lys Tyr Ser Thr Glu Val Leu Phe Thr Ser Asn Met Arg Ser Phe
    450                 455                 460

Ile His Tyr Ala Leu Ser Lys Tyr Pro Phe Ile Gly Val Pro Thr Pro
465                 470                 475                 480

Thr Leu Pro Glu Asn Glu Arg Leu Asn Glu Tyr Ala Asp Ser Phe Thr
                485                 490                 495

Asn Arg Phe Leu Asn His Tyr Pro Phe Ile His Val Thr Ile Leu Lys
            500                 505                 510

Glu Tyr Ser Leu Phe Lys Ala Ile Leu Asp Glu Asn Glu Ser Thr Lys
        515                 520                 525

Asn Trp Glu Asn Asn Gln Phe Tyr Leu Glu Asn Gln Arg Ile Ser Ile
    530                 535                 540

Val Cys Leu Pro Leu Leu Val Ala Thr Ile Gly Ala Val Leu Ser Asn
545                 550                 555                 560

Asn Lys Lys Asp Ala Ser Asn Leu Tyr Glu Ala Ser Arg Arg Cys Ile
                565                 570                 575

His Val Tyr Leu Asp Ser Arg Lys Lys Ile Pro Thr Ser Leu Ser Ala
            580                 585                 590

Asn Asn Asn Asp Ser Pro Leu Trp Leu Ile Gln Ser Leu Thr Leu Ser
        595                 600                 605

Val Met Tyr Gly Leu Phe Ala Asp Asn Asp Ile Ser Leu Asn Val Val
    610                 615                 620

Ile Arg Gln Val Asn Ala Leu Asn Ser Leu Val Lys Thr Ser Gly Leu
625                 630                 635                 640

Asn Arg Thr Ser Ile Ile Asp Leu Phe Asn Ile Asn Lys Pro Leu Asp
                645                 650                 655

Asn Glu Leu Trp Asn Gln Phe Val Lys Ile Glu Ser Thr Val Arg Thr
            660                 665                 670

Ile His Thr Ile Phe Gln Ile Ser Ser Asn Leu Ser Ala Leu Tyr Asn
        675                 680                 685

Ile Ile Pro Ser Leu Lys Ile Asp Asp Leu Met Ile Thr Leu Pro Val
    690                 695                 700

Pro Thr Thr Leu Trp Gln Ala Asp Ser Phe Val Lys Phe Lys Ser Leu
705                 710                 715                 720

Ser Tyr Gly Asn Gln Ile Pro Phe Gln Tyr Thr Arg Val Leu Gln Asn
                725                 730                 735

Leu Ile Asp Tyr Asn Gln Pro Leu Ser Asp Gly Lys Phe Leu Tyr Glu
            740                 745                 750

Asn His Val Ser Glu Phe Gly Leu Ile Cys Leu Gln Asn Gly Leu His
        755                 760                 765

Gln Tyr Ser Tyr Phe Gln Lys Leu Thr Ala Val Asn Asn Arg Glu Asp
    770                 775                 780

Ala Leu Phe Thr Lys Val Val Asn Ser Leu His Ser Trp Asp Arg Met
785                 790                 795                 800

Ile Ser Asn Ser Asp Leu Phe Pro Lys Lys Ile Tyr Gln Gln Ser Cys
                805                 810                 815
```

Leu Ile Leu Asp Ser Lys Leu Leu Asn Asn Phe Leu Ile Val Lys Ser
                820                 825                 830

Ser Leu Lys Val Ser Thr Gly Asp Val Ser Ser Leu Asn Lys Leu Lys
            835                 840                 845

Glu Asn Val Trp Leu Lys Asn Trp Asn Gln Val Cys Ala Ile Tyr Tyr
        850                 855                 860

Asn Ser Phe Met Asn Ile Pro Ala Pro Ser Ile Gln Lys Lys Tyr Asn
865                 870                 875                 880

Asp Ile Glu Phe Val Asp Asp Met Ile Asn Leu Ser Leu Ile Ile Ile
                885                 890                 895

Lys Ile Met Lys Leu Ile Phe Tyr Asn Asn Val Lys Asp Asn Tyr Glu
            900                 905                 910

Asp Glu Asn Asp Phe Lys Leu Gln Glu Leu Asn Leu Thr Phe Asp Asn
        915                 920                 925

Phe Asp Glu Lys Ile Ser Leu Asn Leu Thr Ile Leu Phe Asp Ile Phe
930                 935                 940

Leu Met Ile Tyr Lys Ile Ile Thr Asn Tyr Glu Lys Phe Met Lys Ile
945                 950                 955                 960

Lys His Lys Phe Asn Tyr Tyr Asn Ser Asn Ser Asn Ile Ser Phe Leu
                965                 970                 975

His His Phe Glu Leu Ser Ser Val Ile Asn Asn Thr Gln Met Asn Gln
            980                 985                 990

Asn Asp Tyr Met Lys Thr Asp Ile Asp Glu Lys Leu Asp Gln Leu Phe
        995                 1000                1005

His Ile Tyr Gln Thr Phe Phe Arg Leu Tyr Leu Asp Leu Glu Lys
    1010                1015                1020

Phe Met Lys Phe Lys Phe Asn Tyr His Asp Phe Glu Thr Glu Phe
    1025                1030                1035

Ser Ser Leu Ser Ile Ser Asn Ile Leu Asn Thr His Ala Ala Ser
    1040                1045                1050

Asn Asn Asp Thr Asn Ala Ala Asp Ala Met Asn Ala Lys Asp Glu
    1055                1060                1065

Lys Ile Ser Pro Thr Thr Leu Asn Ser Val Leu Leu Ala Asp Glu
    1070                1075                1080

Gly Asn Glu Asn Ser Gly Arg Asn Asn Asp Ser Asp Arg Leu Phe
    1085                1090                1095

Met Leu Asn Glu Leu Ile Asn Phe Glu Val Gly Leu Lys Phe Leu
    1100                1105                1110

Lys Ile Gly Glu Ser Phe Phe Asp Phe Leu Tyr Glu Asn Asn Tyr
    1115                1120                1125

Lys Phe Ile His Phe Lys Asn Leu Asn Asp Gly Met Phe His Ile
    1130                1135                1140

Arg Ile Tyr Leu Glu Asn Arg Leu Asp Gly Gly Val
    1145                1150

<210> SEQ ID NO 60
<211> LENGTH: 3468
<212> TYPE: DNA
<213> ORGANISM: Komagataella pastoris

<400> SEQUENCE: 60
atgagcaatc taccccccaac ttttggttcc actagacaat ctccagaaga ccaatcacct      60
cccgtgccca aggagctgtc attcaatggg accacaccct caggaaagct acgcttattt     120
gtctgtcaga catgtactcg agcatttgct cgtcaggaac acttgaaacg acacgaaagg     180

```
tctcacacca aggagaaacc tttcagctgc ggcatttgtt ctcgtaaatt cagccgtcga      240
gatctgttat tgagacatgc ccaaaaactg cacagcaact gctctgatgc ggccataaca      300
agactaaggc gcaaggcaac tcgtcggtct tctaatgccg cgggttccat atctggttct      360
actccggtga caacgccaaa tactatgggt acgcccgaag atggcgagaa cgaaaagtt       420 cagaaactgg ccggccgccg ggactcaaat gaacagaaac tgcaactgca acaacaacat      480
ctacagcaac aaccacagtt gcaataccaa caatctctta agcagcatga aaatcaagtc      540
cagcagcctg atcaagatcc attgatatcc ccgagaatgc aattattcaa tgattccaac      600
catcacgtaa acaatttgtt tgatcttgga ctaagaagag cttccttctc cgccgttagt      660
ggaaataatt atgcccatta tgtgaataat tttcaacaag atgcctcttc taccaatcca      720
aatcaagatt caaataatgc cgaatttgag aatattgaat tttctacccc acaaatgatg      780
cccgttgaag atgctgaaac ttggatgaac aacatgggtc caattccgaa cttctctctc      840
gatgtgaaca ggaacattgg tgatagcttt acagatatac aacacaagaa ttcagagcct      900
attatatccg aaccgcccaa ggacaccgct ccaaacgaca agaagttgaa tggctactct      960
ttttacgaag cccccatcaa gccattagaa tccctatttt ctgtcaggaa tacaaagaga     1020
aacaagtata aacaaatga cgactctcca gacaccgtgg ataataactc cgcaccggct      1080
gctaatacca ttcaagaact tgagtcttct ttgaatgcat ccaagaattt ttgcttgcca     1140
actggttatt ccttctatgg taatttggac caacagactt tctctaacac gttatcatgc     1200
acttcttcta atgccacaat ttcgcccatt ctactcgata actccattaa taataactcc     1260
actagtgacg tgagaccaga atttagaaca caaagtgtca cctctgaaat gagtcaagcc     1320 cctcccccte ctcaaaaaaa caactcgaaa tattccaccg aagttctttt taccagcaac     1380
atgcggtcgt ttattcacta cgctctttcc aagtatcctt ttattggtgt gcccactcca     1440
actcttccgg agaacgaaag actaaatgaa tatgctgatt cattcaccaa ccgtttctta     1500
aatcattatc ctttcataca tgtcacgatt ctcaaagaat actccctttt caaggcaatt     1560
ttagatgaga atgagtcgac taagaactgg gaaaataatc agttttactt agagaaccaa     1620
cgaatatcaa ttgtttgtct tcctcttttg gtggctacga taggtgcagt actatcaaac     1680
aacaaaaagg atgcttcgaa tttatacgaa gcttcaaggc gttgtattca tgtttactta     1740
gattccagga aaaagatacc cacttccttg tccgcaaata acaatgactc tccacttttgg    1800 ctaattcaat ccctgacgtt atctgttatg tatgggttat ttgcggacaa tgacattagt     1860
ttgaatgtcg tgatcagaca agttaacgca cttaattctc tggtcaagac ttcgggcctg     1920
aataggacct caattataga tcttttcaac atcaacaaac ctttggataa tgaactctgg     1980
aatcaattcg tgaaaataga gtccaccgta aggacaatcc acacgatttt tcaaatcagt     2040
tccaacttaa gcgccttgta caatattatt ccatcgttga aaattgatga cctaatgatt     2100
actctaccag ttcccacaac actttggcaa gctgattctt ttgtgaaatt caaaagtcta     2160
agttacggaa atcagatccc ttttcaatat acaagagtac tacagaattt gattgattac     2220
aatcagccat tgagcgatgg aaaatttttg tatgaaaacc atgtaagtga gtttggactc     2280
atatgcctac agaatggtct acaccaatac agctatttcc aaaaattgac tgctgtcaat     2340
aacagagaag atgcgctatt cacaaaggtt gttaattcac ttcacagttg ggataggatg     2400
atttcgaatt ctgatttgtt tccaagaaag atatatcagc agagttgctt gattttggac     2460
tcaaagttgc ttaataattt cctgattgtc aagagctcat tgaaagtttc gaccggagac     2520
```

```
gttagttctt tgaataagtt aaaagaaaac gtgtggctta aaaactggaa tcaagtgtgt    2580
gctatctatt ataacagctt catgaacatt cctgctccca gtattcaaaa gaagtacaat    2640
gacatagagt ttgtggatga catgattaat ttgagtctaa tcatcatcaa gattatgaaa    2700
ctcattttct ataacaatgt caaagacaat tatgaggatg aaaatgactt caaattgcaa    2760
gagttaaatt taacatttga caattttgat gagaaaatat ccttgaattt gacaatatta    2820
ttcgatatat ttttgatgat ctacaagata attaccaatt acgaaaagtt tatgaagatc    2880
aaacacaagt ttaattacta caattctaat tcgaatataa gcttcttgca tcatttcgaa    2940
ctctcctcgg ttatcaataa cacccaaatg aaccagaatg attatatgaa aacagatatt    3000
gatgaaaagc ttgatcagct tttccacatc tatcaaacat ttttccggct gtatctggat    3060
ttagaaaagt ttatgaagtt caaattcaac tatcatgact ttgagacaga gttttcaagt    3120
ctctcaatat ccaatatact gaacactcat gctgcttcta acaatgacac aaatgctgct    3180
gatgctatga atgccaagga tgaaaaaata tctcccacaa ctttgaatag cgtattactt    3240
gctgatgaag gaaatgaaaa ttccggtcgt aataacgatt cagaccgcct gttcatgctg    3300
aacgagctaa ttaattttga agtaggtttg aaatttctca agataggtga gtcattttt    3360 gatttcttgt atgagaataa ctacaagttc atccacttca aaaacttaaa tgacggaatg    3420
ttccacatca ggatatacct agaaaaccga ctagatggtg gtgtctag              3468
```

UNITED STATES PATENT AND TRADEMARK OFFICE
CERTIFICATE OF CORRECTION

PATENT NO. : 10,689,656 B2
APPLICATION NO. : 15/573300
DATED : June 23, 2020
INVENTOR(S) : Smita Shankar and Martin Andrew Hoyt Page 1 of 1

It is certified that error appears in the above-identified patent and that said Letters Patent is hereby corrected as shown below:

In the Claims

Column 90 Line 12 Claim 26, delete "Mxrl1" and insert --Mxr1--, therefor.

Signed and Sealed this
Fifteenth Day of September, 2020

Andrei Iancu
*Director of the United States Patent and Trademark Office*